US007169752B2

(12) United States Patent
Mickle et al.

(10) Patent No.: US 7,169,752 B2
(45) Date of Patent: Jan. 30, 2007

(54) COMPOUNDS AND COMPOSITIONS FOR PREVENTION OF OVERDOSE OF OXYCODONE

(75) Inventors: Travis Mickle, Charlottesville, VA (US); Suma Krishnan, Blacksburg, VA (US); James Scott Moncrief, Christiansburg, VA (US); Christopher Lauderback, Blacksburg, VA (US); Sanjib Bera, Blacksburg, VA (US); Sven Guenther, Blacksburg, VA (US); Wendy Hirschelman, Blacksburg, VA (US)

(73) Assignee: New River Pharmaceuticals Inc., Radford, VA (US)

( * ) Notice: Subject to any disclaimer, the term of this patent is extended or adjusted under 35 U.S.C. 154(b) by 0 days.

(21) Appl. No.: 10/955,006

(22) Filed: Sep. 30, 2004

(65) Prior Publication Data
US 2005/0176644 A1 Aug. 11, 2005

Related U.S. Application Data

(60) Provisional application No. 60/567,802, filed on May 5, 2004, provisional application No. 60/567,800, filed on May 5, 2004, provisional application No. 60/507,012, filed on Sep. 30, 2003.

(51) Int. Cl.
```
A61K 38/00    (2006.01)
A61K 38/02    (2006.01)
A61K 38/10    (2006.01)
A61K 38/08    (2006.01)
A61K 38/06    (2006.01)
A61K 38/07    (2006.01)
A61K 38/05    (2006.01)
C07K 5/06     (2006.01)
C07K 2/00     (2006.01)
C07K 7/08     (2006.01)
C07K 7/04     (2006.01)
C07K 5/10     (2006.01)
C07K 5/08     (2006.01)
```
(52) U.S. Cl. .............................. 514/2; 514/14; 514/15; 514/16; 514/17; 514/18; 514/19; 514/563; 530/300; 530/327; 530/328; 530/329; 530/330; 530/331

(58) Field of Classification Search ............... None
See application file for complete search history.

(56) References Cited

U.S. PATENT DOCUMENTS

| | | | |
|---|---|---|---|
| 3,843,696 A | 10/1974 | Wagner et al. |
| 3,846,399 A | 11/1974 | Hirschmann et al. |
| 3,878,187 A | 4/1975 | Schneider et al. |
| 3,884,898 A | 5/1975 | Schneider |
| 3,975,342 A | 8/1976 | Gross |
| 3,998,799 A | 12/1976 | Bodor et al. |
| 4,025,501 A | 5/1977 | Leute |
| 4,040,907 A | 8/1977 | Ullman et al. |
| 4,346,166 A | 8/1982 | Montag et al. |
| 4,356,166 A | 10/1982 | Peterson et al. |
| 4,399,121 A | 8/1983 | Albarella et al. |
| 4,427,660 A | 1/1984 | Schiffman et al. |
| 4,457,907 A | 7/1984 | Porter |
| 4,552,864 A | 11/1985 | Antoni et al. |
| 4,650,675 A | 3/1987 | Borel et al. |
| 4,730,048 A | 3/1988 | Portoghese |
| 4,801,575 A | 1/1989 | Pardridge |
| 4,863,735 A | 9/1989 | Kohn et al. |
| 4,902,505 A | 2/1990 | Pardridge et al. |
| 4,960,790 A | 10/1990 | Stella et al. |
| 4,976,962 A | 12/1990 | Bichon et al. |
| 5,026,827 A | 6/1991 | Miyazaki |
| 5,073,641 A | 12/1991 | Bundgaard et al. |
| 5,087,616 A | 2/1992 | Myers et al. |
| 5,169,933 A | 12/1992 | Anderson et al. |
| 5,183,883 A | 2/1993 | Tanaka et al. |
| 5,219,564 A | 6/1993 | Zalipsky et al. |
| 5,238,714 A | 8/1993 | Wallace et al. |
| 5,362,831 A | 11/1994 | Mongelli et al. |
| 5,534,496 A | 7/1996 | Lee et al. |
| 5,610,283 A | 3/1997 | Buechler |
| 5,618,926 A | 4/1997 | Salamone et al. |

(Continued)

FOREIGN PATENT DOCUMENTS

WO    WO 94/11021 A    5/1994

(Continued)

OTHER PUBLICATIONS

Chapter 1. The Controlled Substances Act. DEA. Web document <http://www.dea.gov/pubs/abuse/1-csa.htm>, 18 pages; accessed Apr. 28, 2006.*

(Continued)

*Primary Examiner*—Cecilia J. Tsang
*Assistant Examiner*—Andrew D. Kosar
(74) *Attorney, Agent, or Firm*—Hunton & Williams LLP

(57) ABSTRACT

The invention relates to pharmaceutical compounds and compositions comprised of a chemical moiety attached to an opioid such as oxycodone in a manner that substantially decreases the potential of the opioid to cause overdose. When delivered at the proper dosage the pharmaceutical composition provides therapeutic activity similar to that of the parent active agent. Further the compounds and compositions of the invention are useful in preventing addiction and susceptibility to addiction.

87 Claims, 45 Drawing Sheets

U.S. PATENT DOCUMENTS

| | | | |
|---|---|---|---|
| 5,670,477 | A | 9/1997 | Poduslo et al. |
| 5,762,909 | A | 6/1998 | Uzgiris |
| 5,767,227 | A | 6/1998 | Latham et al. |
| 5,846,743 | A | 12/1998 | Janmey et al. |
| 5,851,536 | A | 12/1998 | Yager et al. |
| 5,863,899 | A | 1/1999 | Cheronis et al. |
| 5,882,645 | A | 3/1999 | Toth et al. |
| 5,891,459 | A | 4/1999 | Cooke et al. |
| 5,898,033 | A | 4/1999 | Swadesh et al. |
| 5,910,569 | A | 6/1999 | Latham et al. |
| 5,948,750 | A | 9/1999 | Garsky et al. |
| 5,952,294 | A | 9/1999 | Lazo et al. |
| 5,977,163 | A | 11/1999 | Li et al. |
| 6,005,004 | A | 12/1999 | Katz et al. |
| 6,030,941 | A | 2/2000 | Summerton et al. |
| 6,043,230 | A | 3/2000 | Arimilli et al. |
| 6,048,736 | A | 4/2000 | Kosak |
| 6,074,659 | A | 6/2000 | Kunz et al. |
| 6,075,120 | A | 6/2000 | Cheronis et al. |
| 6,093,391 | A | 7/2000 | Kabanov et al. |
| 6,235,718 | B1 | 5/2001 | Balasubramanium |
| 6,255,285 | B1 | 7/2001 | Kotake |
| 6,306,993 | B1 | 10/2001 | Rothbard et al. |
| 6,309,633 | B1 | 10/2001 | Ekwuribe et al. |
| 6,458,842 | B1 | 10/2002 | Dickinson et al. |
| 6,716,452 | B1 | 4/2004 | Piccariello et al. |
| 6,740,641 | B2 | 5/2004 | Gao et al. |
| 6,784,186 | B1 | 8/2004 | Jackson |
| 7,060,708 | B2 | 6/2006 | Piccariello et al. |
| 2001/0031873 | A1 | 10/2001 | Greenwald et al. |
| 2002/0059013 | A1 | 5/2002 | Rajala et al. |
| 2002/0098999 | A1 | 7/2002 | Gallop et al. |
| 2002/0099013 | A1 | 7/2002 | Piccariello et al. |
| 2002/0151526 | A1 | 10/2002 | Gallop et al. |
| 2002/0151529 | A1 | 10/2002 | Cundy et al. |
| 2004/0058946 | A1 | 3/2004 | Buchwald et al. |
| 2004/0180036 | A1 | 9/2004 | Ashton et al. |
| 2004/0204434 | A1 | 10/2004 | Shafer |
| 2005/0038121 | A1 | 2/2005 | Mickle et al. |
| 2005/0054561 | A1 | 3/2005 | Mickle et al. |
| 2005/0065086 | A1 | 3/2005 | Mickle et al. |
| 2005/0069550 | A1 | 3/2005 | Mickle et al. |
| 2005/0074425 | A1 | 4/2005 | Waugh et al. |
| 2005/0080012 | A1 | 4/2005 | Mickle et al. |
| 2005/0112088 | A1 | 5/2005 | Zhao et al. |
| 2005/0176644 | A1 | 8/2005 | Mickle et al. |
| 2005/0176645 | A1 | 8/2005 | Mickle et al. |
| 2005/0176646 | A1* | 8/2005 | Mickle et al. ............... 514/16 |
| 2005/0266070 | A1 | 12/2005 | Mickle et al. |
| 2006/0014697 | A1* | 1/2006 | Mickle et al. ............... 514/17 |

FOREIGN PATENT DOCUMENTS

| | | |
|---|---|---|
| WO | WO 00/37103 A | 6/2000 |
| WO | WO 2004-064839 | 8/2004 |
| WO | WO 2004-082620 | 9/2004 |
| WO | WO 2005-118642 | 12/2005 |
| WO | WO 2006-059106 | 6/2006 |

OTHER PUBLICATIONS

Aggarwal, et al., "Synthesis and Biological Evaluation of Prodrugs of Zidovudine," *J. Med. Chem.*, 33(5):1505-1511 (1990).

Amidon, G., et al., "A Theoretical Basis for a Biopharmaceutic Drug Classification: The Correlation of *in Vitro* Drug Product Dissolution and *in Vivo* Bioavailability," *Pharmaceutical Research*, vol. 12, No. 3 (1995).

Balimane, P., et al., "Effect of Ionization on the Variable Uptake of Valacyclovir via the Human Intestinal Peptide Transporter (hPepT1) in CHP cells," *Biopharm Drug Dispos*, 21(5):165-174 (2000), Abstract.

Balimane, P.V., et al., "Direct Evidence for Peptide Transporter (PepT1)-Mediated Uptake of a Nonpeptide Prodrug, Valacyclovir," *Biochem Biophys Res Commun*, 250(2):246-251 (1998), Abstract.

Bunevicius, R., "Effects of Thyroxine as Compared with Thyroxine Plus Triiodothyronine in Patients with Hypothyroidism," *The New England Journal of Medicine*, vol. 340, No. 6 (1999).

Burnette, Thimysta C., et al., "Metabolic Disposition of the Acyclovir Prodrug Valaciclovir in the Rat," *Drug Metabolism and Disposition*, 22(1):60-64 (1994).

Canaris, G., "The Colorado Thyroid Disease Prevalence Study," *Archives Internal Medicine Articles and Abstracts*, vol. 160, No. 4 (2000).

De Vrueh, Remco L.A., et al, "Transport of L-Valine-Acyclovir Via the Oligopeptide Transporter in the Human Intestinal Cell Line, Caco-2," *Journal of Pharmacology and Experimental Therapeutics*, 286(2): 1166-1170 (1988).

Friedrichsen, G.M., et al., "Model Prodrugs Designed for the Intestinal Peptide Transporter. A Synthetic Approach for Coupling of Hydroxy-Containing Compounds to Dipeptides," *Eur J Pharm Sci*, 14(1):13-19 (2001, Abstract.

Guo, A., et al., "Interactions of a Nonpeptidic Drug. Valacyclovir, with the Human Intestinal Peptide Transporter (hPEPT1) Expressed in a Mammalian Cell Line," *Pharmacol Exp Ther*, 289(1):448-454 (1999), Abstract.

Han H., et al., "5'-Amino Acid Esters of Antiviral Nucleosides, Acyclovir, and AZT and Absorbed by the Intestinal PEPT1 Peotide Transporter," *Pharm Res*, 15(8):1154-1159 (1998), Abstract.

Han, H.K., et al., "Cellular Uptake Mechanism of Amino Acid Ester prodrugs in Caco-2hPEPT1 Cells Overexpressing a Human Peptide Transporter," *Pharm Res*, 15(9):1382-1386 (1998), Abstract.

Han, Hyo-Kyung, et al., "Targeted Prodrug Design to Optimize Drug Delivery," *AAPS PharmSci*, 2(1): Article 6 (2000).

Havranova, Marie et al., "A High-Molecular Mass Derivative of Trypsin-Kallikrein Inhibitor for Potential Medical Use, II," *Hoppe-Seyler's Z. Physiol. Chem.*, 363:295-303 (1982).

Hosztafi, S. et al. "Synthesis and Analgetic Activity of Nicotinic Esters of Morphine Derivatives," *Arzneim.-Forsch./Drug Res.* 43(II), Nr. 11 (1993).

International Search Report, dated Oct. 9, 2003, for PCT/US03/05525.

International Search Report, dated Sep. 3, 2003.

Knutter, I. et al., "A Novel Inhibitor of the Mammalian Peptide Transporter PEPT1," *Biochemistry*, 40(14):4454-4458 (2001), Abstract.

Kovacs, J., et al., "Glutamic and Aspartic Anhydrides. Rearrangement of N-Carboxyglutamic 1,5-Anhydride to the Leuchs' Anhydride and Conversion of the Latter to Pyroglutamic Acid,".

Kramer, Werner et al., "Intestinal Absorption of Peptides by Coupling to Bile Acids," *The Journal of Biochemistry*, 269(14):10621-10627 (1994).

Leibach, F.H. et al., "Peptide Transporters in the Intestine and the Kidney," *Annu Rev Nutri*, 16:99-119 (1996), Abstract.

Li, Chun, et al., "Complete Regression of Well-Established Tumors Using a Novel Water-Soluble Poly(L-Glutamic Acid)-Paclitaxel Conjugate," *Cancer Res*, 58:2404-2409 (1998).

Marriq, Claudine, et al., "Amino Acid Sequence of the Unique 3,5,3'-Triiodothyronine-Containing Sequence from Porcine Thyroglobulin," *Biochemical and Biophysical Research Communications*, 112(1):206-213 (1983).

Negishi, Naoki, et al., "Coupling of Naltrexone to Biodegradable Poly (α-Amino Acids)," *Pharmaceutical Research*, 4(4):305-310 (1987).

Nishida, Koyo, et al., "Pharmacokinetic Analysis of *in Vivo* Metabolism of Amino Acid or Dipeptide Conjugates of Salicylic Acid in Rabbit Intestinal Microorganisms," *Pharmaceutical Research*, 11(1):160-164 (1994).

Oh, D., et al., "Estimating the Fraction Dose Absorbed from Suspensions of Poorly Soluble Compounds in Humans: A Mathematical Model," *Pharmaceutical Research*, vol. 10, No. 2 (1993).

Oh, DM, et al., "Drug Transport and Targeting. Intestinal Transport," *Pharma Biotechnol*,12:59-88 (1999), Abstract.

Okada, Masahiko, et al., "Synthesis of Glycopeptide-conjugates via Ring-Opening Polymerization of Sugar-Substituted α-Amino Acid N-Carboxyanhydrides (GlycoNCAs)," *Proc. Japan Acad.*, 73:205-209 (1997).

Orten, James M. et al., "Thyroxine," *Human Biochemistry*, 9$^{th}$ Ed., C.V. Mosby Company, St. Louis, pp. 401-405 (1975).

Pade, V., et al., "Link Between Drug Absorption Solubility and Permeability Measurements in Caco-2 Cells," *Journal of Pharmaceutical Sciences*, vol. 87, No. 12 (1998).

Ryser, Hugues J.P., et al., "Conjugation of Methotrexate to Poly (L-lysine) Increases Drug Transport and Overcomes Drug Resistance in Cultured Cells," *Proc. Natl. Acad. Sci. USA*, 75(8):3867-3870 (1978).

Sawada, Kyoko, et al., "Recognition of L-Amino Acid Ester Compounds by Rat Peptide Transporters PEPT1 and PEPT2," *Journal of Pharmacology and Experimental Therapeutics*, 291(2):705-709 (1999).

Schmidt, Brigitte F., et al., "Peptide-Linked 1,3-Dialkyl-3-acyltriazenes: Gastrin Receptor Directed Antineoplastic Alkylating Agents," *Journal of Medicinal Chemistry*, 37(22):3812-3817 (1994).

Shen, H., et al., "Developmental Expression of PEPT1 and PEPT2 in Rat Small Intestine, Colon, and Kidney," *Pediatr Res*, 49(6):789-795 (2001), Abstract.

Shiraga, T., et al., "Cellular and Molecular Mechanisms of Dietary Regulation on Rat Intestinal H+/Peptide Transporter PepT1," *Gastroenterology*, 116(2):354-362 (1999), Abstract.

Tamai, I., et al., "Improvement of L-dopa Absorption by Dipeptidyl Derivation, Utilizing Peptide Transporter PepT1," *J. Pharma. Sci.*, 87(12):1542-1546 (1988), Abstract.

Toft, A., "Thyroid Hormone Replacement—One Hormone or Two!," *The New England Journal of Medicine*, vol. 340, No. 6 (1999).

Toth, Istvan, "A Novel Chemical Approach to Drug Delivery: Lipidic Amino Acid Conjugates," *Journal of Drug Targeting*, 2:217-239 (1994).

Zunino, Franco, et al., "Anti-Tumor Activity of Daunorubicin Linked to Poly-L-Aspartic Acid," *International Journal of Cancer*, 30:465-470 (1982).

Zunino, Franco, et al., "Comparison of Antitumor Effects of Daunorubicin Covalently Linked to Poly-L-Amino Acid Carriers," *European Journal of Cancer & Clinical Oncology*, 20(3):121-125 (1984).

Supplementary European Search Report for EP 01273387 dated Sep. 28, 2004.

U.S. Appl. No. 10/923,088, Entitled "Active Agent Delivery Systems And Methods For Protecting And Administering Active Agents", Mickle et al., filed Aug. 23, 2004.

U.S. Appl. No. 10/953,111, Entitled "Compounds and Compositions for the Prevention of Overdose of Oxycodone", Mickle et al., filed Aug. 23, 2004.

U.S. Appl. No. 11/179,801, Entitled "Carbohydrate Conjugates to Prevent Abuse of Controlled Susbstances", Mickle et al., filed Jul. 13, 2005.

U.S. Appl. No. 11/392,878, Entitled "Pharmaceutical Compositions for Prevention of Overdose or Abuse", Mickle et al., filed Apr. 4, 2006.

U.S. Appl. No. 11/400,304, Entitled "Abuse Resistant Amphetamine Prodrugs", Mickle et al., filed Apr. 10, 2006.

* cited by examiner

Niacin

Biotin

COMPOUNDS AND COMPOSITIONS FOR PREVENTION OF OVERDOSE OF OXYCODONE

CROSS REFERENCE RELATED APPLICATIONS

This application claims benefit under 35 U.S.C. 119(e) to U.S. Provisional application No. 60/567,800 filed May 5, 2004; U.S. Provisional application No. 60/507,012 filed Sep. 30, 2003; U.S. Provisional application No. 60/567,802 filed on May 5, 2004, all of which are hereby incorporated by reference in their entirety.

FIELD OF INVENTION

Accidental and intentional overdose with prescription and over the counter drugs is a serious health problem with thousands of fatalities occurring each year as a result. The present invention relates to pharmaceutical compositions comprised of a chemical moiety attached to an opioid such as oxycodone in a manner that substantially decreases the potential of the opioid to cause overdose. When delivered at the proper dosage the pharmaceutical composition provides therapeutic activity similar to that of the parent active agent. However, when the composition is delivered at higher doses the potential for overdose is reduced due to the limited bioavailability of the active agent as compared to the opioid delivered as free drug.

BACKGROUND

Drug overdose is a significant and growing problem. It can occur accidentally, as when a child swallows pills without understanding the consequences, or intentionally as with suicide attempts. In addition, accidental overdose due to an unusually potent batch of a street drug in illicit drug users is quite common. Common examples of drugs that are seen in overdose cases include the ubiquitous over-the-counter analgesics acetaminophen (paracetamol) and aspirin. While the former is the preferred drug among adolescents in cases of deliberate self poisonings (Lifshitz et al., Isr. Med. Assoc. J., 4(4): 252–4 (2002), aspirin is perhaps more dangerous because there is no antidote (Jones, Am. J. Ther. 9(3): 245–57 (2002).

In the elderly population, drugs most often implicated in poisonings include psychotherapeutic drugs, cardiovascular drugs, analgesics and anti-inflammatory drugs, oral hypoglycemics and theophylline (Klein-Schwartz et al., Drugs Aging 1(1): 67–89 (1991). It is important to realize that in many cases where death due to overdose is averted, there appears to be extensive morbidity associated with overdoses (Warner-Smith et al., Addition 97(8): 963–7 (2002).

The Drug Abuse Warning Network (DAWN) reported in June 2003 on the most recent trends in emergency department (ED) visits related to drug abuse. Data was presented for 8-year trends from 1994 to 2001. The following summaries were provided:

In 2001, there were over 638,000 ED visits related to drug abuse in the conterminous U.S. This translates to 252 visits per 100,000 populations or 0.6 percent of all ED visits.

Seven categories of drugs accounted for 85% of the ED mentions in 2001. The ED visits related to drug abuse most frequently involved alcohol, (34% of mentions), marijuana (17%), benzodiazepines (16%), narcotic analgesic combinations (16%), heroin (15%), other analgesics/combinations (12%), and antidepressants (10%).

ED mentions of benzodiazepines increased 14 percent from 2000 to 2001 (from 91,078 to 103,972), as did the top 2 benzodiazapines, alprazolam (up 16%) and benzodiazepines-NOS (up 35%). The latter includes benzodiazepines not identified by name.

ED mentions of narcotic analgesics/combinations rose 21 percent (from 82,373 to 99,317) from 2000 to 2001.

Narcotic analgesics not identified by name were mentioned most frequently (narcotic analgesics-NOS, 32,196 mentions, up 24% from 2000 to 2001), followed by those containing hydrocodone (21,567), oxycodone (18,409, up 70%), and methadone (10,725, up 37%). Narcotic analgesics/combinations containing propoxyphene (5,361), codeine (3,720, down 30%), and morphine (3,403) were much less frequent and not increasing.

Emergency department reporting for a number of drugs rose substantially from 1994 to 2000. These include: amphetamines (10,118 to 18,555, up 83.4%), anticonvulsants, including carbamazepine (9,358 to 14,642, up 56.5%), muscle relaxants, including carisoprodol (12,223 to 19,001, up 55.5%), psychotherapeutic drugs, including SSRI antidepressants, tricyclic antidepressants, and other antidepressants (190,467 to 220,289, up 15.7%). Anxiolytics, sedatives, and hypnotics, including benzodiazepines (74,637 to 103,972, up 27.7%) and narcotic analgesics including codeine, hydrocodone, methadone, oxycodone, propoxyphene and others (44,518 to 99,317, up 123.1%).

Other drugs for which the number of ED mentions did not rise but were still responsible for over 10,000 visits include respiratory agents, including antihistamines (12,238), antipsychotics including risperidone (20,182), nonsteroidal anti-inflammatory agents, including ibuprofen and naproxen (22,663) and acetaminophen (42,044). Aspirin and salicylates-NOS accounted for 8,499 ED visits in 2001.

The commercial drugs benzodiazapines (16%), narcotic analgesics other than heroin (16%), non-narcotic analgesics (12%), and antidepressants (10%) accounted for 54% of ED visits in 2001.

The opioid oxycodone is an ingredient of PERCODAN®, PERCOCET®, ROXICET® (combination of oxycodone and acetaminophan), and TYLOX® (combination of oxycodone and acetaminophan). It is a semisynthetic narcotic analgesic that is derived from thebaine. Available in oral formulations often in combination with aspirin, phenacetin and caffeine. Typical adult dose is 2.5–5 mg as the hydrochloride or terephthalate salt every 6 hours. Although it is typically used for the relief of moderate to moderately severe pain, it can also produce drug dependence of the morphine type. Therapeutic plasma concentration is 10–100 ng/mL and the toxic plasma concentration is greater than 200 ng/mL.

Others have sought to prevent the potential harmful effects of overdose through various formulations. For example, opioids have been combined with antagonists in particular formulations designed to counteract the opioid if the formulation is disrupted before oral administration or is given parenterally. Extended release CONCERTA® (methyiphenidate) has been formulated in a paste to preclude administration by snorting or injection. Compositions have been coated with emetics in a quantity that if administered in moderation as intended no emesis occurs, however, if excessive amounts are consumed emesis is induced therefore preventing overdose. These methods, as well as conventional control release formulations, are insufficient and can be easily circumvented. Consequently, improved methods are needed to make drugs with reduced potential for overdose that are resistant to manipulation.

DETAILED DESCRIPTION OF THE INVENTION

Figure 1:
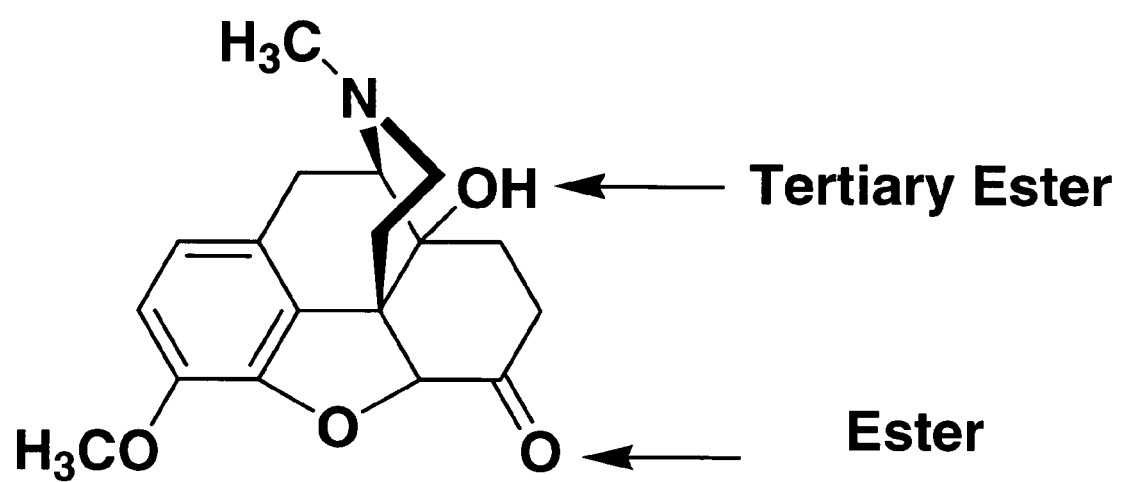
FIG. 1 depicts oxycodone.

The present invention relates to changing the pharmacokinetic and pharmacological properties of opioids, particularly oxycodone and its derivatives, through covalent modification. Covalent attachment of a chemical moiety to an opioid can change the rate and extent of absorption, metabolism, distribution, and elimination of the drug. When administered at a normal therapeutic dose the bioavailablility (area under the time-versus-concentration curve; AUC) of the opioid is similar to that of the parent opioid compound. As the oral dose is increased, however, the bioavailability of the covalently modified opioid relative to the parent opioid begins to decline. At suprapharmacological doses the bioavailability of the opioid conjugate is substantially decreased as compared to the parent opioid. The relative decrease in bioavailability at higher doses abates the euphoria obtained when doses of the opioid conjugate are taken above those of the intended prescription. This in turn diminishes the abuse potential, whether unintended or intentionally sought.

Persons that abuse opioids such as oxycodone commonly seek to increase their euphoria by snorting or injecting the drugs. These routes of administration increase the rate and extent of drug absorption and provide a faster, nearly instantaneous, effect. This increases the amount of drug that reaches the central nervous system where it has its effect. In a particular embodiment of the invention the bioavailability of the covalently modified opioid is substantially decreased by the intranasal and intravenous routes as compared to the parent opioid compound. Thus the illicit practice of snorting and shooting the drug loses its advantage.

In accordance with the present invention and as used herein, the following terms, are defined with the following meanings, unless explicitly stated otherwise. For additional methods of attaching opioids to carriers, see application number U.S. Ser. No. 10/156,527, and/or PCT/US03/05524 and/or PCT/US03/05525 each of which is hereby incorporated by reference in its entirety.

The invention utilizes covalent modification of the opioid oxycodone to decrease its potential for causing overdose or abuse. Oxycodone is covalently modified in a manner that decreases its pharmacological activity, as compared to the unmodified oxycodone, at doses above those considered therapeutic. When given at lower doses, such as those intended for therapy, the covalently modified oxycodone retains pharmacological activity similar to that of the unmodified oxycodone. The covalent modification of oxycodone may comprise the attachment of any chemical moiety through conventional chemistry.

Compounds, compositions and methods of the invention provide reduced potential for overdose, reduced potential for abuse or addiction and/or improve oxycodone's characteristics with regard to high toxicities or suboptimal release profiles. Without wishing to be limited to the below theory, we believe that overdose protection results from a natural gating mechanism at the site of hydrolysis that limits the release of the active oxycodone from the prodrug at greater than therapeutically prescribed amounts. Therefore, abuse resistance is provided by limiting the "rush" or "high" available from the active oxycodone released by the prodrug and limiting the effectiveness of alternative routes of administration.

Throughout this application the use of "opioid" is meant to include any drug that activates the opioid receptors found in the brain, spinal cord and gut. There are three broad classes of opioids: naturally occurring opium alkaloids, such as morphine (the prototypical opioid) and codeine; semi-synthetics such as heroine, oxycodone and hydrocodone that are produced by modifying natural opium alkaloids and have similar chemical structures; and pure synthetics such as fentanyl and methadone that are not produced from opium and may have very different chemical structures than the opium alkaloids. Other opioids include hydroxymorphone, oxymorphone, methadone, levorphanol, dihydrocodeine, meperidine, diphenoxylate, sufentanil, alfentanil, propoxyphene, pentazocine, nalbuphine, butorphanol, buprenorphine, meptazinol, dezocine, and pharmaceutically acceptable salts thereof.

Throughout this application the use of "oxyocodone" is meant to include a narcotic alkaloid (chemical formula $C_{18}H_{21}NO_4$) and its derivatives such as the hydrochloride salt of oxycodone. Oxycodone is related to codeine and is used as an analgesic and/or a sedative. Oxycodone is a powerful and potentially addictive opioid analgesic synthesized from thebaine. It is similar to codeine, but is more potent and has a higher dependence potential. It is effective orally and is often marketed in combination with aspirin (PERCODAN®) or acetaminophen (PERCOCET®) for the relief of pain. It is also sold in a sustained-release form under the trade name OXYCONTIN®. All of these deriviatives or combinations of oxycodone are encompassed by the present invention.

Throughout this application the use of "peptide" is meant to include a single amino acid, a dipeptide, a tripeptide, an oligopeptide, a polypeptide, or the carrier peptide. Oligopeptide is meant to include from 2 amino acids to 70 amino acids. Further, at times the invention is described as being an active agent attached to an amino acid, a dipeptide, a tripeptide, an oligopeptide, or polypeptide to illustrate specific embodiments for the active agent conjugate. Preferred lengths of the conjugates and other preferred embodiments are described herein.

Throughout this application the use of "chemical moiety" is meant to include at least amino acids, peptides, glycopeptides, carbohydrates, lipids, nucleosides, or vitamins.

Carbohydrates includes sugars, starches, cellulose, and related compounds. e.g., $(CH_2O)_n$, wherein n is an integer larger than 2 or $C_n(H_2O)_{n-1}$, with n larger than 5. More specific examples include for instance, fructose, glucose, lactose, maltose, sucrose, glyceraldehyde, dihydroxyacetone, erythrose, ribose, ribulose, xylulose, galactose, mannose, sedoheptulose, neuraminic acid, dextrin, and glycogen.

A glycoprotein is a compound containing carbohydrate (or glycan) covalently linked to protein. The carbohydrate may be in the form of a monosaccharide, disaccharide(s), oligosaccharide(s), polysaccharide(s), or their derivatives (e.g. sulfo- or phospho-substituted).

A glycopeptide is a compound consisting of carbohydrate linked to an oligopeptide composed of L- and/or D-amino acids. A glyco-amino-acid is a saccharide attached to a single amino acid by any kind of covalent bond. A glycosyl-amino-acid is a compound consisting of saccharide linked through a glycosyl linkage (O—, N— or S—) to an amino acid.

A "composition" as used herein, refers broadly to any composition containing a described molecule conjugates. The composition may comprise a dry formulation, an aqueous solution, or a sterile composition. Compositions comprising the molecules described herein may be stored in freeze-dried form and may be associated with a stabilizing agent such as a carbohydrate. In use, the composition may be deployed in an aqueous solution containing salts, e.g., NaCl, detergents, e.g., sodium dodecyl sulfate (SDS), and other components.

Important note regarding stereochemistry: This patent is meant to cover all compounds discussed regardless of absolute configurations. Thus, natural, L-amino acids are discussed but the use of D-amino acids are also included.

BOC=t-butyloxycarbonyl
CMC=carboxymethylcellulose
DIPEA=di-isopropyl ethyl amine
mp=melting point
NMR=nuclear magnetic resonance
OSu=hydroxysuccinimido ester
Nia=Niacin
Bio=Biotin The attached chemical moiety may be any chemical substance that decreases the pharmacological activity until oxycodone is released. Preferably the chemical moiety is a single amino acid, dipeptide or tripeptide. Oxycodone binds to specific sites to produce various effects (Hoebel, et al., 1989). The attachment of certain chemical moieties can therefore diminish or prevent binding to these biological target sites. Preferably, absorption of the composition into the brain is prevented or substantially diminished and delayed when delivered by routes other than oral administration.

The attached chemical moiety may further comprise naturally occurring or synthetic substances. This would include but is not limited to the attachment of oxycodone to one or more amino acids, peptides, lipids, carbohydrates, glycopeptides, nucleic acids or vitamins. These chemical moieties could be expected to affect delayed release in the gastrointestinal tract and prevent rapid onset of the desired activity, particularly when delivered by parenteral routes. (Hoebel, B. G., L. Hernandez, et al. (1989). "Microdialysis studies of brain norepinephrine, serotonin, and dopamine release during ingestive behavior. Theoretical and clinical implications." *Ann NY Acad Sci* 575: 171–91).

For each of the recited embodiments the amino acid or peptide may comprise of one or more of the naturally occurring (L-) amino acids: alanine, arginine, asparagine, aspartic acid, cysteine, glycine, glutamic acid, glutamine, histidine, isoleucine, leucine, lysine, methionine, proline, phenylalanine, serine, tryptophan, threonine, tyrosine, and valine. In another embodiment the amino acid or peptide is comprised of one or more of the naturally occurring (D) amino acids: alanine, arginine, asparagine, aspartic acid, cysteine, glycine, glutamic acid, glutamine, histidine, isoleucine, leucine, lysine, methionine, proline, phenylalanine, serine, tryptophan, threonine, tyrosine, and valine. In another embodiment the amino acid or peptide is comprised of one or more unnatural, non-standard or synthetic amino acids such as, aminohexanoic acid, biphenylalanine, cyclohexylalanine, cyclohexylglycine, diethylglycine, dipropylglycine, 2,3-diaminoproprionic acid, homophenylalanine, homoserine, homotyrosine, naphthylalanine, norleucine, ornithine, pheylalanine(4-fluoro), phenylalanine(2,3,4,5,6 pentafluoro), phenylalanine(4-nitro), phenylglycine, pipecolic acid, sarcosine, tetrahydroisoquinoline-3-carboxylic acid, and tert-leucine. In another embodiment the amino acid or peptide comprises of one or more amino acid alcohols. In another embodiment the amino acid or peptide comprises of one or more N-methyl amino acids.

In another embodiment, the specific carriers are utilized as a base short chain amino acid sequence and additional amino acids are added to the terminus or side chain. In another embodiment, the above amino acid sequence may have one more of the amino acids substituted with one of the 20 naturally occurring amino acids. It is preferred that the substitution be with an amino acid which is similar in structure or charge compared to the amino acid in the sequence. For instance, isoleucine (Ile)[I] is structurally very similar to leucine (Leu)[L], whereas, tyrosine (Tyr)[Y] is similar to phenylalanine (Phe)[F], whereas serine (Ser)[S] is similar to threonine (Thr)[T], whereas cysteine (Cys)[C] is similar to methionine (Met)[M], whereas alanine (Ala)[A] is similar to valine (Val)[V], whereas lysine (Lys)[K] is similar to arginine (Arg)[R], whereas asparagine (Asn)[N] is similar to glutamine (Gln)[Q], whereas aspartic acid (Asp)[D] is similar to glutamic acid (Glu)[E], whereas histidine (His)[H] is similar to proline (Pro)[P], and glycine (Gly)[G] is similar to tryptophan (Trp)[W]. In the alternative the preferred amino acid substitutions may be selected according to hydrophilic properties (i.e. polarity) or other common characteristics associated with the 20 essential amino acids. While preferred embodiments utilize the 20 natural amino acids for their GRAS characteristics, it is recognized that minor substitutions along the amino acid chain which do not effect the essential characteristics of the amino are also contemplated.

In one embodiment the carrier range is between one to 12 chemical moieties with one to 8 moieties being preferred. In another embodiment the number of chemical moieties attached is selected from 1, 2, 3, 4, 5, 6, or 7. In another embodiment of the invention the molecular weight of the carrier portion of the conjugate is below about 2,500, more preferably below about 1,000 and most preferably below about 500.

In one embodiment the opioid is oxycodone and the pharmaceutical carrier (chemical moiety) is comprised of a peptide of two or more amino acids. Preferred peptide chemical moieties include, for example, Phe, Ile, Pro-Pro-Leu, Pro-Pro-Ile, Val-Val, Lys-Lys, Gly-Gly-Ile, Phe-Phe-Ile, Phe-Phe-Leu, Thr-Thr-Val, Tyr-Tyr-Val, Tyr-Tyr-Phe, Glu-Glu-Val, Asp-Asp-Val, Lys-Lys-Val, Glu-Glu-Phe-Phe-Ile [SEQ ID NO: 1], Glu-Glu-Phe-Phe-Phe [SEQ ID NO: 2], Tyr-Tyr-Ile, Asp-Asp-Ile, Tyr-Tyr-Phe-Phe-Ile [SEQ ID NO: 3], Tyr-Tyr-Lys-Tyr-Tyr [SEQ ID NO: 4], Phe-Phe-Lys-Phe-Phe [SEQ ID NO: 5], (Lys-Lys-Gly-Gly)$_2$ [SEQ ID NO: 6], and [(1)-Lys-(d)-Lys-Leu]$_2$. In some embodiments, the oxycodone is disubstituted with one or more of the preceding chemical moieties.

Another embodiment of the invention is a composition for preventing overdose comprising oxycodone which has been covalently bound to a chemical moiety.

Another embodiment of the invention is a composition for safely delivering oxycodone comprising providing a therapeutically effective amount of said oxycodone which has been covalently bound to a chemical moiety wherein said chemical moiety reduces the rate of absorption of the oxycodone as compared to delivering the unbound oxycodone.

Another embodiment of the invention is a composition for reducing drug toxicity comprising providing a patient with oxycodone which has been covalently bound to a chemical moiety wherein said chemical moiety increases the rate of clearance of a oxycodone when given at doses exceeding those within the therapeutic range of said oxycodone.

Another embodiment of the invention is a composition for reducing drug toxicity comprising providing a patient with oxycodone which has been covalently bound to a chemical moiety wherein said chemical moiety provides a serum release curve which does not increase above said oxycodone toxicity level when given at doses exceeding those within the therapeutic range of said oxycodone.

Another embodiment of the invention is a composition for reducing bioavailability of oxycodone comprising oxycodone covalently bound to a chemical moiety wherein said bound oxycodone maintains a steady-state serum release curve which provides a therapeutically effective bioavailability but prevents spiking or increase blood serum concentrations compared to unbound oxycodone when given at doses exceeding those within the therapeutic range of said oxycodone.

Another embodiment of the invention is a composition for preventing a $C_{max}$ spike for oxycodone while still providing a therapeutically effective bioavailability curve comprising oxycodone which has been covalently bound to a chemical moiety.

Another embodiment of the invention is a composition for preventing a toxic release profile in a patient comprising oxycodone covalently bound to a chemical moiety wherein said bound oxycodone maintains a steady-state serum release curve which provides a therapeutically effective bioavailability but prevents spiking or increase blood serum concentrations compared to unbound oxycodone.

Another embodiment of the invention is a compound of Formula I:

$$O—X_n-Z_m$$

wherein O is oxycodone as defined herein; X is a chemical moiety as defined herein and n is between 1 and 50 and increments thereof; and Z is a further chemical moiety different from X which acts as an adjuvant and m is between 1 and 50 and increments thereof. In another embodiment n is between 1 and 10 and m is 0. It will be appreciated that compounds of the above formula may be used for any of the recited embodiments.

Embodiments of the invention provide oxycodone compositions which allow the oxycodone to be therapeutically effective when delivered at the proper dosage but reduces the rate of absorption or extent of bioavailability of the oxycodone when given at doses exceeding those within the therapeutic range of the active agent. Embodiments of the invention also provide oxycodone compositions wherein the covalently bound chemical moiety increases the rate of clearance of oxycodone when given at doses exceeding those within the therapeutic range of the oxycodone.

In another embodiment the oxycodone compositions have substantially lower toxicity compared to unbound active agent. In another embodiment the oxycodone compositions reduce or eliminate the possibility of overdose by oral administration. In another embodiment the oxycodone compositions reduce or eliminate the possibility of overdose by intranasal administration. In another embodiment the oxycodone compositions reduce or eliminate the possibility of overdose by injection.

In another embodiment, the oxycodone conjugates of the invention may further comprise a polymer blend which comprises at least one hydrophilic polymer and at least one water-insoluble polymer. The polymer may be used according to industry standard to further enhance the sustained release properties of the oxycodone conjugate without reducing the abuse resistance. For instance, a composition might include: about 75% to about 95% oxycodone conjugate by weight, from about 0.5% to about 10% of a hydrophilic polymer (e.g. hydroxypropyl methylcellulose), from about 0.5% to about 2.5% of a water-insoluble polymer (e.g. acrylic resin), from about 0.4% to about 1.5% of additives (e.g. magnesium stearate), and from about 0.01% to about 1% colorant by weight. Hydrophilic polymers suitable for use in the sustained release formulation include: one or more natural or partially or totally synthetic hydrophilic gums such as acacia, gum tragacanth, locust bean gum, guar gum, or karaya gum, modified cellulosic substances such as methylcellulose, hydroxomethylcellulose, hydroxypropyl methylcellulose, hydroxypropyl cellulose, hydroxyethylcellulose, carboxymethylcellulose; proteinaceous substances such as agar, pectin, carrageen, and alginates; and other hydrophilic polymers such as carboxypolymethylene, gelatin, casein, zein, bentonite, magnesium aluminum silicate, polysaccharides, modified starch derivatives, and other hydrophilic polymers known to those of skill in the art or a combination of such polymers.

These hydrophilic polymers gel and would dissolve slowly in aqueous acidic media thereby allowing the oxycodone conjugate to diffuse from the gel in the stomach. When the gel reaches the intestines it would dissolve in controlled quantities in the higher pH medium to allow sustained release. Preferred hydrophilic polymers are the hydroxypropyl methylcelluloses such as those manufactured by The Dow Chemical Company and known as Methocel ethers, such as Methocel E10M.

Other formulations may further comprise pharmaceutical additives including, but not limited to: lubricants such as magnesium stearate, calcium stearate, zinc stearate, powdered stearic acid, hydrogenated vegetable oils, talc, polyethylene glycol, and mineral oil; colorants; binders such as sucrose, lactose, gelatin, starch paste, acacia, tragacanth, povidone polyethylene glycol, Pullulan and corn syrup; glidants such as colloidal silicon dioxide and talc; surface active agents such as sodium lauryl sulfate, dioctyl sodium sulfosuccinate, triethanolamine, polyoxyethylene sorbitan, poloxalkol, and quarternary ammonium salts; preservatives and stabilizers; excipients such as lactose, mannitol, glucose, fructose, xylose, galactose, sucrose, maltose, xylitol, sorbitol, chloride, sulfate and phosphate salts of potassium, sodium, and magnesium; and/or any other pharmaceutical additives known to those of skill in the art. Colorants include, but are not limited to, Emerald Green Lake, FD&C Red No. 40, FD&C Yellow No. 6, D&C Yellow No. 10, or FD&C Blue No. 1 and other various certified color additives (See 21 CFR, Part 74). In one preferred embodiment, a sustained release formulation further comprises magnesium stearate and Emerald Green Lake.

An oxycodone conjugate, which is further formulated with excipients may be manufactured according to any appropriate method known to those of skill in the art of pharmaceutical manufacture. For instance, the oxycodone conjugate and a hydrophilic polymer may be mixed in a mixer with an aliquot of water to form a wet granulation. The granulation may be dried to obtain hydrophilic polymer encapsulated granules of oxycodone-conjugate. The resulting granulation may be milled, screened, then blended with various pharmaceutical additives, water insoluble polymer, and additional hydrophilic polymer. The formulation may then tableted and may further be film coated with a protective coating which rapidly dissolves or disperses in gastric juices.

However, it should be noted that the oxycodone conjugate controls the release of oxycodone into the digestive tract over an extended period of time resulting in an improved profile when compared to immediate release combinations and prevention of abuse without the addition of the above additives. In a preferred embodiment no further sustained release additives are required to achieve a blunted or reduced pharmacokinetic curve (e.g. reduced euphoric effect) while achieving therapeutically effective amounts of oxycodone release.

The compounds of the invention can be administered by a variety of dosage forms. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, health bars, confections, animal feeds, cereals, yogurts, cereal coatings, foods, nutritive foods, functional foods and combinations thereof.

However, the most effective means for delivering the abuse-resistant compounds of the invention is orally, to permit maximum release of the oxycodone to provide therapeutic effectiveness and/or sustained release while maintaining abuse resistance. When delivered by the oral route the oxycodone is released into circulation, preferably over an extended period of time as compared to oxycodone alone.

Formulations of the invention suitable for oral administration can be presented as discrete units, such as capsules, caplets or tablets. These oral formulations also can comprise a solution or a suspension in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which is then placed in the feeding tube of a patient who is unable to swallow.

Soft gel or soft gelatin capsules may be prepared, for example by dispersing the formulation in an appropriate vehicle (vegetable oils are commonly used) to form a high viscosity mixture. This mixture is then encapsulated with a gelatin based film using technology and machinery known to those in the soft gel industry. The industrial units so formed are then dried to constant weight.

Chewable tablets, for example may be prepared by mixing the formulations with excipients designed to form a relatively soft, flavored, tablet dosage form that is intended to be chewed rather than swallowed. Conventional tablet machinery and procedures, that is both direct compression and granulation, i.e., or slugging, before compression, can be utilized. Those individuals involved in pharmaceutical solid dosage form production are versed in the processes and the machinery used as the chewable dosage form is a very common dosage form in the pharmaceutical industry.

Film coated tablets, for example may be prepared by coating tablets using techniques such as rotating pan coating methods or air suspension methods to deposit a contiguous film layer on a tablet.

Compressed tablets, for example may be prepared by mixing the formulation with excipients intended to add binding qualities to disintegration qualities. The mixture is either directly compressed or granulated then compressed using methods and machinery known to those in the industry. The resultant compressed tablet dosage units are then packaged according to market need, i.e., unit dose, rolls, bulk bottles, blister packs, etc.

The invention also contemplates the use of biologically-acceptable carriers which may be prepared from a wide range of materials. Without being limited thereto, such materials include diluents, binders and adhesives, lubricants, plasticizers, disintegrants, colorants, bulking substances, flavorings, sweeteners and miscellaneous materials such as buffers and adsorbents in order to prepare a particular medicated composition.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders known to persons skilled in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

Preferred plasticizers may be selected from the group consisting of diethyl phthalate, diethyl sebacate, triethyl citrate, cronotic acid, propylene glycol, butyl phthalate, dibutyl sebacate, castor oil and mixtures thereof, without limitation. As is evident, the plasticizers may be hydrophobic as well as hydrophilic in nature. Water-insoluble hydrophobic substances, such as diethyl phthalate, diethyl sebacate and castor oil are used to delay the release of water-soluble vitamins, such as vitamin B6 and vitamin C. In contrast, hydrophilic plasticizers are used when water-insoluble vitamins are employed which aid in dissolving the encapsulated film, making channels in the surface, which aid in nutritional composition release.

It should be understood that in addition to the ingredients particularly mentioned above, the formulations of this invention can include other suitable agents such as flavoring agents, preservatives and antioxidants. Such antioxidants would be food acceptable and could include vitamin E, carotene, BHT or other antioxidants known to those of skill in the art.

Other compounds which may be included by admixture are, for example, medically inert ingredients, e.g. solid and liquid diluent, such as lactose, dextrose, saccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

For oral administration, fine powders or granules containing diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable or necessary, flavoring, preserving, suspending, thickening or emulsifying agents can be included.

Liquid dispersions for oral administration may be syrups, emulsions or suspensions. The syrups may contain as carrier, for example, saccharose or saccharose with glycerol and/or mannitol and/or sorbitol. In particular a syrup for diabetic patients can contain as carriers only products, for example sorbitol, which do not metabolize to glucose or which metabolize only a very small amount to glucose. The suspensions and the emulsions may contain a carrier, for example a natural gum, agar, sodium alginate, pectin, methylcellulose, carboxymethylcellulose or polyvinyl alcohol.

The dose range for adult human beings will depend on a number of factors including the age, weight and condition of the patient and the administration route. Tablets and other forms of presentation provided in discrete units conveniently contain a daily dose, or an appropriate fraction thereof, of one of the present compounds. For example, units may contain from 5 mg to 500 mg, but more usually from 10 mg to 250 mg, of one of the present compounds.

It is also possible for the dosage form to combine any forms of release known to persons of ordinary skill in the art. These include immediate release, extended release, pulse release, variable release, controlled release, timed release, sustained release, delayed release, long acting, and combinations thereof. The ability to obtain immediate release, extended release, pulse release, variable release, controlled release, timed release, sustained release, delayed release, long acting characteristics and combinations thereof is known in the art.

Compositions of the invention may be administered in a partial, i.e., fractional dose, one or more times during a 24 hour period, a single dose during a 24 hour period of time, a double dose during a 24 hour period of time, or more than a double dose during a 24 hour period of time. Fractional, double or other multiple doses may be taken simultaneously or at different times during the 24 hour period. The doses may be uneven doses with regard to one another or with regard to the individual components at different administration times.

Likewise, the compositions of the invention may be provided in a blister pack or other such pharmaceutical package. Further, the compositions of the present inventive subject matter may further include or be accompanied by indicia allowing individuals to identify the compositions as products for a prescribed treatment. The indicia may further additionally include an indication of the above specified time periods for administering the compositions. For example the indicia may be time indicia indicating a specific or general time of day for administration of the composition, or the indicia may be a day indicia indicating a day of the week for administration of the composition. The blister pack or other combination package may also include a second pharmaceutical product.

It will be appreciated that the pharmacological activity of the compositions of the invention can be demonstrated using standard pharmacological models that are known in the art. Furthermore, it will be appreciated that the inventive compositions can be incorporated or encapsulated in a suitable polymer matrix or membrane for site-specific delivery, or can be functionalized with specific targeting agents capable of effecting site specific delivery. These techniques, as well as other drug delivery techniques are well known in the art.

In another embodiment of the invention, the solubility and dissolution rate of the composition is substantially changed under physiological conditions encountered in the intestine, at mucosal surfaces, or in the bloodstream. In another embodiment the solubility and dissolution rate substantially decrease the bioavailability of the said pharmaceutical, particularly at doses above those intended for therapy. In another embodiment the decrease in bioavailability occurs upon oral administration. In another embodiment the decrease in bioavailability occurs upon intranasal administration. In another embodiment the decrease in bioavailability occurs upon intravenous administration.

Another particular embodiment of the invention provides that when the covalently modified oxycodone is provided for oral dosing in the form (e.g., a tablet or capsule) it is resistant to manipulation. Crushing of the tablet or disruption of the capsule does not substantially increase the rate and amount of oxycodone absorbed when compositions of the invention are ingested.

For each of the described embodiments one or more of the following characteristics may be realized. The toxicity of the compound is substantially lower than that of the unbound oxycodone. The covalently bound chemical moiety reduces or eliminates the possibility of overdose by oral administration. The covalently bound chemical moiety reduces or eliminates the possibility of overdose by intranasal administration. The covalently bound chemical moiety reduces or eliminates the possibility of overdose by injection.

The invention further provides methods for altering oxycodone in a manner that decreases their potential for abuse. Methods of the invention provide various ways to regulate pharmaceutical dosage through covalent attachment of oxycodone to different chemical moieties. One embodiment provides a method of preventing overdose comprising administering to an individual oxycodone which has been covalently bound to a chemical moiety.

Another embodiment provides a method of safely delivering oxycodone comprising providing a therapeutically effective amount of a oxycodone which has been covalently bound to a chemical moiety wherein the chemical moiety reduces the rate of absorption of oxycodone as compared to delivering the unbound oxycodone.

Another embodiment provides a method of reducing drug toxicity comprising providing a patient with oxycodone which has been covalently bound to a chemical moiety wherein the chemical moiety increases the rate of clearance of a pharmacologically active oxycodone when given at doses exceeding those within the therapeutic range of oxycodone.

Another embodiment provides a method of reducing drug toxicity comprising providing a patient with oxycodone which has been covalently bound to a chemical moiety wherein the chemical moiety provides a serum release curve which does not increase above the oxycodone's toxicity level when given at doses exceeding those within the therapeutic range for the unbound oxycodone.

Another embodiment provides a method of reducing bioavailability of a oxycodone comprising providing oxycodone covalently bound to a chemical moiety wherein the bound oxycodone maintains a steady-state serum release curve which provides a therapeutically effective bioavailability but prevents spiking or increase blood serum concentrations compared to unbound oxycodone when given at doses exceeding those within the therapeutic range for the unbound oxycodone. Another embodiment provides a method of preventing a $C_{max}$ spike for oxycodone while still providing a therapeutically effective bioavailability curve comprising providing oxycodone which has been covalently bound to a chemical moiety. In another embodiment, methods of the invention provide bioavailability curves similar to those of FIGS. 1–45 when tested in rats.

Another embodiment provides a method for preventing a toxic release profile in a patient comprising administering to a patient oxycodone covalently bound to a chemical moiety wherein said bound oxycodone maintains a steady-state serum release curve which provides a therapeutically effective bioavailability but prevents spiking or increase blood serum concentrations compared to unbound oxycodone.

Another embodiment of the invention is a method for reducing or preventing abuse of a pharmaceutical composition, comprising providing, administering, or prescribing said composition to a human in need thereof, wherein said composition comprises a chemical moiety covalently attached to oxycodone such that the pharmacological activity of oxycodone is substantially decreased when the composition is used in a manner inconsistent with the manufacturer's instructions. Another embodiment of the invention is a method for reducing or preventing abuse of a pharmaceutical composition, comprising consuming said composition, wherein said composition comprises a chemical moiety covalently attached to oxycodone such that the pharmacological activity of oxycodone is substantially decreased when the composition is used in a manner inconsistent with the manufacturer's instructions.

Another embodiment of the invention is a method of preventing overdose of a pharmaceutical composition, comprising providing, administering, or prescribing said pharmaceutical composition to a human in need thereof, wherein said composition comprises a chemical moiety covalently attached to oxycodone in a manner that substantially decreases the potential of overdose from oxycodone. Another embodiment of the invention is a method of preventing overdose of a pharmaceutical composition, comprising consuming said pharmaceutical composition, wherein said composition comprises a chemical moiety covalently attached to oxycodone in a manner that substantially decreases the potential of overdose from oxycodone.

Another embodiment of the invention is a method for reducing or preventing the euphoric effect of a pharmaceutical composition, comprising providing, administering, or prescribing said composition to a human in need thereof, wherein said composition comprises a chemical moiety covalently attached to oxycodone such that the pharmacological activity of oxycodone is substantially decreased when the composition is used in a manner inconsistent with the manufacturer's instructions. Another embodiment of the invention is a method for reducing or preventing the euphoric effect of a pharmaceutical composition, comprising consuming said composition, wherein said composition comprises a chemical moiety covalently attached to oxycodone such that the pharmacological activity of oxycodone is substantially decreased when the composition is used in a manner inconsistent with the manufacturer's instructions.

Another embodiment of the invention is any of the preceding methods wherein said pharmaceutical composition is adapted for oral administration, and wherein said oxycodone is resistant to release from said chemical moiety when the composition is administered parenterally, such as intranasally or intravenously. Preferably, said oxycodone may be released from said chemical moiety in the presence of acid and/or enzymes present in the stomach, intestinal tract, or blood serum. Optionally, said composition may be in the form of a tablet, capsule, oral solution, or oral suspension.

Another embodiment of the invention is any of the preceding methods wherein said chemical moiety is an amino acid, oligopeptide, polypeptide, carbohydrate, glycopeptide, nucleic acid, or vitamin. Preferably, said chemical moiety is an amino acid, oligopeptide, or polypeptide. Where the chemical moiety is a polypeptide, preferably said polypeptide comprises fewer than 70 amino acids, fewer than 50 amino acids, fewer than 10 amino acids, or fewer than 6 amino acids.

Another embodiment of the invention is any of the preceding methods wherein said covalent attachment comprises an ester or carbonate bond. Another embodiment of the invention is any of the preceding methods wherein said oxycodone covalently attaches to a chemical moiety through a ketone and/or hydroxyl in a pharmaceutically acceptable oral dosage form.

Another embodiment of the invention is any of the preceding methods wherein said composition yields a therapeutic effect without substantial euphoria. Preferably, said oxycodone provides a therapeutically bioequivalent AUC when compared to active agent alone but does provide a $C_{max}$ which results in euphoria.

Another embodiment of the invention is a method for reducing or preventing abuse of a pharmaceutical composition, comprising orally administering said composition to a human in need thereof, wherein said composition comprises an amino acid or peptide covalently attached to oxycodone such that the pharmacological activity of oxycodone is substantially decreased when the composition is used in a manner inconsistent with the manufacturer's instructions.

Another embodiment is a method of preventing overdose of a pharmaceutical composition, comprising orally administering said pharmaceutical composition to a human in need thereof, wherein said composition comprises an amino acid or peptide covalently attached to oxycodone in a manner that substantially decreases the potential of oxycodone to result in overdose.

Another embodiment is a method for reducing or preventing the euphoric effect of a pharmaceutical composition, comprising orally administering said composition to a human in need thereof, wherein said composition comprises an amino acid or peptide covalently attached to oxycodone such that the pharmacological activity of oxycodone is substantially decreased when the composition is used in a manner inconsistent with the manufacturer's instructions.

For each of the recited methods of the invention the following properties may be achieved through bonding oxycodone to the chemical moiety. In one embodiment, the toxicity of the compound may be substantially lower than that of the oxycodone when delivered in its unbound state or as a salt thereof. In another embodiment, the possibility of overdose by oral administration is reduced or eliminated. In another embodiment, the possibility of overdose by intranasal administration is reduced or eliminated. In another embodiment, the possibility of overdose by injection administration is reduced or eliminated.

Another embodiment of the invention provides methods of treating various diseases or conditions comprising administering compounds or compositions of the invention which further comprise commonly prescribed active agents for the respective illness or diseases wherein the oxycodone is covalently attached to a chemical moiety. For instance, one embodiment of the invention comprises a method of treating narcotic addiction comprising administering to a patient compounds or compositions of the invention. Another embodiment of the invention provides a method of providing analgesia comprising administering to a patient compounds or compositions of the invention.

In order to facilitate a more complete understanding of the invention, Examples are provided below. However, the scope of the invention is not limited to specific embodiments disclosed in these Examples, which are for purposes of illustration only.

EXAMPLES

The invention is illustrated by pharmacokinetic studies with oxycodone that have been covalently modified by attachment to various moieties such as an individual amino acid, specific short chained amino acid sequences such as di-, tri-, and pentapeptides, or carbohydrates such as ribose, etc. Studies include pharmacokinetic evaluations of the various drug conjugates administered by the oral, intranasal, and intravenous routes. Collectively the compounds demonstrate that active agents may be modified by covalent attachment to various moieties and retain their therapeutic value at normal doses while preventing potential overdose by oral administration and prevention of abuse through intranasal and intravenous administration.

Examples 1 through 35

Oxycodone

The Examples illustrate the applicability of attaching various moieties to oxycodone to reduce the potential for overdose while maintaining therapeutic value. The invention is illustrated by pharmacokinetic studies with various peptide opioid conjugates. Examples 1 through 35 illustrate the compounds and compositions for reducing the potential for overdose and abuse while maintaining therapeutic value wherein the the active agent oxycodone (OC) is covalently attached to a chemical moiety. The compound which is di-substituted at the 6 and 14 position of oxycodone is termed [PPL]$_2$-OC.

Oral, intranasal, and intravenous bioavailability studies of oxycodone and oxycodone conjugates were conducted in male Sprague-Dawley rats. Doses of oxycodone hydrochloride and oxycodone conjugates containing equivalent amounts of oxycodone were administered in deionized water. Oral administration was in 0.5 ml by gavage needle. Intranasal doses were administered by placing 20 microliters into the nasal flares of rats anesthetized with isoflurane. Intravenous administration was in 0.1 ml by tail vein injection. Plasma was collected by retroorbital sinus puncture under isoflurane anesthesia. Oxycodone and oxymorphone (major active metabolite) concentrations were determined by LC/MS/MS.

The below examples are illustrative only and [PPL]$_2$-OC is not meant to be limiting. As such, synthesis and attachment of oxycodone may be accomplished for instance view the following exemplary methods.

OXYCODONE SYNTHETIC EXAMPLES

Example 1

Synthesis of [Boc-X]$_2$-Oxycodone

To a solution of oxycodone free base (2.04 g, 6.47 mmol) in THF (~35 ml) was added LiN(TMS)$_2$ (19.41 ml, 19.41 mmol) and stirred for ~30 mins. To this was added solid Boc-X-OSu (X=amino acid, 21 mmol) at one time and the reaction mixture was stirred at room temperature overnight. The solution was neutralized with 1N HCl and the THF was removed under reduced pressure. The residue was diluted with EtOAc (200 mL), satd. NaHCO$_3$ (150 mL) was added and stirred for 1 h. EtOAc part was washed with NaHCO3 and brine. Dried over Na$_2$SO$_4$ and evaporated to dryness. Compound was obtained by purification over silica gel column (30% EtOAc/Hexane).

Deprotection of [Boc-X]$_2$-Oxycodone:

General method of deprotection: The above compound was reacted with 4N HCl/dioxane (25 mL/gm) at room temperature for 4 h. Solvent was evaporated and dried over vacuum to give X$_2$-Oxycodone.3HCl.

Examples:
1. [Val]$_2$-Oxycodone
2. [Ile]$_2$-Oxycodone
3. [Leu]$_2$-Oxycodone
4. [Lys]$_2$-Oxycodone
5. [Phe]$_2$-Oxycodone
6. [Glu]$_2$-Oxycodone

Example 2

Synthesis of [Boc-Z-Y-X]$_2$-Oxycodone [X, Y and Z are Amino Acids]

To a solution of X$_2$-Oxycodone.3HCl (1 mmol) in DMF (15–20 mL) were added NMM (10–12 eqv) and Boc-Z-Y-OSu (2.6 eqv). The reaction mixture was stirred at RT overnight. Solvent was evaporated under reduced pressure. To the residue was added satd. NaHCO$_3$ (~30 mL) and stir for 1–2 h. The white/pale yellow residue was filtered, thoroughly washed with water and dried in the vacuum oven at room temperature.

Deprotection of [Boc-X-Y-Z]$_2$-Oxycodone:

Deprotection is same as general method mentioned above. For 100–200 mg of tripeptide derivative 10–15 ml 4N HCl/dioxane is used. Deprotection is done overnight to give [X-Y-Z]$_2$-Oxycodone.3HCl.

Deprotection of Tripeptide Derivatives Containing Threonine and Serine:

First the tripeptide derivatives are dissolved 95% TFA (5% water) and stirred for 4 h at room temperature. Solvent is evaporated, the residue is co-evaporated with toluene twice and dried over vacuum. 4N HCl/dioxane is added and stirred overnight. Residue was evaporated to dryness and dried over vacuum.

Examples:
1. [Glu-Asp-Val]$_2$-Oxycodone
2. [fle-Tyr-Val]$_2$-Oxycodone
3. [Tyr-Pro-Val]$_2$-Oxycodone
4. [Gly-Leu-Val]$_2$-Oxycodone
5. [Phe-Val-Val]$_2$-Oxycodone
6. [Ser-Thr-Val]$_2$-Oxvcodone
7. [Lys-Ser-Val]$_2$-Oxycodone

Example 3

Synthesis of [Boc-X]-O$^6$-Oxycodone

To a solution of oxycodone (10 mmol) in THF (50 mL) was added LiN(TMS)$_2$ (10.5 mmol) at 0° C. After 20 mins was added Boc-X-OSu (11 mmol) and then the reaction mixture was stirred at room temperature overnight. The solution was cooled down to 0° C. and neutralized with 1N HCl. The organic solvent was evaporated and to the residue were added EtOAc (200 mL) and saturated aq. NaHCO$_3$ (150 mL) and stirred for 1 h. The EtOAc portion was washed with water, brine, dried over Na$_2$SO$_4$ and evaporated to dryness. The residue was purified over silica gel (70% EtOAc-Hexane) to give the title compound.

Deprotection of Boc-X-O⁶-Oxycodone:

A solution of [Boc-X]-Oxycodone in 4N HCl/dioxane (10 ml/mmol) was stirred at room temperature 4 h. Solvent was evaporated under reduced pressure and the residue was dried under vacuum to give X-O⁶-Oxycodone.2HCl.

Examples:
1. Val-Oxycodone
2. Ile-Oxycodone
3. Leu-Oxycodone

Example 4

Synthesis of Boc-Z-Y-X-O⁶-Oxycodone

To a solution of X-O⁶-Oxycodone.2HCl (1 mmol) in DMF were added NMM (10 mmol) and Boc-Z-Y-OSu (1.2 mmol). The reaction mixture was stirred at room temperature overnight. Solvent was evaporated to the residue was added saturated $NaHCO_3$ solution and stirred for 1 h. The precipitate was filtered, thoroughly washed with water and dried to give the title compound.

Deprotection of Boc-Z-Y-X-O⁶-Oxycodone:

Deprotection is same as general method mentioned above to give Z-Y-X-O⁶-Oxycodone.2HCl.

Examples:
1. Pro-Glu-Val-Oxycodone
2. Glu-Leu-Val-Oxycodone
3. Glu-Tyr-Val-Oxycodone

Example 5

Synthesis of Boc-X-O⁶-Oxycodone-O¹⁴-Ac

To a solution of [Boc-X]-O⁶-Oxycodone (1 mmol) in pyridine (15 mL) were added DMAP (75 mg), triethyl amine (1.5 mmol) and $Ac_2O$ (8 mmol). The reaction mixture was heated at 65° C. for 3 days. The dark brown solution was cooled down to room temperature and MeOH (5 mL) was added and stirred for 1 h. The solvent was evaporated, co-evaporated with toluene. The residue was taken in EtOAc (50 mL), washed with satd. $NaHCO_3$, brine, dried over $Na_2SO_4$ and evaporated to dryness. The residue was purified over silila gel to give the title compound.

Example 6

Synthesis of Boc-X-O⁶-Oxycodone-O¹⁴-$CO_2$Et

To a solution of [Boc-X]-O⁶-Oxycodone (1 mmol) in THF (10 mL) was added $LiN(TMS)_2$ (1.05 mmol) at 0° C. After 20 mins, ethyl chloroformate (1.1 mmol) was added and reaction mixture was slowly brought to room temperature and stirred at room temperature for 1 h. The solution was poured into 2% aqueous acetic acid (ice cold) and extracted with EtOAc. The EtOAc part was washed with water, aq. $NaHCO_3$, brine, dried over $Na_2SO_4$ and evaporated to dryness. The residue was purified over silica gel to give the title compound.

Deprotection of Boc-X-O⁶-Oxycodone-O¹⁴—R(R=Ac, $CO_2$Et):

Deprotection is same as general method mentioned above to give X—O⁶-Oxycodone-O¹⁴—R.2HCl (R=Ac, $CO_2$Et).

Examples:
1. (Val)-Oxycodone-($CO_2$Et)
2. (Val)-Oxycodone-(OAc)

Example 7

Synthesis of Boc-Z-Y-X-O⁶-Oxycodone-O¹⁴—R (R=Ac, $CO_2$Et)

To a solution of X-O⁶-Oxycodone-O¹⁴—R.2HCl (1 mmol, R=Ac, $CO_2$Et) in DMF were added NMM (10 mmol) and Boc-Z-Y-OSu (1.2 mmol). The reaction mixture was stirred at room temperature overnight. Solvent was evaporated to the residue was added saturated $NaHCO_3$ solution and stirred for 1 h. The precipitate was filtered, thoroughly washed with water and dried to give the title compound.

Deprotection of Boc-Z-Y-X-O⁶-Oxycodone-O¹⁴—R(R=Ac, $CO_2$Et):

Deprotection is same as general method mentioned above. Deprotection is done overnight to give Z-Y-X-O⁶-Oxycodone-O¹⁴—R.2HCl.

Examples:
1. (Ile-Tyr-Val)-Oxycodone-($CO_2$Et)
2. (Ile-Tyr-Val)-Oxycodone-(OAc)

Example 8

Synthesis of Boc-X-O⁶-Oxycodone-O¹⁴-Y-Boc

To a solution of Boc-X-Oxycodone (1 mmol) in THF (10 μL) was added $LiN(TMS)_2$ (1.1 mmol) at 0° C. and the solution was stirred for 30 mins then Boc-Y-OSu (1.25 mmol) was added. The reaction mixture was stirred at room temperature overnight. The solution was cooled down to 0° C., neutralized with 1N HCl and the organic part was evaporated. To the residue were added EtOAc (50 mL) and satd. $NaHCO_3$ (50 ml), stirred for 1 h. The organic part was washed with water, brine, dried over $Na_2SO_4$ and evaporated to dryness. The residue was purified over silica gel to give the title compound.

Deprotection of Boc-X-O⁶-Oxycodone-O¹⁴-Y-Boc:

Boc-X-O⁶-Oxycodone-O¹⁴-Y-Boc was deprotected following the general method for deprotection mentioned above to give X-O⁶-Oxycodone-O¹⁴-Y.3HCl.

Example:
Val-Oxycodone-Gly

Example 9

Synthesis of Boc-A-B-X-O⁶-Oxycodone-O¹⁴-Y-B-A-Boc (A, B, X, Y=amino acids)

To a solution of X-O⁶-Oxycodone-O¹⁴-Y.3HCl (1 mmol) and NMM (10 mmol) in DMF (10 mL) was added Boc-A-B-OSu (2.5 mmol) and the reaction mixture was stirred at room temperature overnight. Solvent was evaporated under reduced pressure and to the residue satd. $NaHCO_3$ (15 mL) was added and stirred for 1 h. The precipitate was filtered off and the residue was washed thoroughly with water and dried.

Deprotection of Boc-A-B-X-O⁶-Oxycodone-O¹⁴-Y-B-A-Boc:

Deprotection is same as general method mentioned above. Deprotection is done overnight to give A-B-X-O⁶-Oxycodone-O¹⁴-Y-B-A.3HCl.

Examples:
1. (Ile-Tyr-Val)-Oxycodone-(Gly-Tyr-Ile)
2. (Leu-Tyr-Val)-Oxycodone-(Gly-Tyr-Leu)

Example 10

Synthesis of Boc-X-O$^6$-Oxycodone-O$^{14}$-Y-Cbz

To a solution of Boc-X-Oxycodone (1 mmol) in THF (10 mL) was added LiN(TMS)$_2$ (1.1 mmol) at 0° C. and the solution was stirred for 30 mins then Cbz-Y-OSu (1.25 mmol) was added. The reaction mixture was stirred at room temperature overnight. The solution was cooled down to 0° C., neutralized with 1N HCl and the organic part was evaporated. To the residue were added EtOAc (50 mL) and satd. NaHCO$_3$ (50 ml), stirred for 1 h. The organic part was washed with water, brine, dried over Na$_2$SO$_4$ and evaporated to dryness. The residue was purified over silica gel to give the title compound.

Deprotection of Boc-X-O$^6$-Oxycodone-O$^{14}$-Y-Cbz.2HCl:

Boc-X-O$^6$-Oxycodone-O$^{14}$-Y-Cbz was deprotected following the general method for deprotection mentioned above to give X-O$^6$-Oxycodone-O$^{14}$-Y-Cbz.2HCl.

Example 11

Synthesis of Boc-A-B-X-O$^6$-Oxycodone-O$^{14}$-Y-Cbz

To a solution of X-O$^6$-Oxycodone-O$^{14}$-Y-Cbz.2HCl (1 mmol) and NMM (10 mmol) in DMF (10 mL) was added Boc-A-B-OSu (1.1 mmol) and the reaction mixture was stirred at room temperature overnight. Solvent was evaporated under reduced pressure and to the residue satd. NaHCO$_3$ (20 mL) was added and stirred vigorously for 2–3 h. The precipitate was filtered off and the residue was washed thoroughly with water and dried.

Example 12

Synthesis of Boc-A-B-X-O$^6$-Oxycodone-O$^{14}$-Y-NH2

To a suspension of Boc-A-B-X-O$^6$-Oxycodone-O$^{14}$-Y-Cbz and Pd/C (25 Wt %) in EtOH (20 ml/gm) and cyclohexene (10 ml/gm) was heated under reflux for 30 mins. The reaction mixture was cooled down to room temperature and filtered. The filtrate was evaporated to dryness to give the title compound.

Example 13

Synthesis of Boc-A-B-X-O$^6$-Oxycodone-O$^{14}$-Y-C-D-Boc (A, B, C, D, X, Y=amino acids)

To a solution of Boc-A-B-X-O$^6$-Oxycodone-O$^{14}$-Y-NH$_2$ (1 mmol) in DMF (10 mL) were added NMM (5 mmol) and Boc-D-C-OSu (1.1 mmol) and the reaction mixture was stirred at room temperature overnight. Solvent was evaporated under reduced pressure and to the residue satd. NaHCO$_3$ was added and stirred for 1 h. The white precipitate was filtered, washed with water and dried.

Deprotection of Boc-A-B-X-O$^6$-Oxycodone-O$^{14}$-Y-C-D-Boc:

Deprotection is same as general method mentioned above. Deprotection is done overnight to give A-B-X-O$^6$-Oxycodone-O$^{14}$-Y-C-D.3HCl.

Examples:
1. (Ile-Tyr-Val)-Oxycodone-(Val-Glu-Gly)
2. (Leu-Tyr-Val)-Oxycodone-(Val-Glu-Gly)

Mono-Substituted Single Amino Acids (Enol Ester)

FIG. 1 depicts oxycodone.

Example 14

Phe-Oxycodone

To a solution of oxycodone-freebase (1.0 eq) in tetrahydrofuran (THF) (10 ml/mmol) was added LiN(TMS)$_2$ (3.5 eq). After 5 minutes, Boc-Phe-OSu (3.5 eq) was added. The reaction was stirred at ambient temperatures for 18 hours, quenched with water and solvents removed. Crude protected product was purified using reverse-phase HPLC. Deprotection occurred with 4N HCl in dioxane (20 ml/mmol) to obtain Phe-Oxycodone.

Example 15

Synthesis of Ile-Oxycodone

Ile-Oxycodone was prepared in a similar manner to Example 14 except Boc-Ile-OSu was used as the amino acid starting material.

Mono-Substituted Tripeptides (Enol Ester)

Example 16

Pro$_2$-Leu-Oxycodone

To a solution of Leu-Oxycodone (1.0 eq) in dimethylformamide (10 mil/0.1 mmol) was added 4-methylmorpholine (10 eq) and Boc-Pro-Pro-OSu (2 eq). The reaction was stirred at ambient temperatures for 18 hours, quenched with water, and solvents removed. Crude protected product was purified using reverse phase HPLC. Deprotection occurred using 4N HCl in dioxane (20 ml/mmol) to obtain Pro$_2$-Leu-Oxycodone.

Example 17

Synthesis of Pro$_2$-Ile-Oxycodone

Pro$_2$-Ile-Oxycodone was prepared in a similar manner to Example 16 except Ile-Oxycodone was used as the conjugated starting material.

Example 18

Oxycodone Disubstituted Tripeptides

General Synthetic Procedure

Synthesis of [Boc-Val]$_2$-OC:

To a solution of OC (2.04 g, 6.47 mmol) in tetrahydrofuran (THF) (~35 ml) was added LiN(TMS)$_2$ (19.41 ml, 19.41 mmol) and stirred for ~30 mins. To this was added solid Boc-Val-OSu (6.72 g, 21 mmol) at one time and the reaction mixture was stirred at room temperature overnight. The solution was neutralized with 1N HCl and the THF was removed under reduced pressure. The residue was diluted with ethyl acetate (EtOAc) (200 mL), satd. NaHCO$_3$ (150 mL) was added and stirred for 1 h. EtOAc part was washed with NaHCO$_3$ and brine. Dried over Na$_2$SO$_4$ and evaporated to dryness. Crude product was purified with either silica gel column. (30% EtOAc/Hexane).

Deprotection: For the deprotection of 2.5 g of [Boc-Val]$_2$-OC, 75–80 mL of 4N HCl/dioxane was used. Reaction was complete within 3–4 hours. Evaporate dioxane and dry over vacuum at lease for 24 h.

Coupling: To a solution of Val$_2$-OC.3HCl (250 mg, 0.4 mmol) in DMF (10–12 ml) were added NMM (10–12 eqv)

and Boc-X-Y-OSu (2.6 eqv). The reaction mixture was stirred at RT overnight. Solvents were evaporated under reduced pressure. To the residue was added satd. NaHCO$_3$ (~30 mL) and stirred for 1 h. The white/pale yellow residue was filtered, thoroughly washed with water and dried in the vacuum oven at RT.

Deprotection: Deprotection was same as above method. For 100–200 mg of tripeptide derivative 10–15 ml 4N HCl/dioxane was used. Deprotection lasts 18 hours.

Deprotection of tripeptide derivatives containing Threonine and Serine: Tripeptide derivatives were dissolved in 95% TFA (5% water) and stirred for 4 h at room temperature. Solvent was evaporated and the residue was co-evaporated with toluene twice and dried over vacuum. 4N HCl/dioxane was added and stirred overnight. Product was evaporated to dryness and dried over vacuum.

Example 19

Oxycodone Branched Amino Acid Chains

General Synthesis

Figure 2:
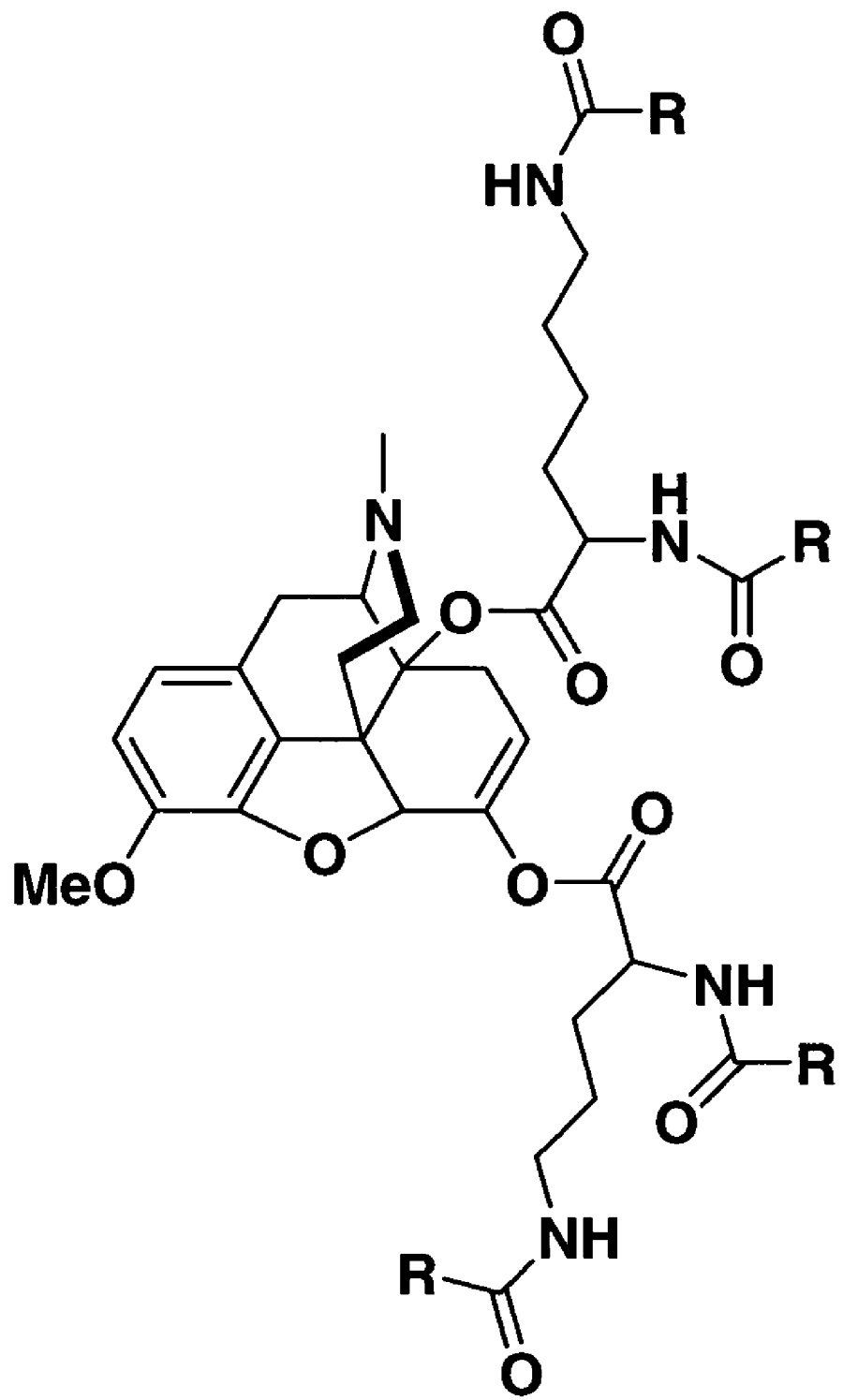
FIG. 2 depicts oxycodone with lysine branched peptides.

FIG. 2 depicts oxycodone with lysine branched peptides.

Example 20

[Lys]$_2$-Oxycodone

Method was similar to other single amino acid derivatives except Boc-Lys(Boc)-OSu was used as the amino acid starting material.

Example 21

XX-Lys(XX)-Oxycodone

To a solution of [Lys]$_2$-Oxycodone (1.0 eq) in dimethylformamide (1 ml/mmol) was added 4-methylmorpholine (5.5 eq) followed by Boc-XX$_2$-OSu (4.1 eq). Reaction was stirred at ambient temperature for $_{24}$ hours. Solvents were removed and crude product was purified by reverse phase HPLC.

Example 22

Synthesis of [Gly$_2$-Lys(-Gly$_2$)[SEQ ID NO: 7]]$_2$-Oxycodone

[Gly$_2$-Lys(-Gly$_2$)[SEQ ID NO: 7]]$_2$-Oxycodone was prepared in a manner similar to Example 21 except Boc-Gly$_2$-OSu was used as the amino acid starting material.

Example 23

Oxycodone D-Amino Acids

General Synthesis

Disubstituted D-amino acid tripeptides were prepared in a manner similar to disubstituted tripeptide conjugates except the amino acid starting material used the unnatural D-amino acids.

[(l)-Lys-(d)-Lys-Leu]$_2$-Oxycodone

To a solution of [Leu]$_2$-Oxycodone (1.0 eq) in dimethylformamide (1 ml/mmol) was added 4-methylmorpholine (10 eq) followed by Boc-(l)-Lys(Boc)-(d)-Lys(Boc)-OSu (3 eq). Reaction was stirred at ambient temperature for 24 hours. Solvents were removed and crude product was purified by reverse phase HPLC.

Example 24

Synthetic Amino Acids

Synthesis of [Boc-Z]$_2$-OC [where Z can equal cyclohexylalanine (Cha), dipropylglycine (Dpg), tert-Leucine (Tle) or any other synthetic amino acid].

To a solution of OC (6.47 mmol) in THF was added LiN(TMS)$_2$ (19.41 mmol) and stirred for ~30 mins. To this was added solid Boc-Z-OSu (21 mmol) at one time and the reaction mixture was stirred at room temperature overnight. The solution was neutralized with 1N HCl and the THF was removed under reduced pressure. The residue was diluted with ethyl acetate (EtOAc), satd. NaHCO$_3$ was added and stirred for 1 h. EtOAc part was washed with NaHCO$_3$ and brine. Dried over Na$_2$SO$_4$ and evaporated to dryness. Crude product was purified with either silica gel column. (30% EtOAc/Hexane).

Example 25

Non-Standard Amino Acids (Naturally Occurring, Not the Standard 20)

Synthesis of [Boc-N]$_2$-OC [where N can equal norleucine (Nle), homophenylalanine (hPhe) or any other non-standard amino acid].

To a solution of OC (6.47 mmol) in THF was added LiN(TMS)$_2$ (19.41 mmol) and stirred for ~30 mins. To this was added solid Boc-N-OSu (21 mmol) at one time and the reaction mixture was stirred at room temperature overnight. The solution was neutralized with 1N HCl and the THF was removed under reduced pressure. The residue was diluted with ethyl acetate (EtOAc), satd. NaHCO$_3$ was added and stirred for 1 h. EtOAc part was washed with NaHCO$_3$ and brine. Dried over Na$_2$SO$_4$ and evaporated to dryness. Crude product was purified with either silica gel column. (30% EtOAc/Hexane).

Other Oxycodone Conjugates

Example 26

Glycopeptides

Using galactose and a number of tripeptides, glycopeptides will be produced.

Initial Glycopeptides to be Produced
1. [Gal-Gly$_2$-Ile]$_2$-OC
2. [Gal-Pro$_2$-Ile]$_2$-OC
3. [Gal-Gly$_2$-Leu]$_2$-OC
4. [Gal-Pro$_2$-Leu]$_2$-OC

Example 27

Glycosylation of Oxycodone

Figure 3:
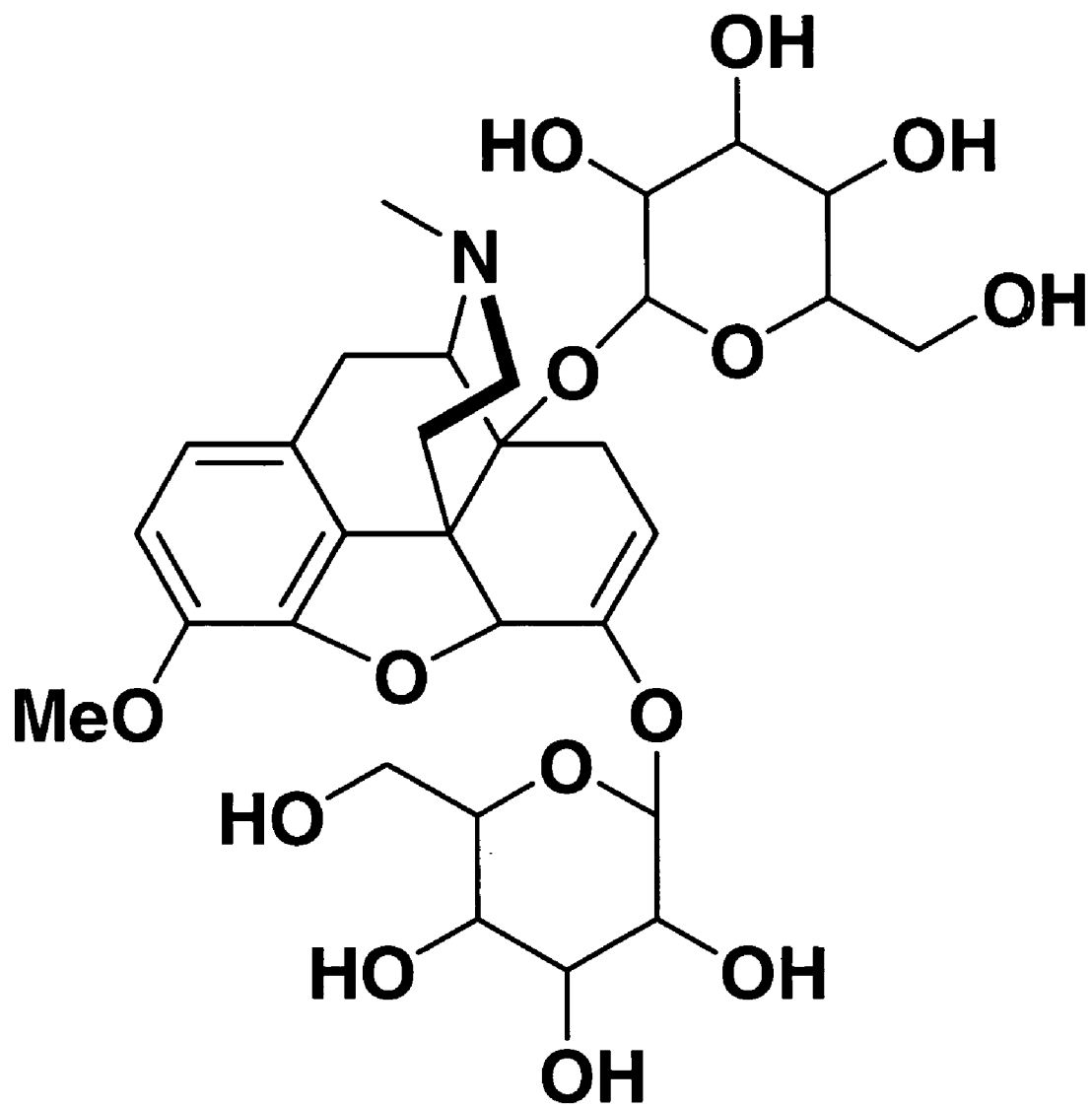
FIG. 3 depicts a glycosylated oxycodone.

FIG. 3 depicts a glycosylated oxycodone.

A glycosylation reaction of Oxycodone with a carbohydrate will be attempted. The linkage produced would essentially be an enol ether which are difficult to cleave chemically yet glycosidic bonds are commonly broken down in vivo. Either site or both may be conjugated.

Example 28

Formation of an Enol Ether with Serine

Figure 4:
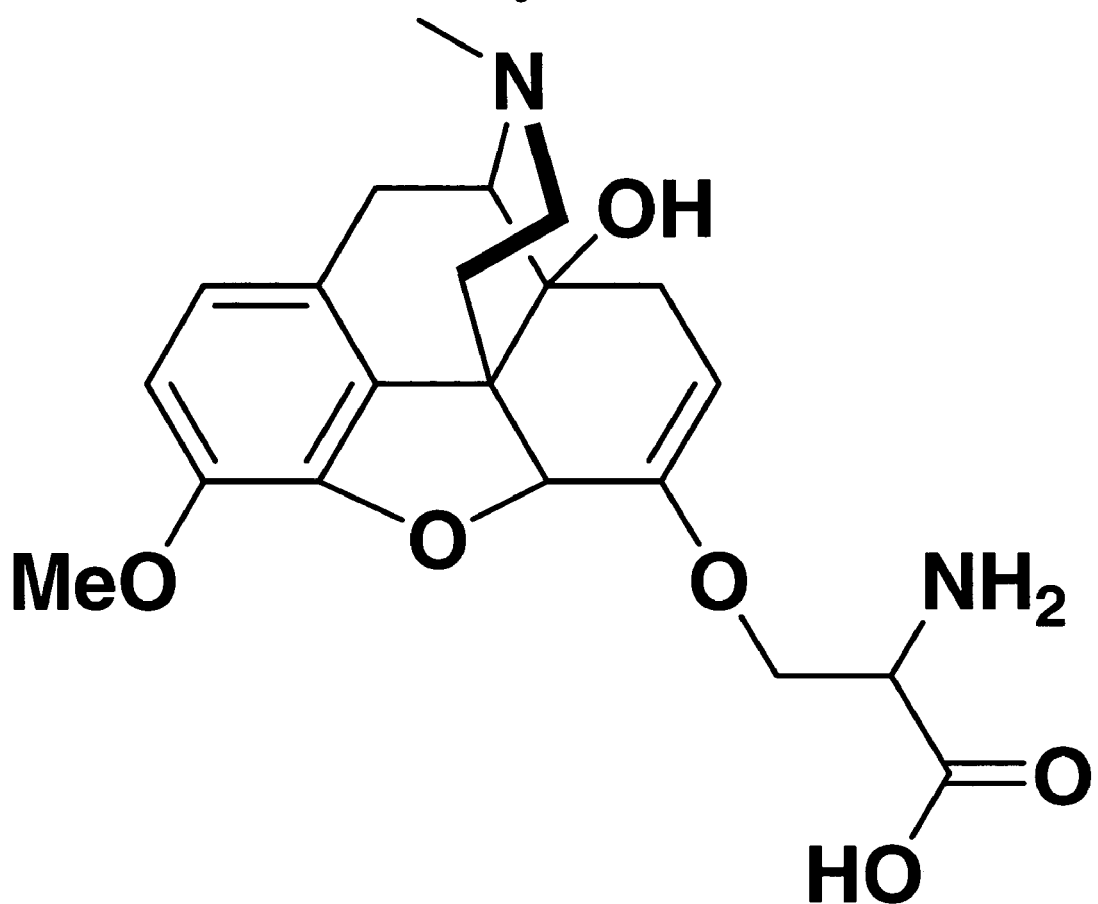
FIG. 4 depicts formation of an enol ether with serine.

FIG. 4 depicts formation of an enol ether with serine.

Using serine and OC, an enol ether conjugate will be produced. This conjugate would be stable to most hydrolysis conditions. Only the enol ether would be formed in this reaction.

Example 29

Vitamins

Figure 5:
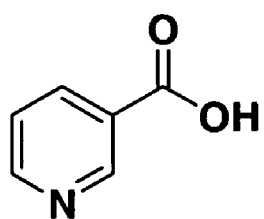
FIG. 5 depicts niacin and biotin.
Figure 5:
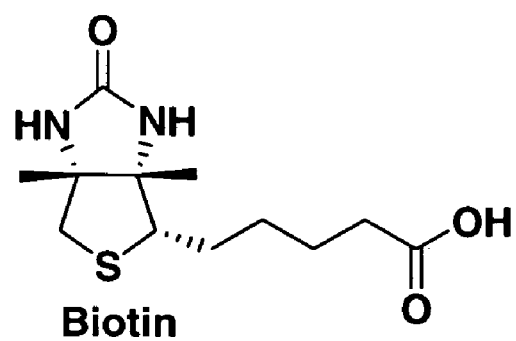
Figure 6:
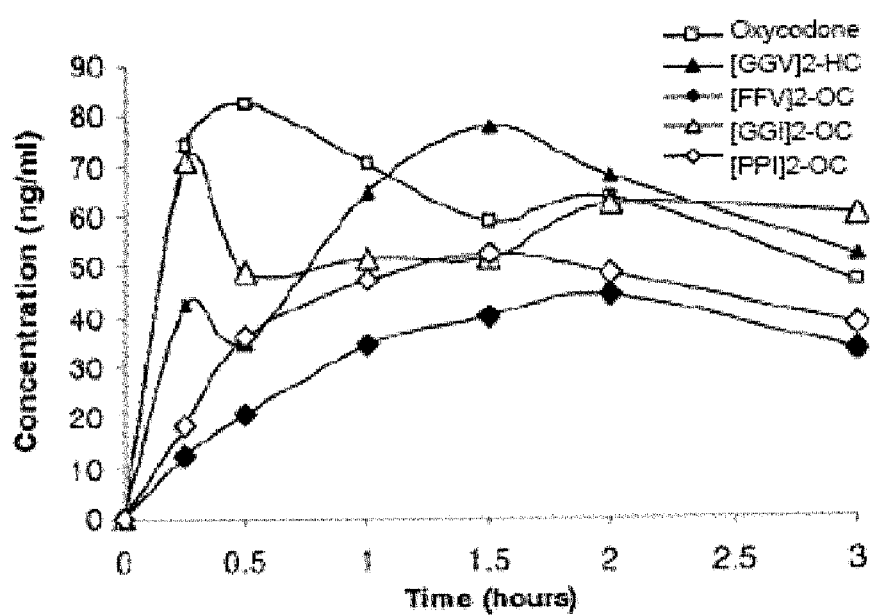
FIG. 6 Oral bioavailability of abuse-resistant oxycodone disubstituted tripeptide conjugates, measured as free oxycodone.
Figure 7:
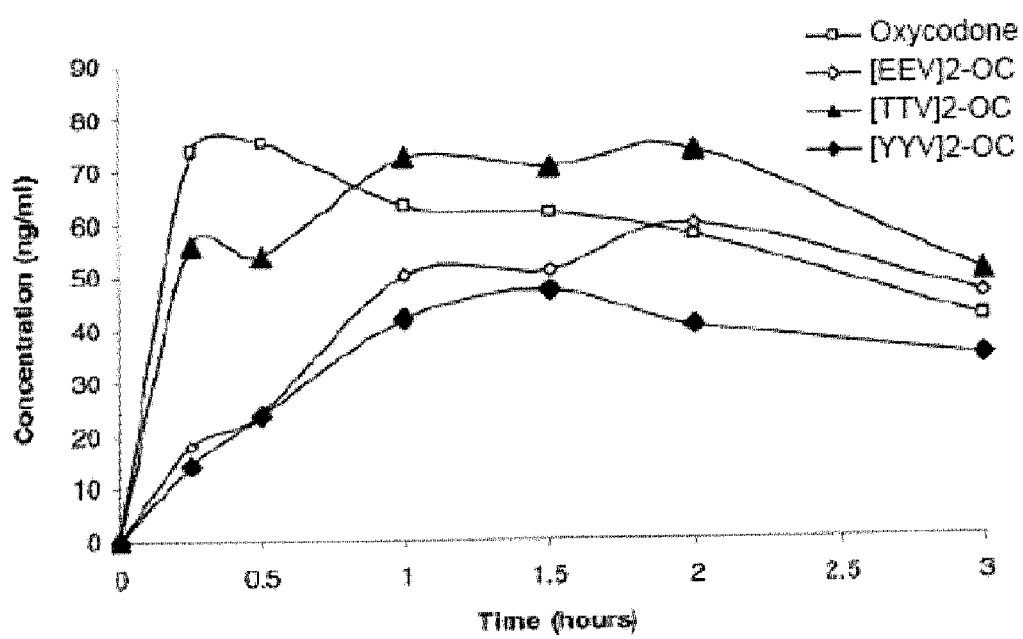
FIG. 7 Oral bioavailability of abuse-resistant oxycodone disubstituted tripeptide conjugates, measured as free oxycodone.
Figure 8:
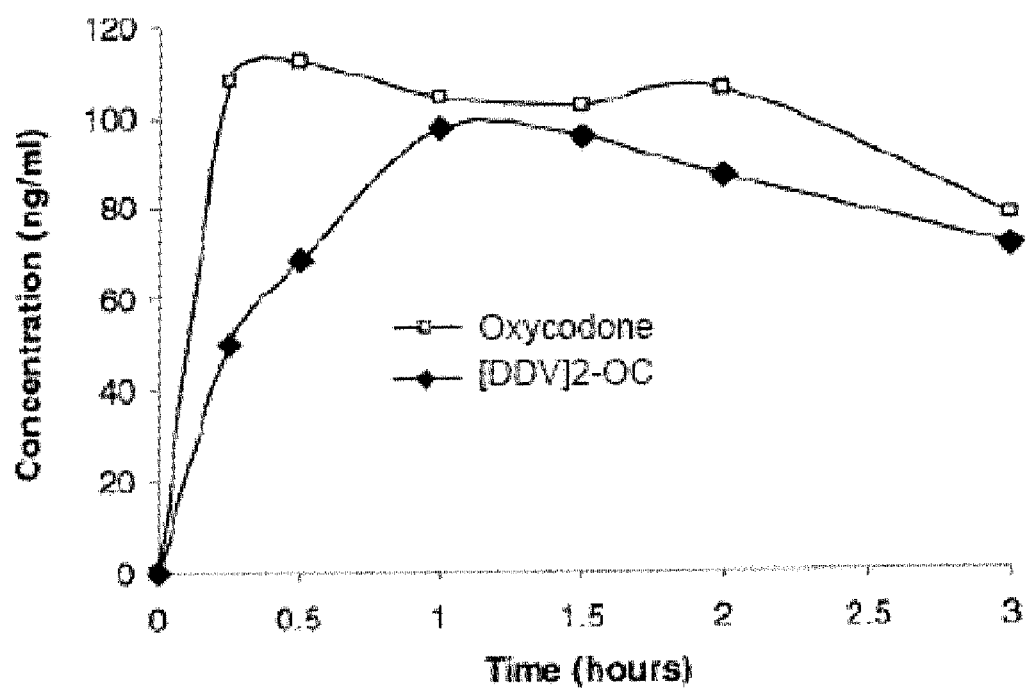
FIG. 8 Oral bioavailability of abuse-resistant oxycodone disubstituted tripeptide conjugates, measured as free oxycodone.
Figure 9:
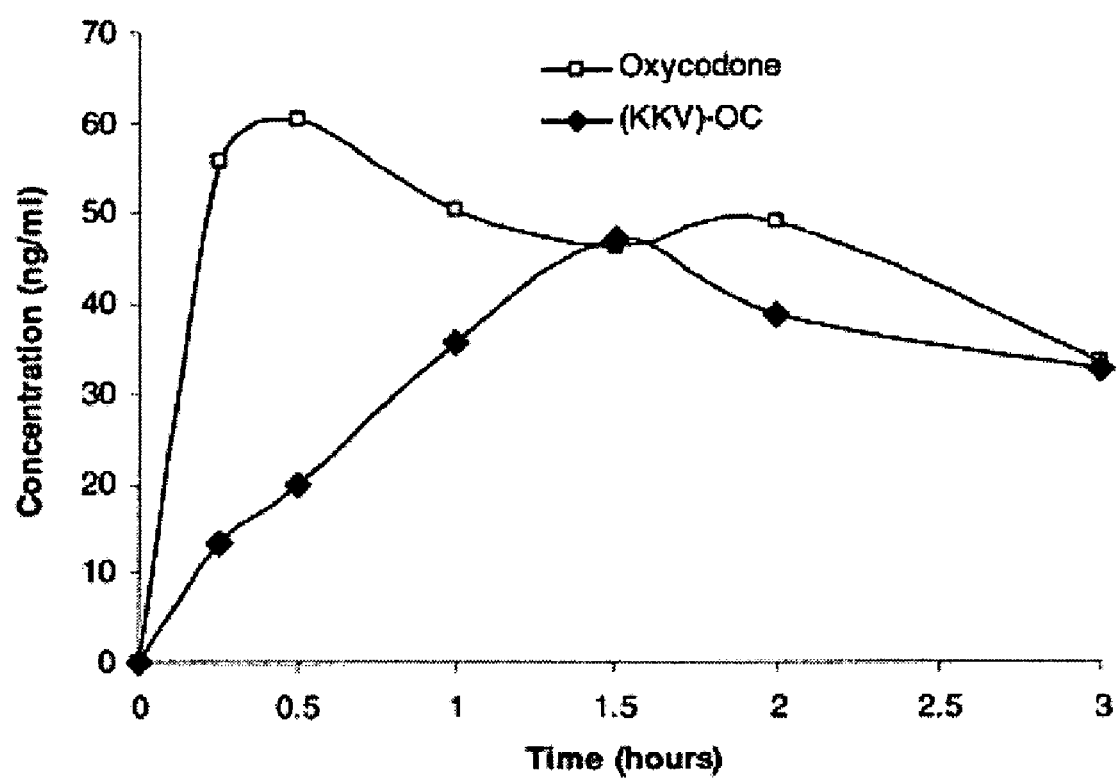
FIG. 9 Oral bioavailability of abuse-resistant oxycodone disubstituted tripeptide conjugates, measured as free oxycodone.
Figure 10:
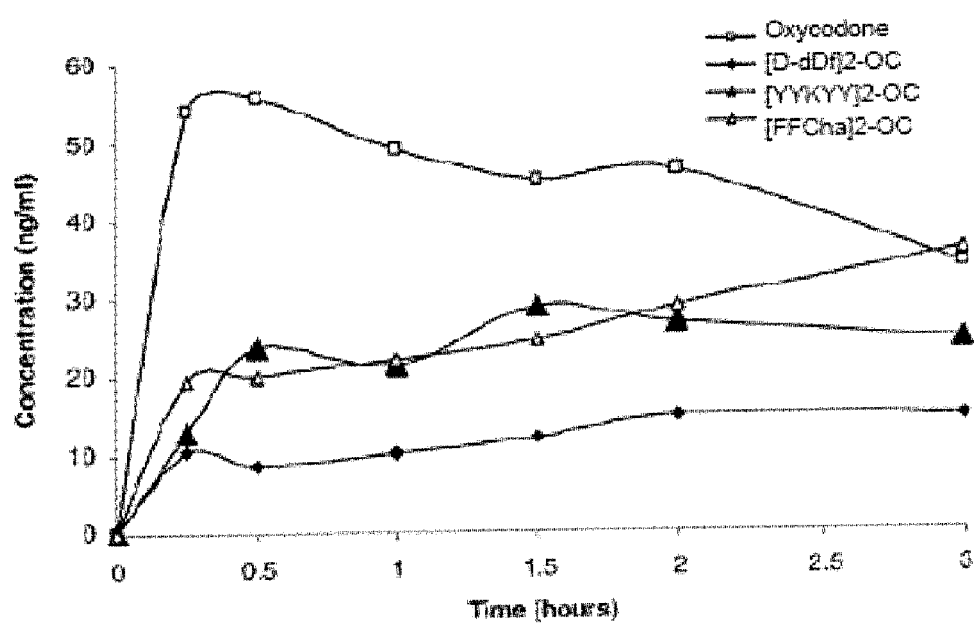
FIG. 10 Oral bioavailability of abuse-resistant oxycodone disubstituted tripeptide conjugates, measured as free oxycodone.
Figure 11:
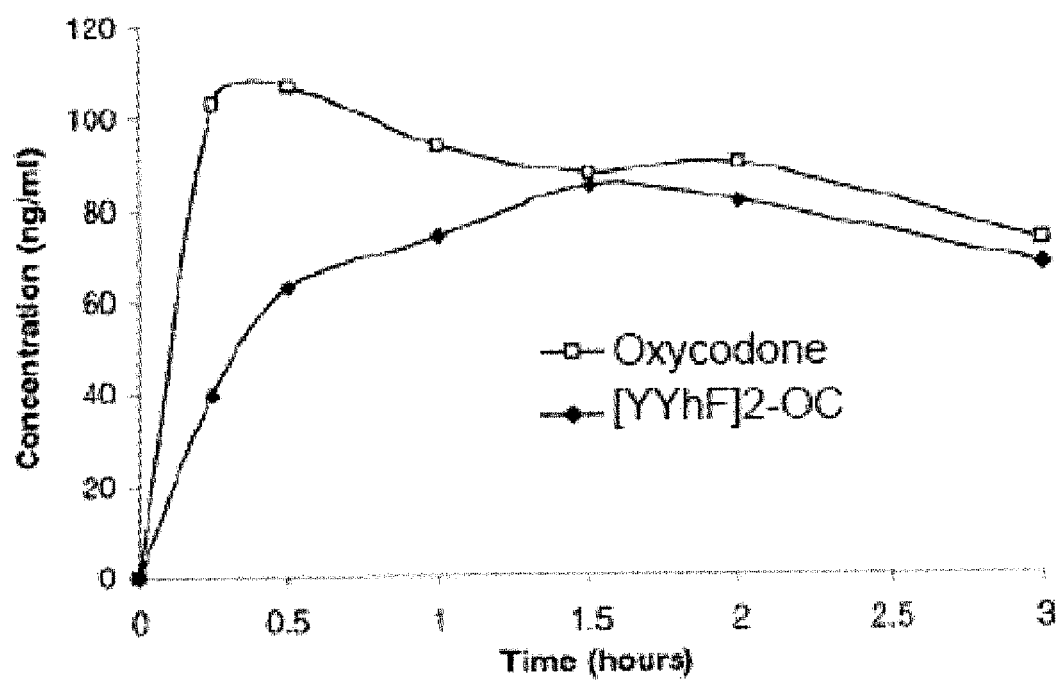
FIG. 11 Oral bioavailability of abuse-resistant oxycodone disubstituted tripeptide conjugates, measured as free oxycodone.
Figure 12:
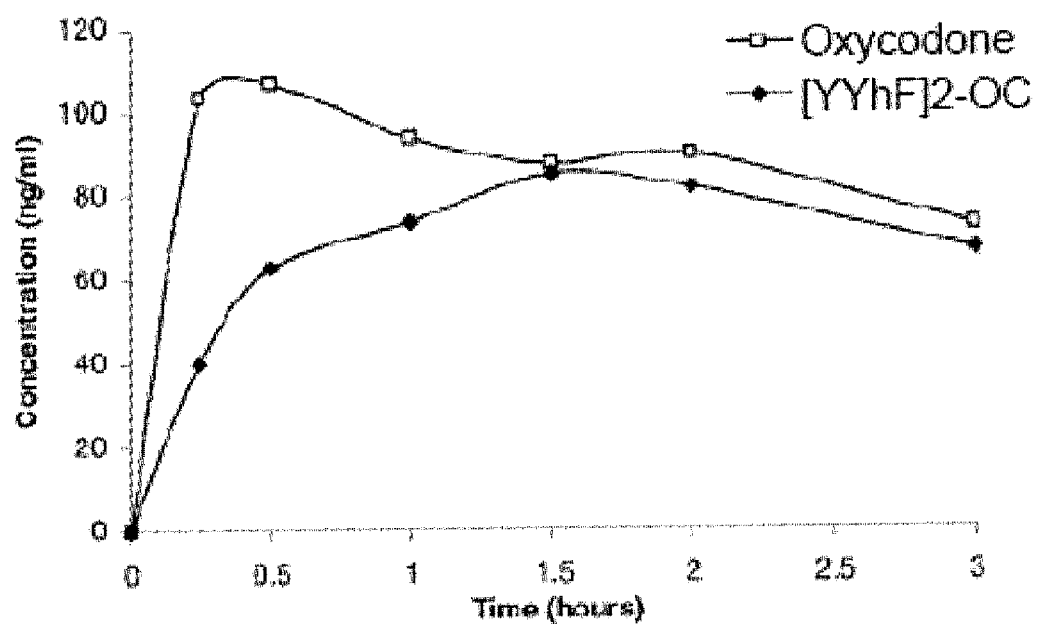
FIG. 12 Oral bioavailability of abuse-resistant oxycodone disubstituted tripeptide conjugates, measured as free oxycodone.
Figure 13:
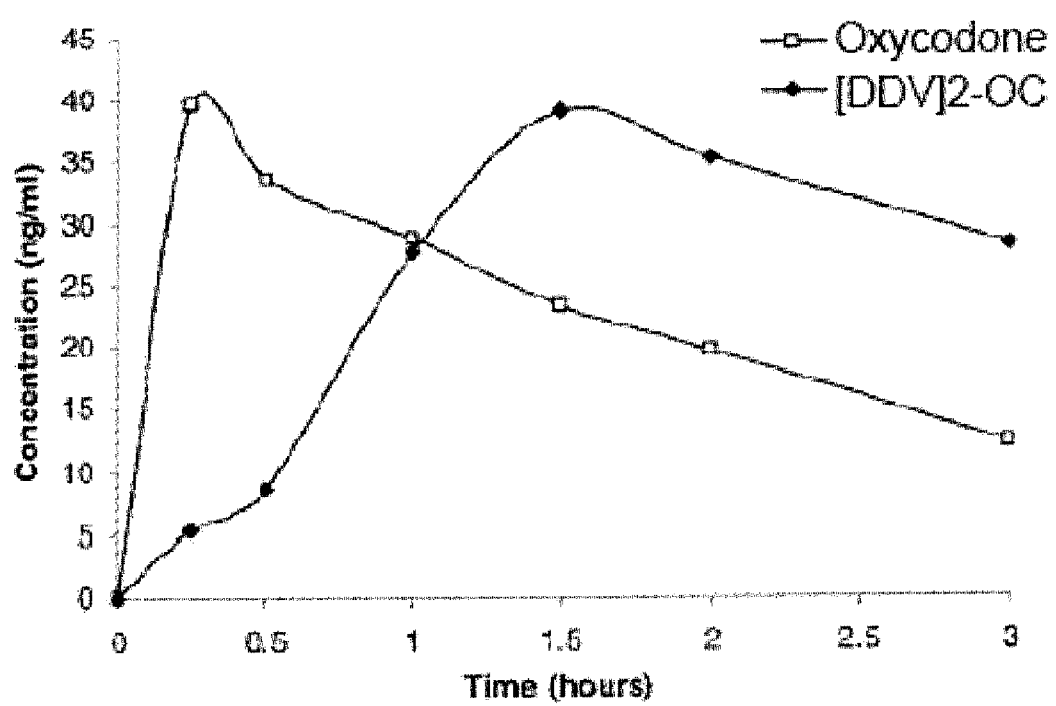
FIG. 13 Oral bioavailability of abuse-resistant oxycodone disubstituted tripeptide conjugates, measured as free oxycodone.
Figure 14:
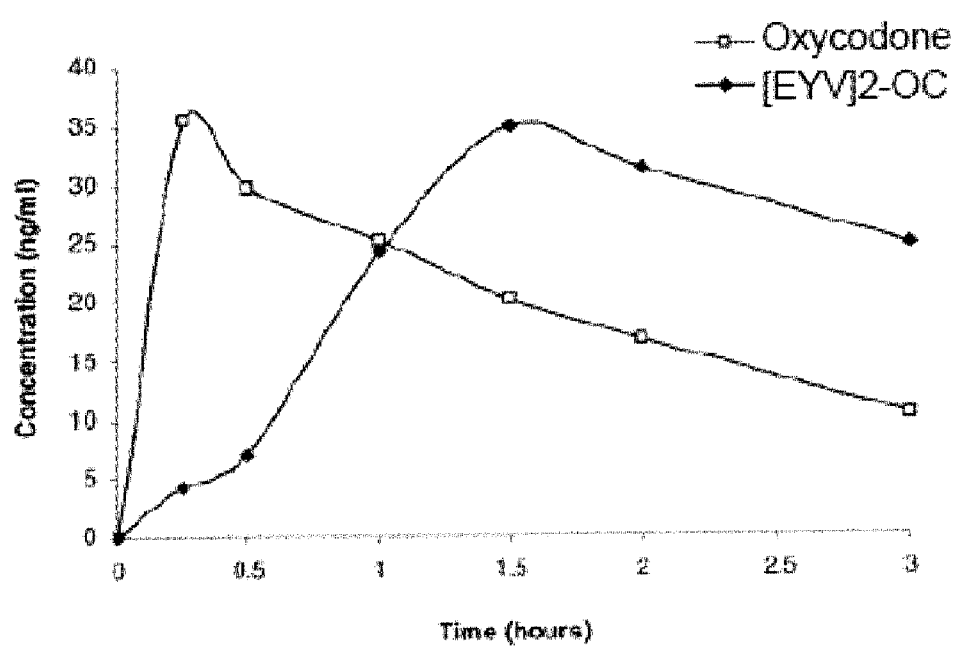
FIG. 14 Oral bioavailability of abuse-resistant oxycodone disubstituted tripeptide conjugates, measured as free oxycodone.
Figure 15:
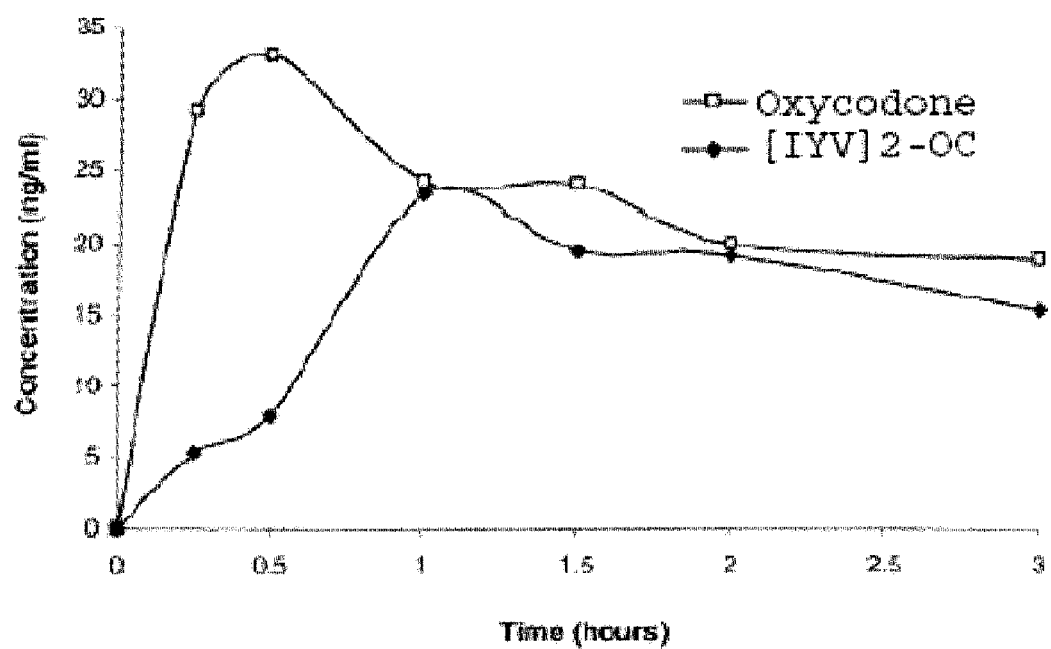
FIG. 15 Oral bioavailability of abuse-resistant oxycodone disubstituted tripeptide conjugates, measured as free oxycodone.
Figure 16:
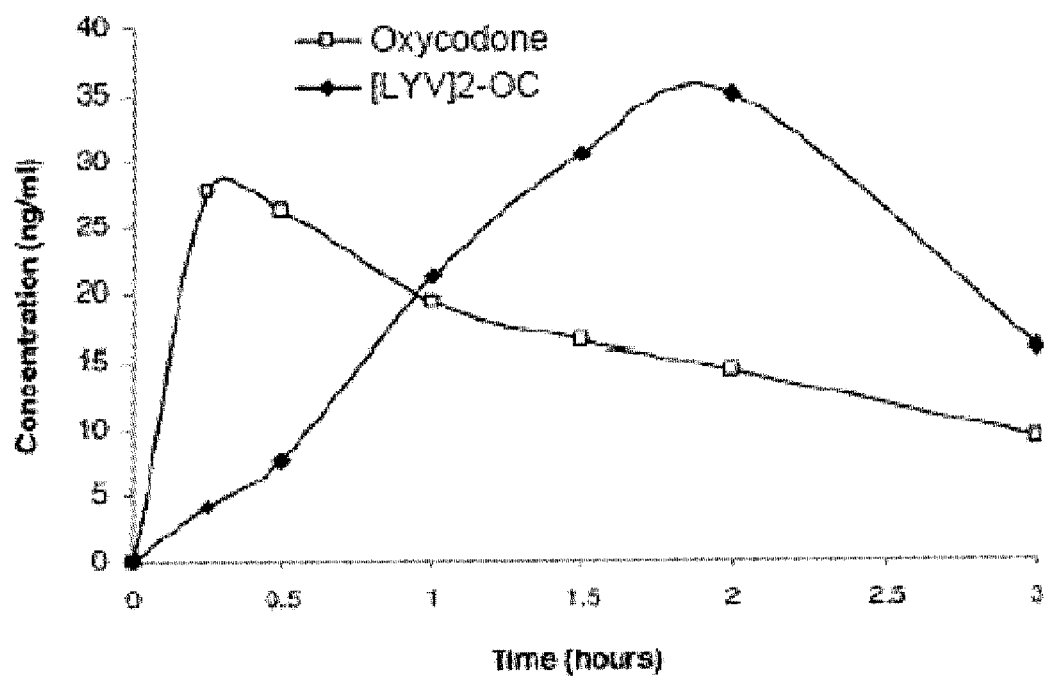
FIG. 16 Oral bioavailability of abuse-resistant oxycodone disubstituted tripeptide conjugates, measured as free oxycodone.
Figure 17:
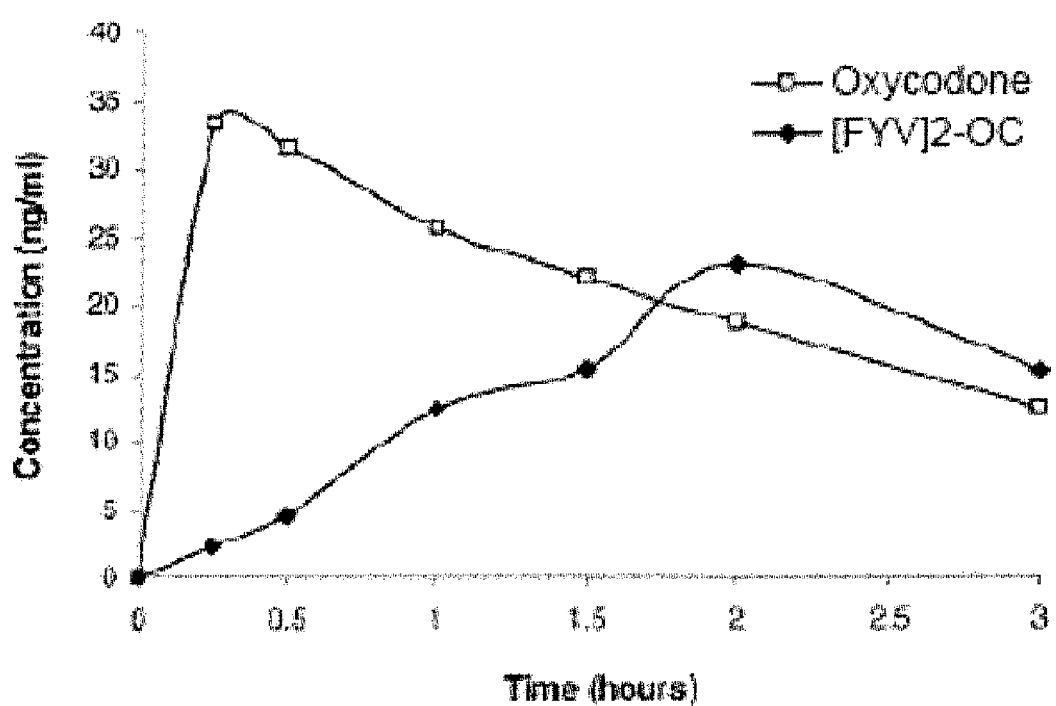
FIG. 17 Oral bioavailability of abuse-resistant oxycodone disubstituted tripeptide conjugates, measured as free oxycodone.
Figure 18:
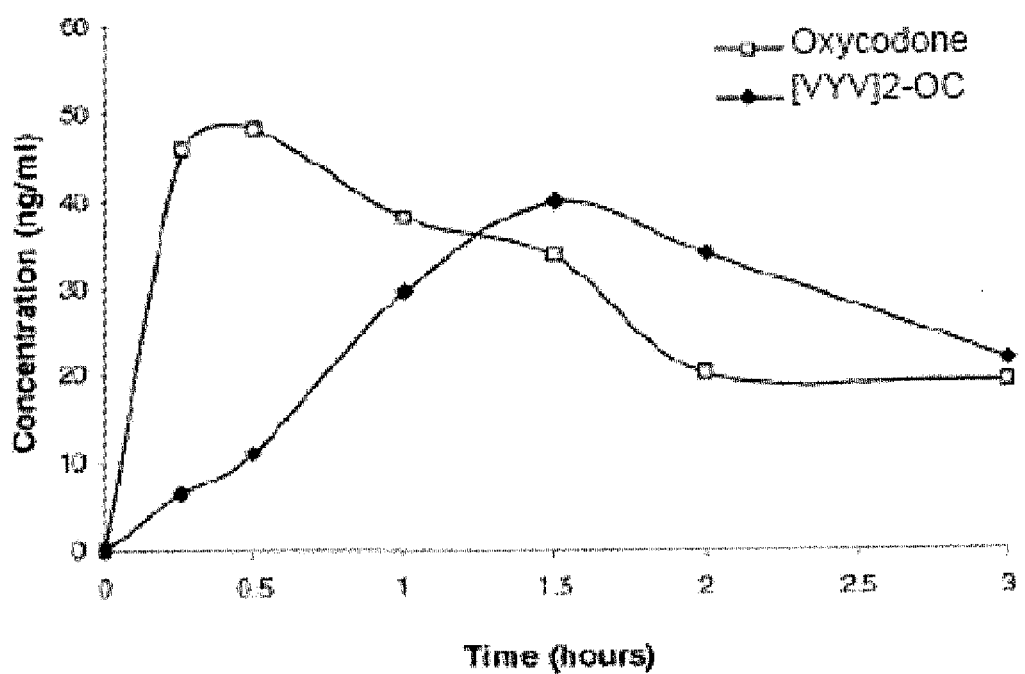
FIG. 18 Oral bioavailability of abuse-resistant oxycodone disubstituted tripeptide conjugates, measured as free oxycodone.
Figure 19:
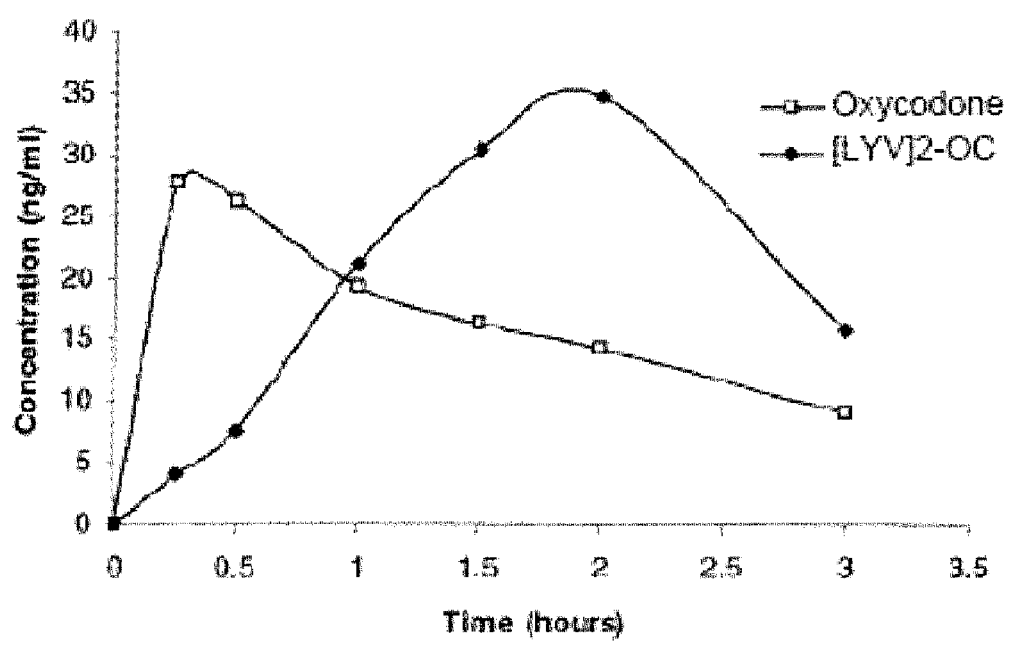
FIG. 19 Oral bioavailability of abuse-resistant oxycodone disubstituted tripeptide conjugates, measured as free oxycodone.
Figure 20:
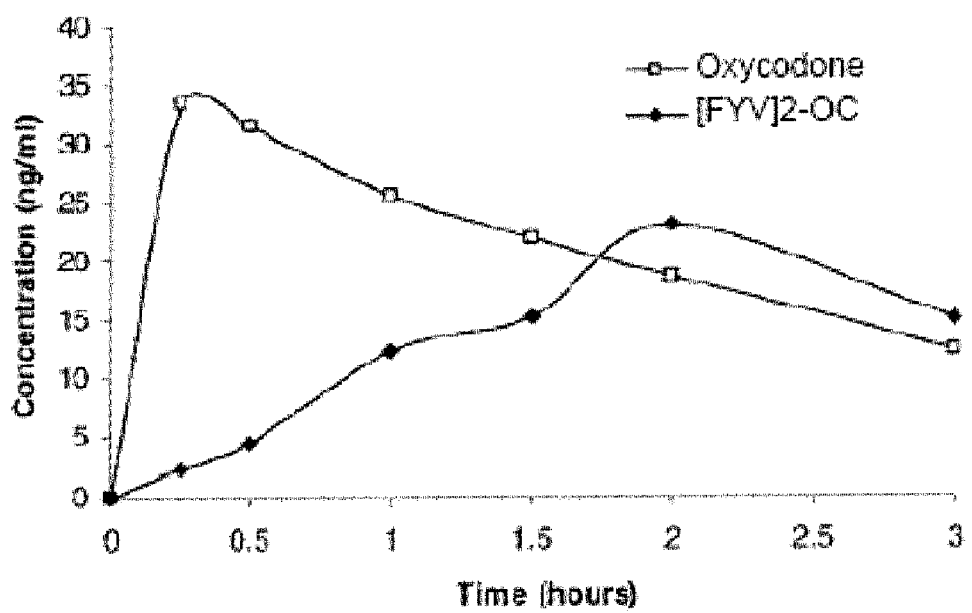
FIG. 20 Oral bioavailability of abuse-resistant oxycodone disubstituted tripeptide conjugates, measured as free oxycodone.
Figure 21:
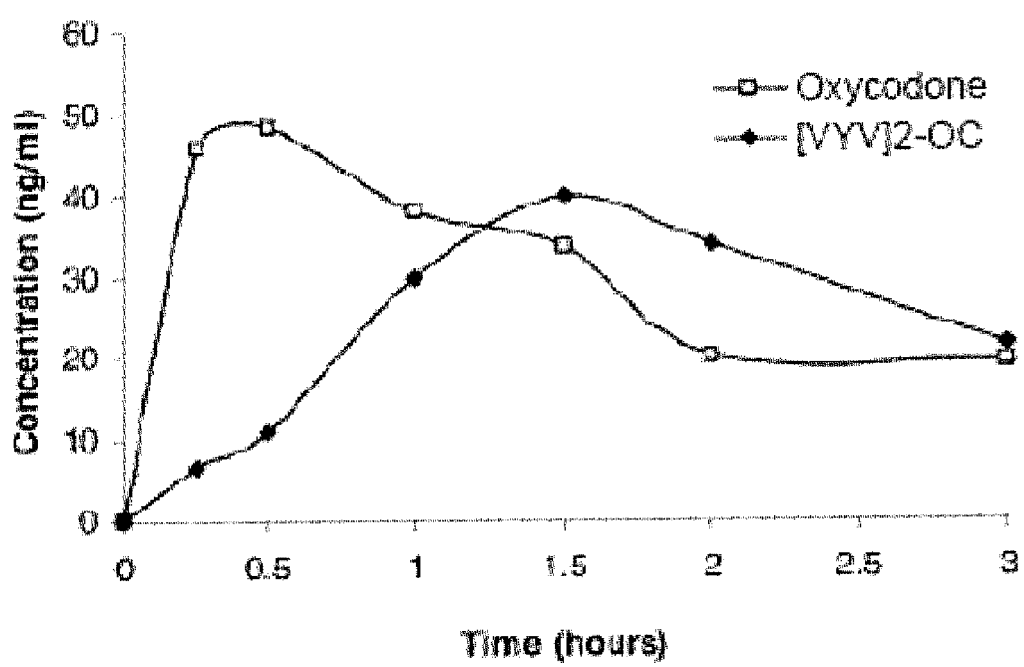
FIG. 21 Oral bioavailability of abuse-resistant oxycodone disubstituted tripeptide conjugates, measured as free oxycodone.
Figure 22:
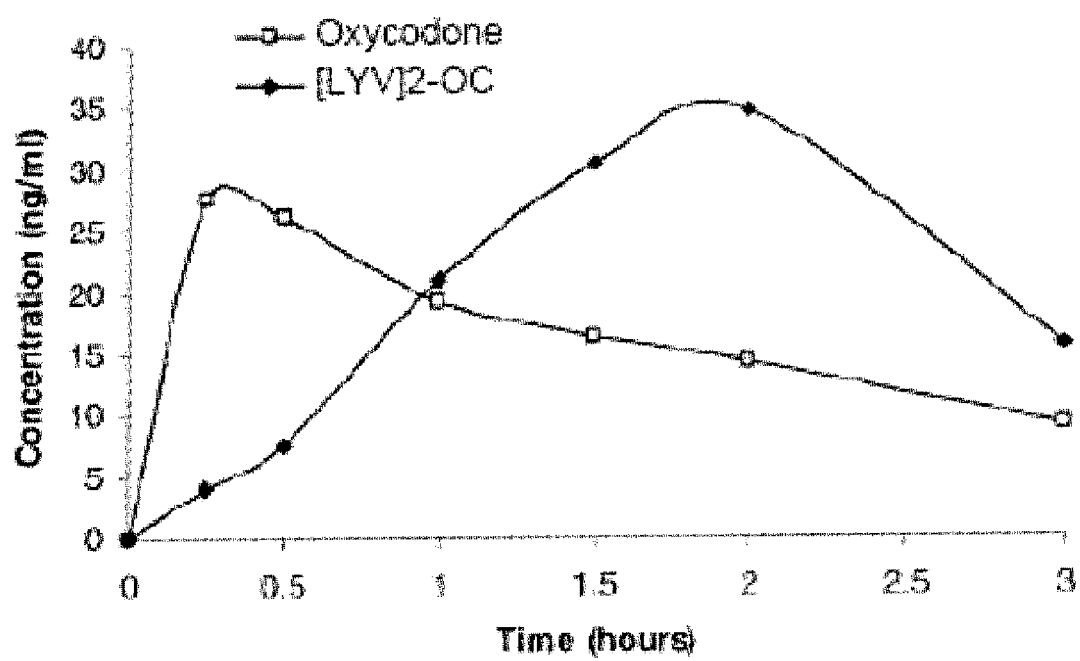
FIG. 22 Oral bioavailability of abuse-resistant oxycodone disubstituted tripeptide conjugates, measured as free oxycodone.
Figure 23:
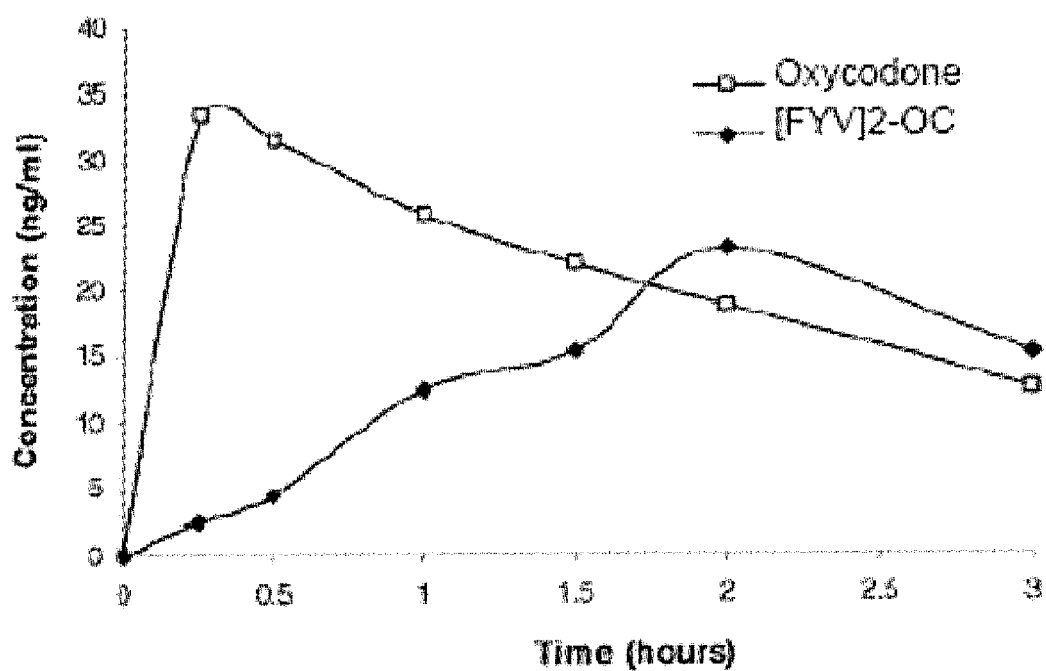
FIG. 23 Oral bioavailability of abuse-resistant oxycodone disubstituted tripeptide conjugates, measured as free oxycodone.
Figure 24:
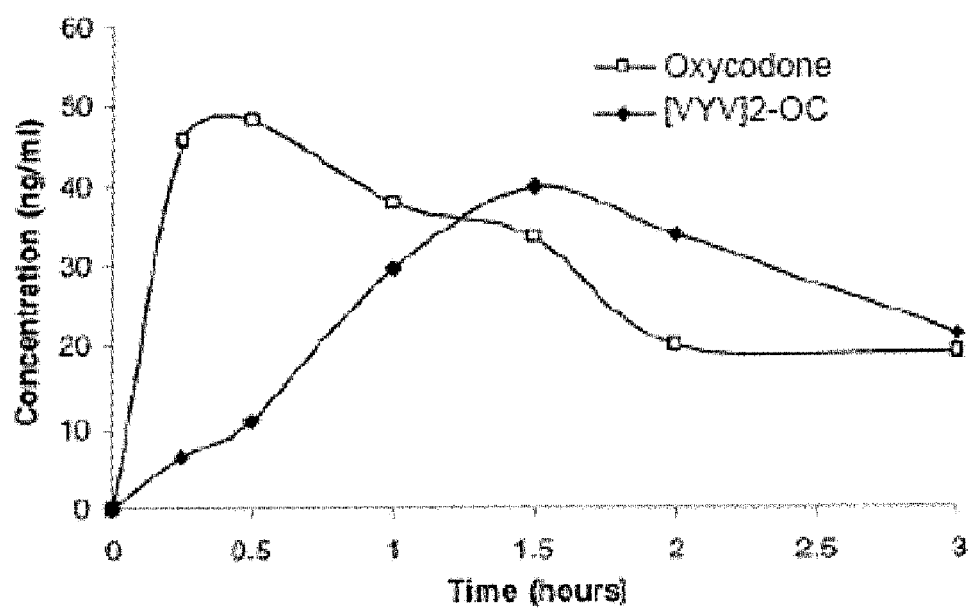
FIG. 24 Oral bioavailability of abuse-resistant oxycodone disubstituted tripeptide conjugates, measured as free oxycodone.
Figure 25:
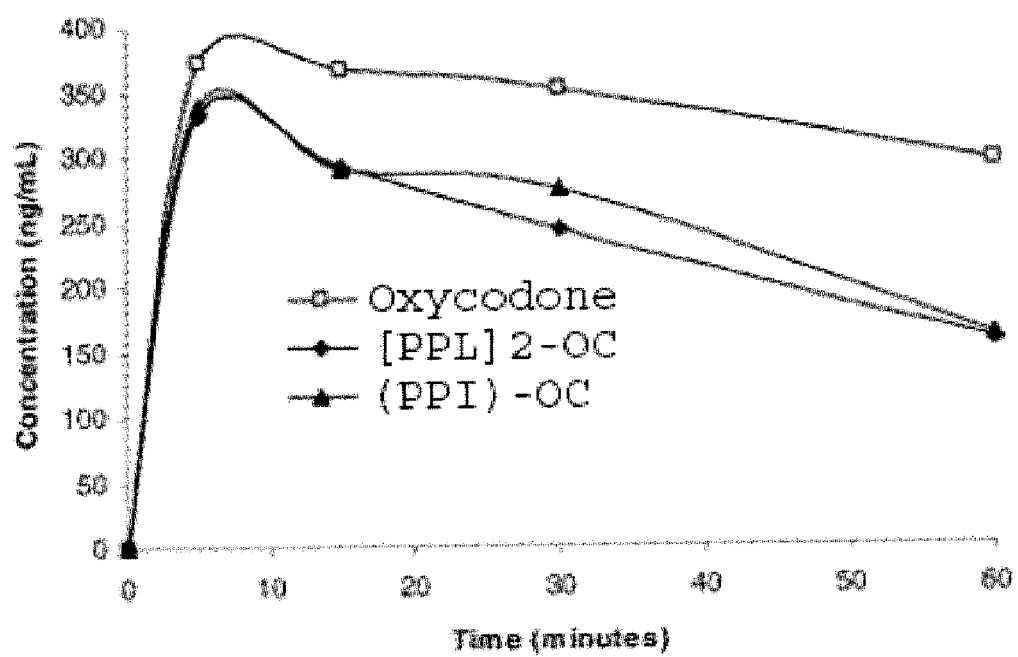
FIG. 25 Intranasal bioavailability of abuse-resistant oxycodone disubstituted tripeptide conjugates, measured as free oxycodone.
Figure 26:
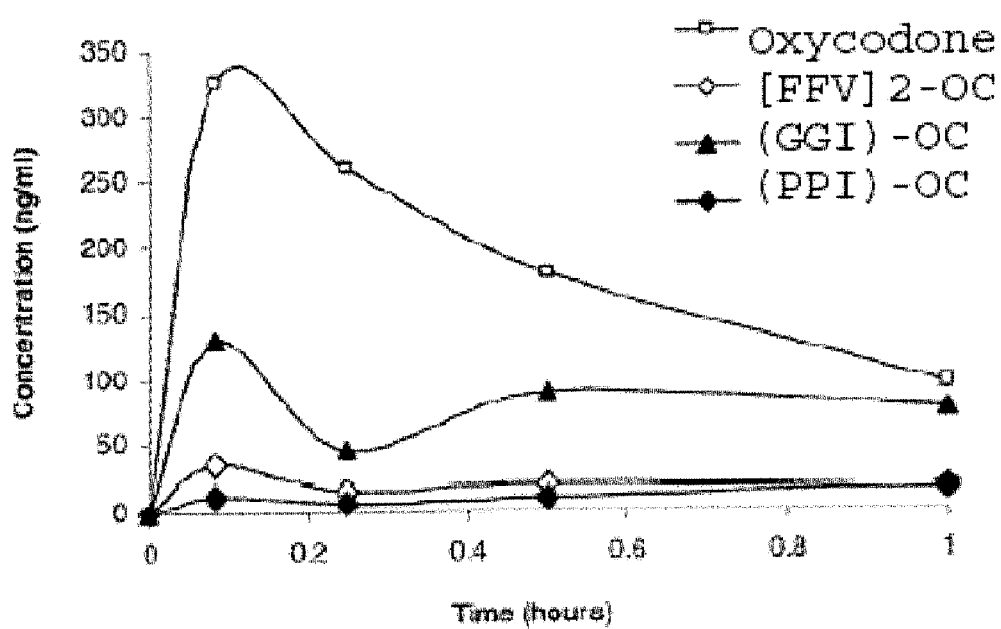
FIG. 26 Intranasal bioavailability of abuse-resistant oxycodone disubstituted tripeptide conjugates, measured as free oxycodone.
Figure 27:
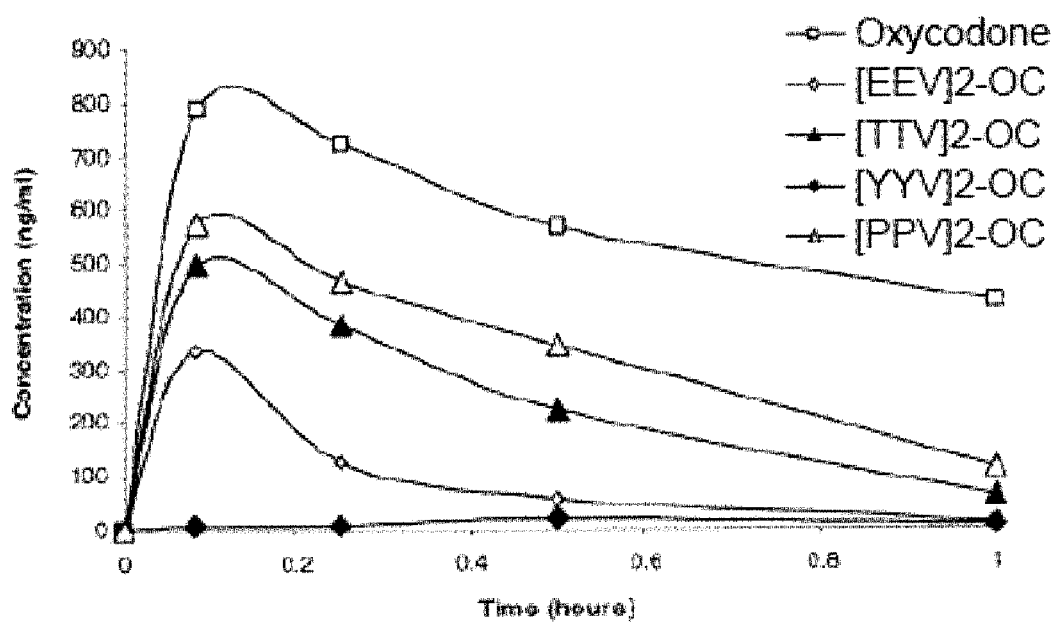
FIG. 27 Intranasal bioavailability of abuse-resistant oxycodone disubstituted tripeptide conjugates, measured as free oxycodone.
Figure 28:
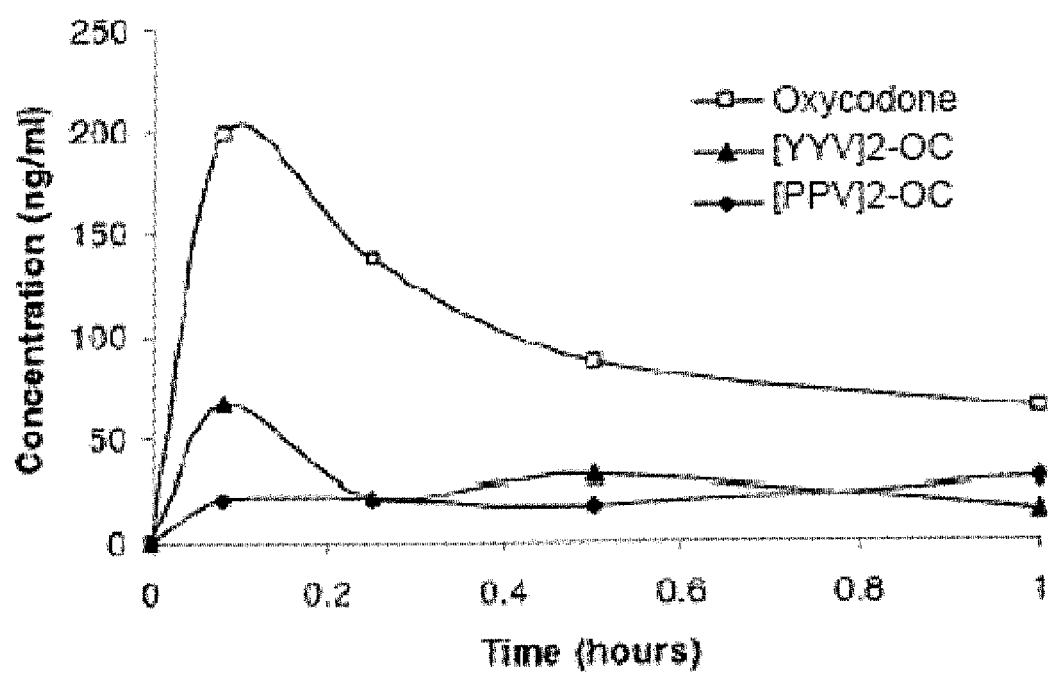
FIG. 28 Intravenous bioavailability of abuse-resistant oxycodone disubstituted tripeptide conjugates, measured as free oxycodone.
Figure 29:
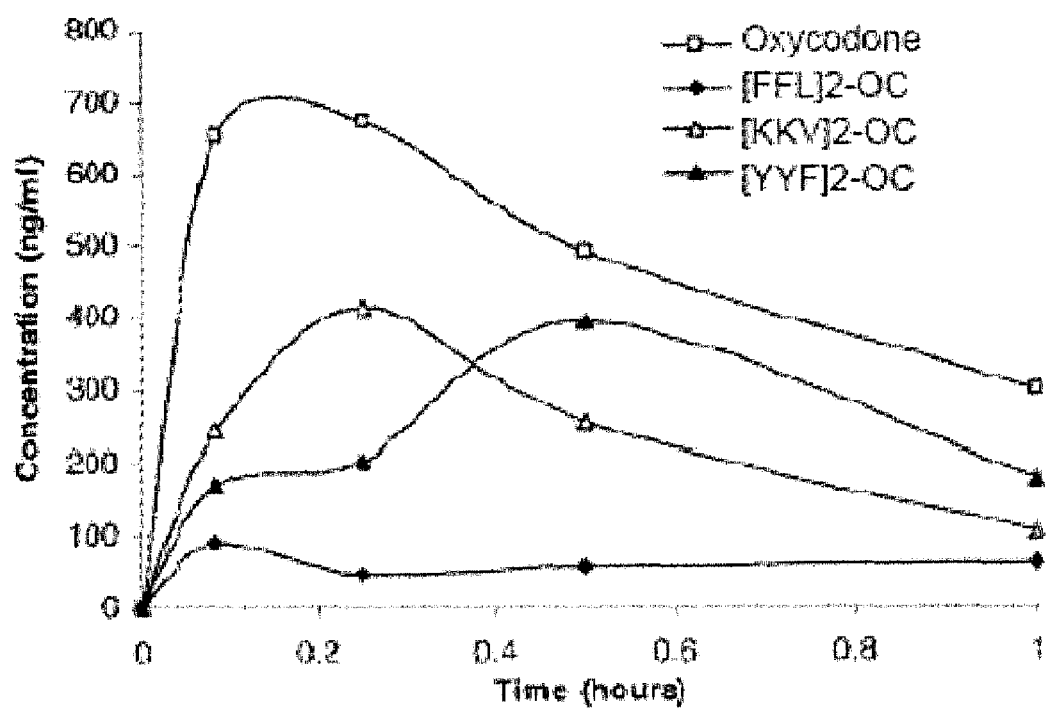
FIG. 29 Intranasal bioavailability of abuse-resistant oxycodone disubstituted tripeptide conjugates, measured as free oxycodone.
Figure 30:
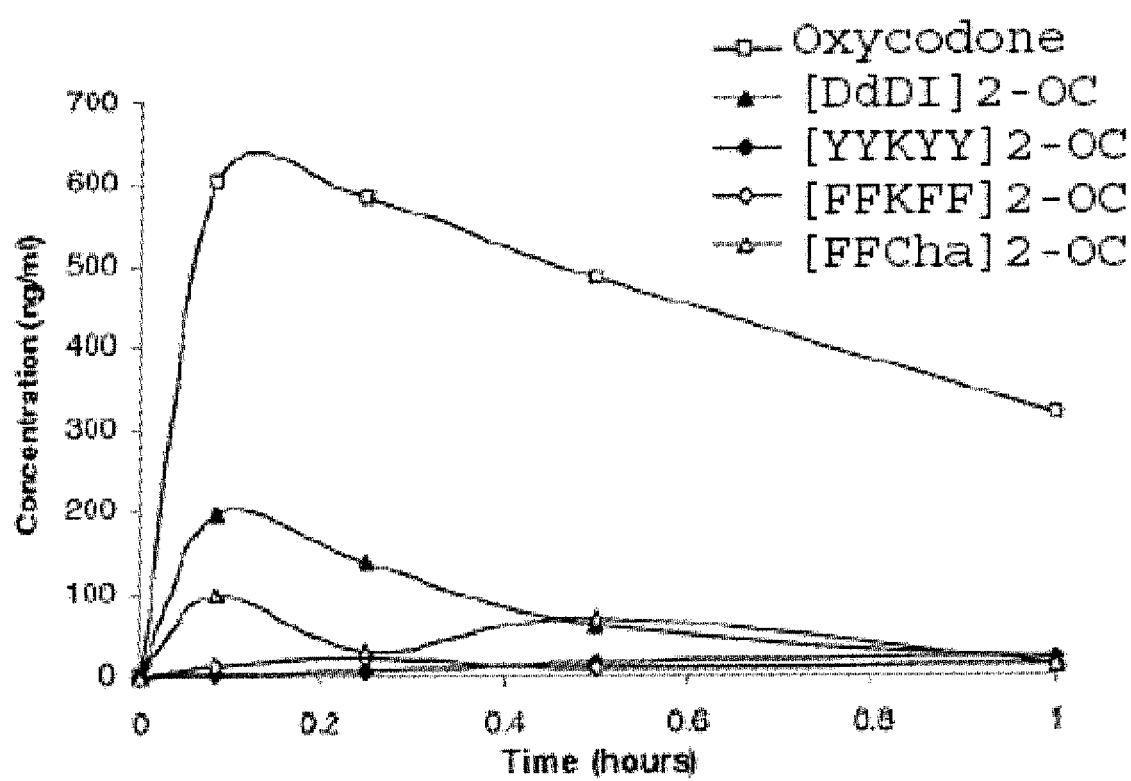
FIG. 30 Intranasal bioavailability of abuse-resistant oxycodone disubstituted tripeptide conjugates, measured as free oxycodone.
Figure 31:
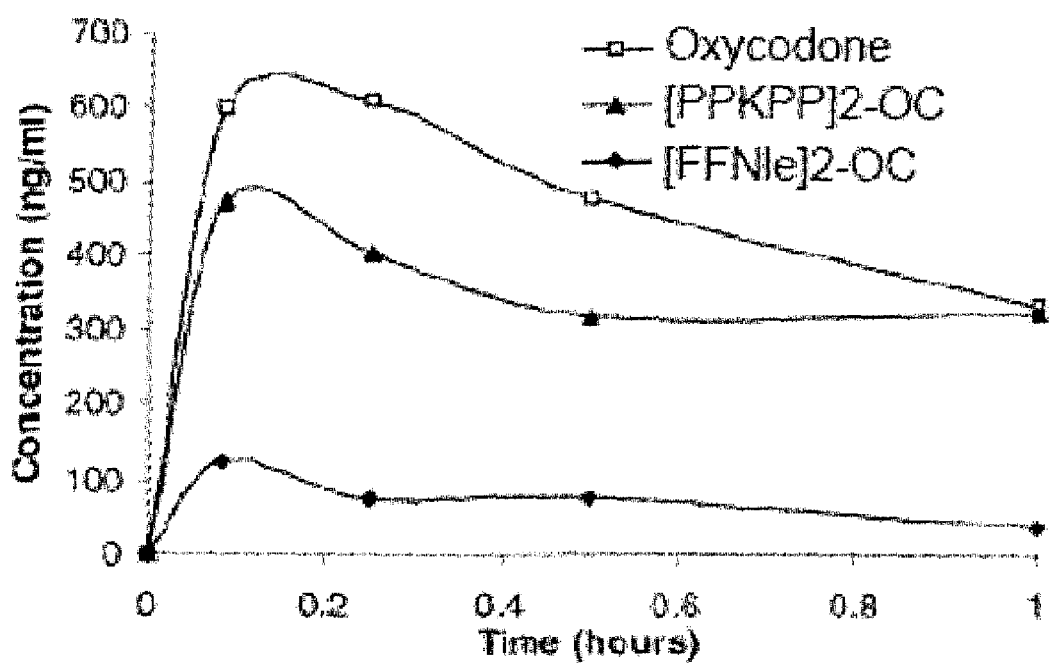
FIG. 31 Intranasal bioavailability of abuse-resistant oxycodone disubstituted tripeptide conjugates, measured as free oxycodone.
Figure 32:
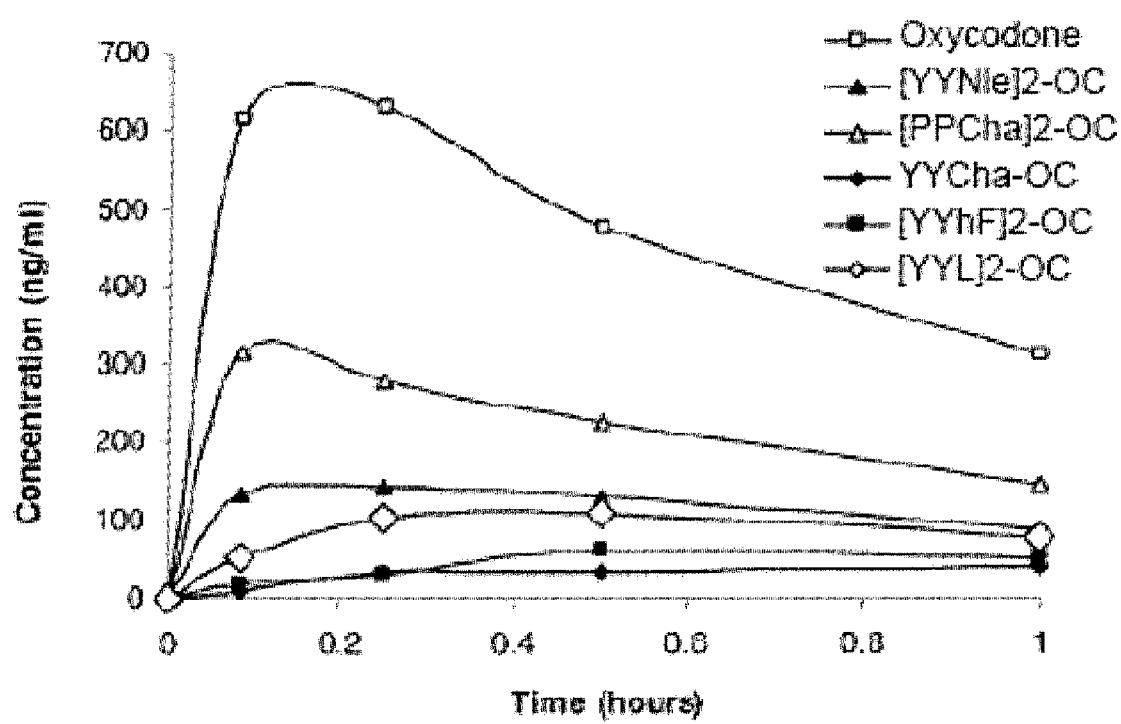
FIG. 32 Intranasal bioavailability of abuse-resistant oxycodone disubstituted tripeptide conjugates, measured as free oxycodone.
Figure 33:
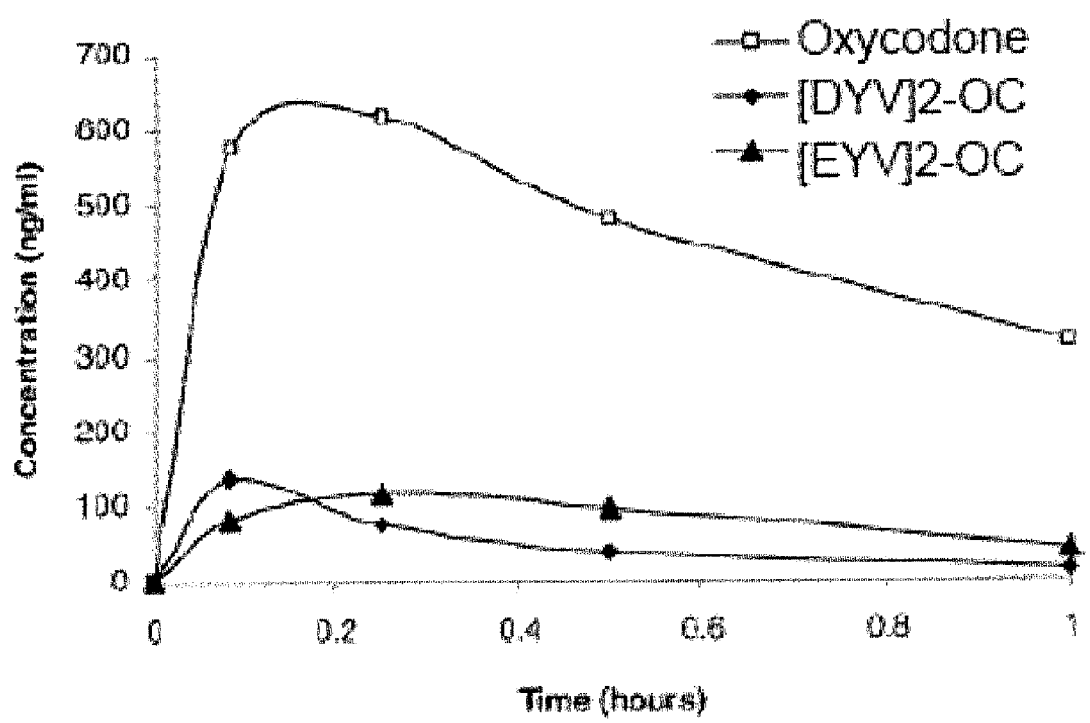
FIG. 33 Intranasal bioavailability of abuse-resistant oxycodone disubstituted tripeptide conjugates, measured as free oxycodone.
Figure 34:
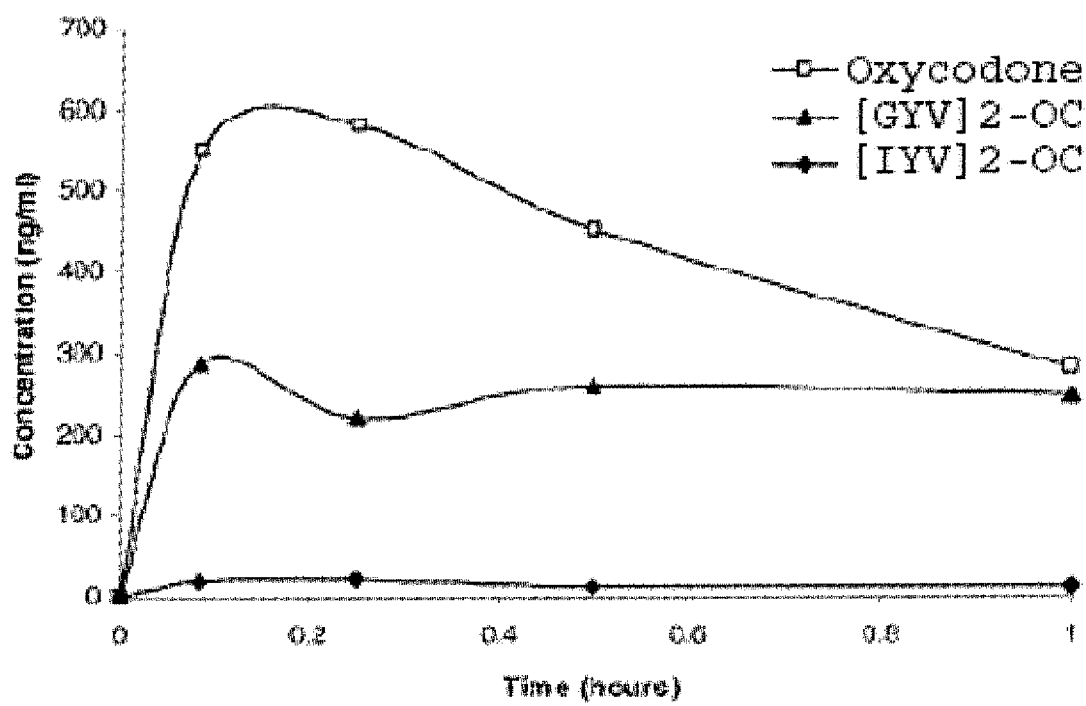
FIG. 34 Intranasal bioavailability of abuse-resistant oxycodone disubstituted tripeptide conjugates, measured as free oxycodone.
Figure 35:
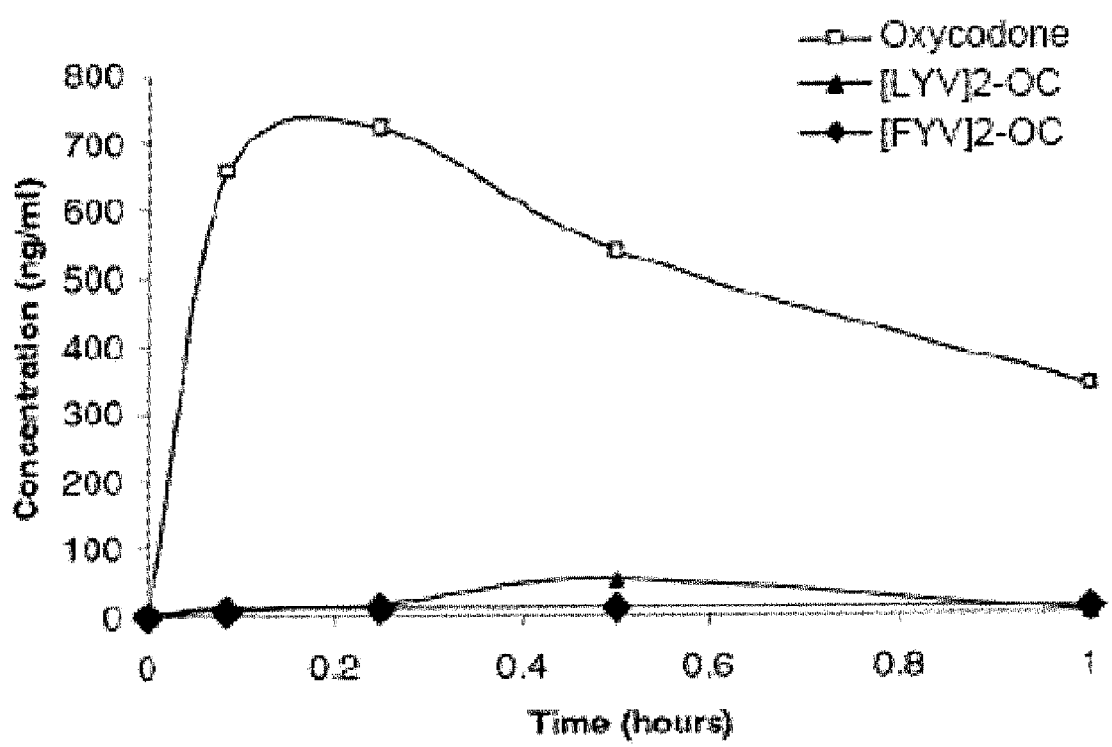
FIG. 35 Intranasal bioavailability of abuse-resistant oxycodone disubstituted tripeptide conjugates, measured as free oxycodone.
Figure 36:
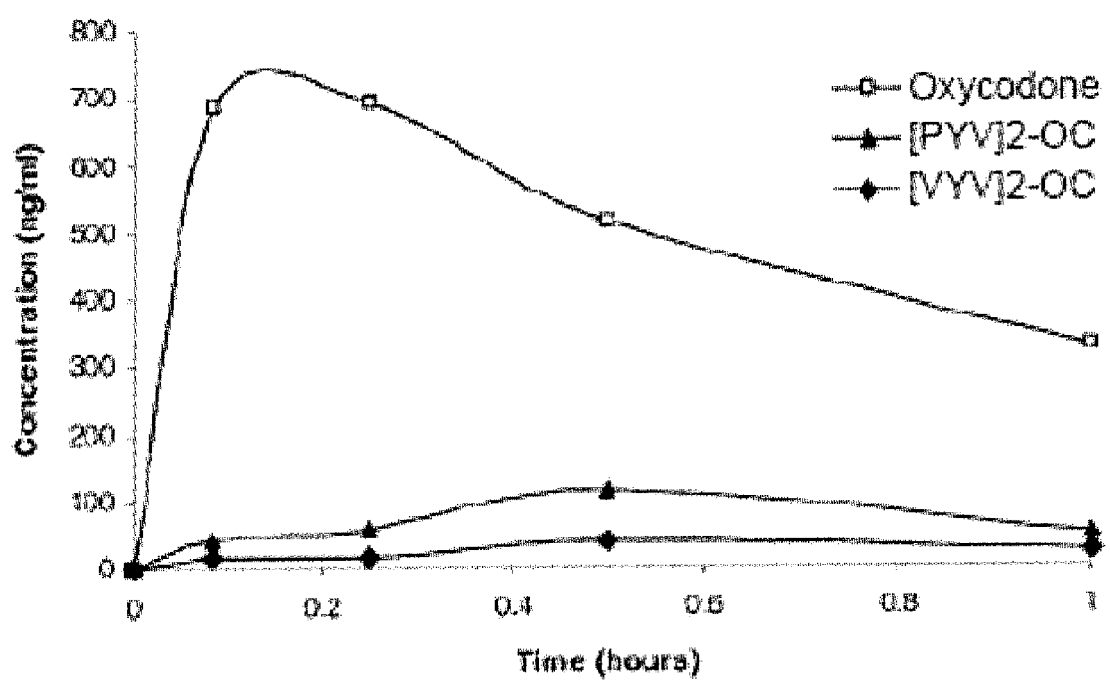
FIG. 36 Intranasal bioavailability of abuse-resistant oxycodone disubstituted tripeptide conjugates, measured as free oxycodone.
Figure 37:
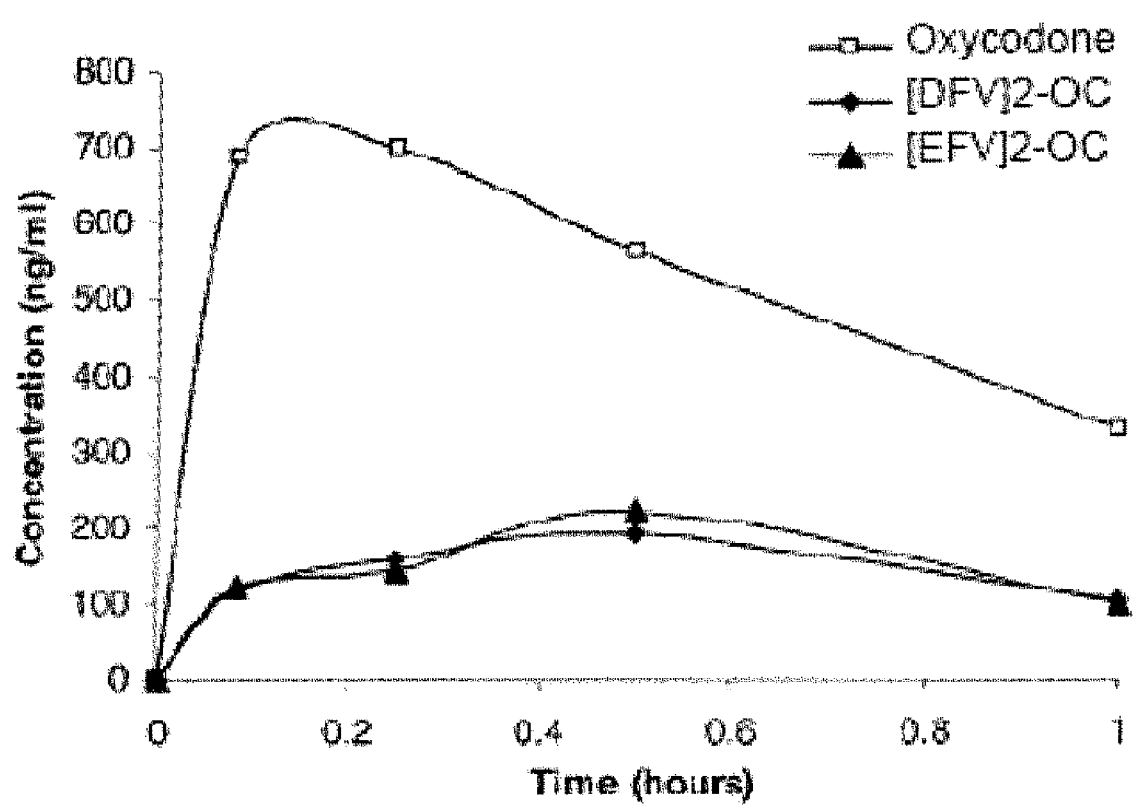
FIG. 37 Intranasal bioavailability of abuse-resistant oxycodone disubstituted tripeptide conjugates, measured as free oxycodone.
Figure 38:
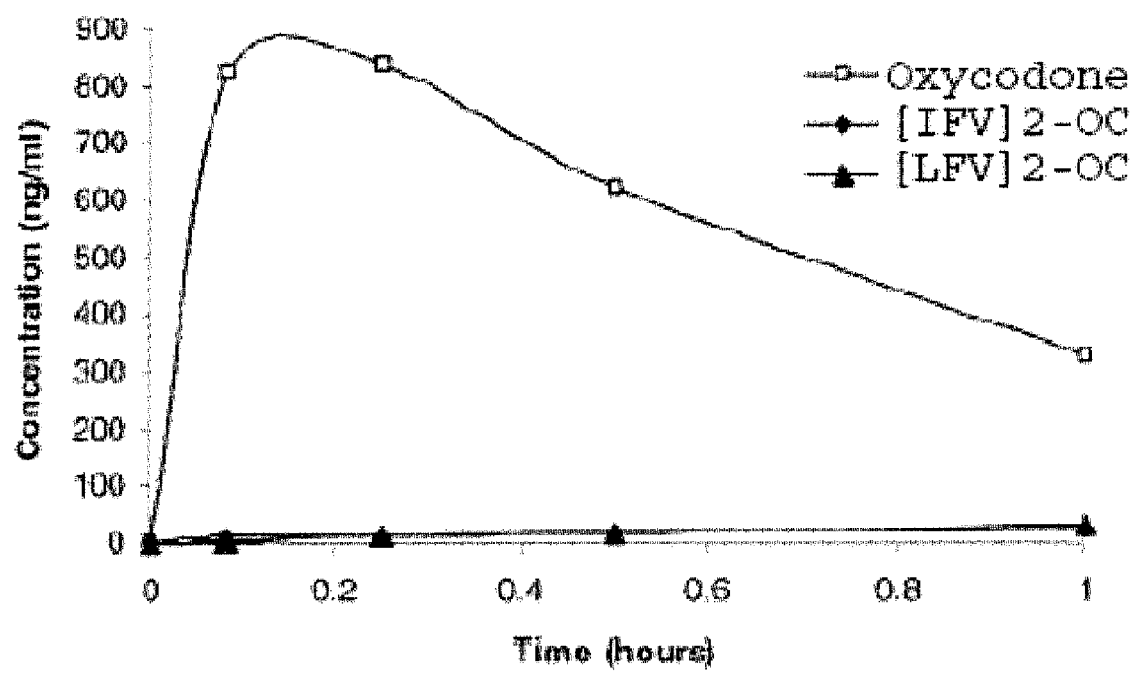
FIG. 38 Intranasal bioavailability of abuse-resistant oxycodone disubstituted tripeptide conjugates, measured as free oxycodone.
Figure 39:
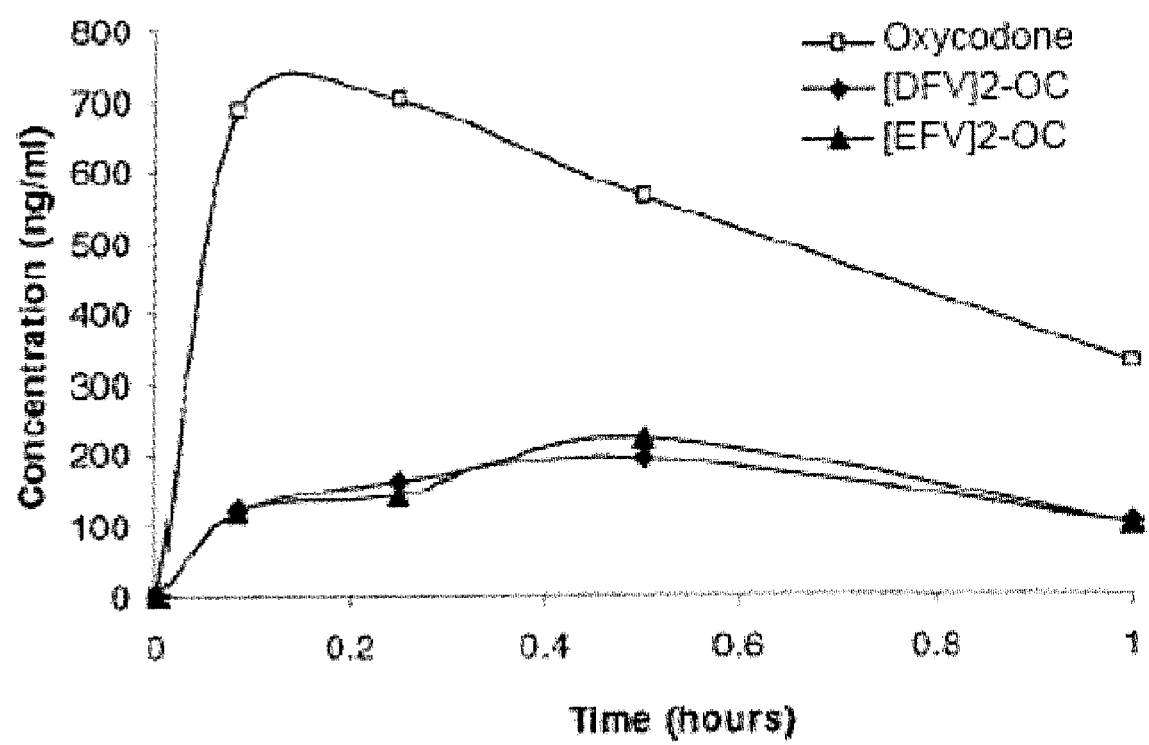
FIG. 39 Intranasal bioavailability of abuse-resistant oxycodone disubstituted tripeptide conjugates, measured as free oxycodone.
Figure 40:
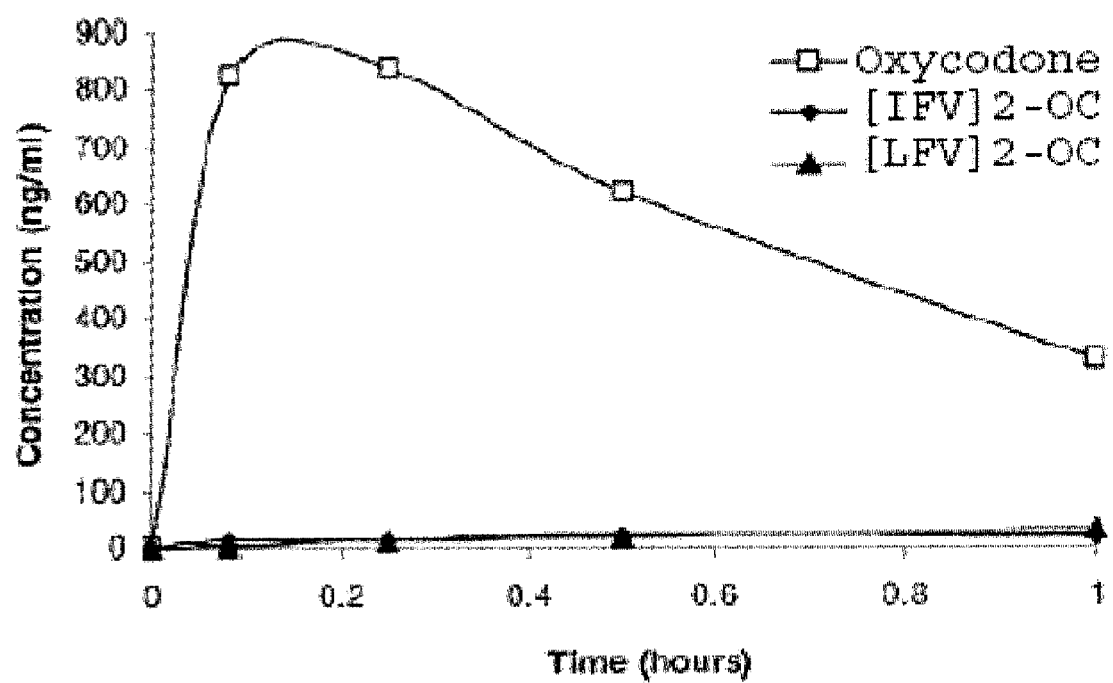
FIG. 40 Intranasal bioavailability of abuse-resistant oxycodone disubstituted tripeptide conjugates, measured as free oxycodone.
Figure 41:
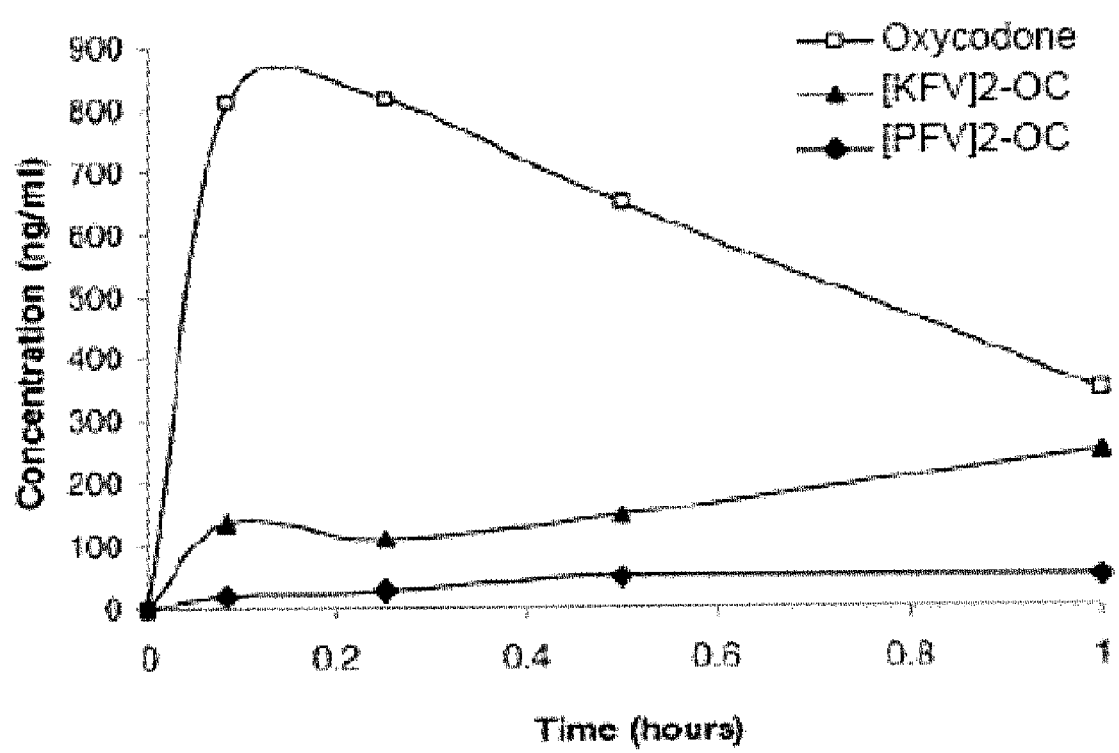
FIG. 41 Intranasal bioavailability of abuse-resistant oxycodone disubstituted tripeptide conjugates, measured as free oxycodone.
Figure 42:
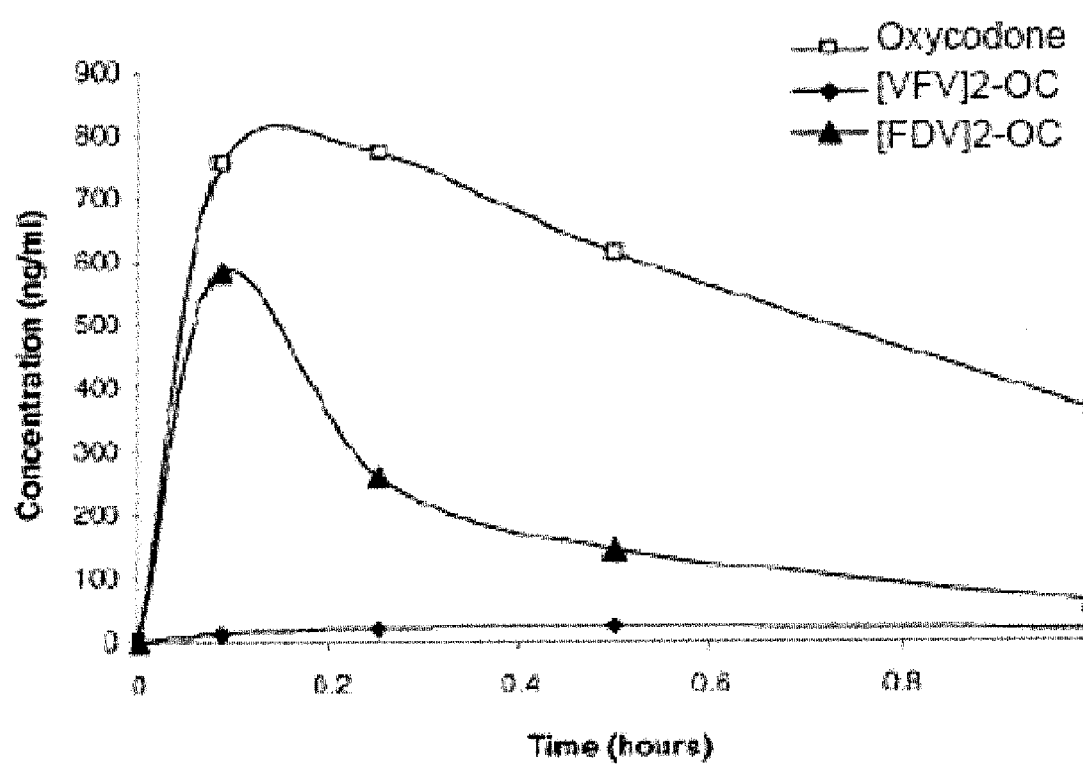
FIG. 42 Intranasal bioavailability of abuse-resistant oxycodone disubstituted tripeptide conjugates, measured as free oxycodone.
Figure 43:
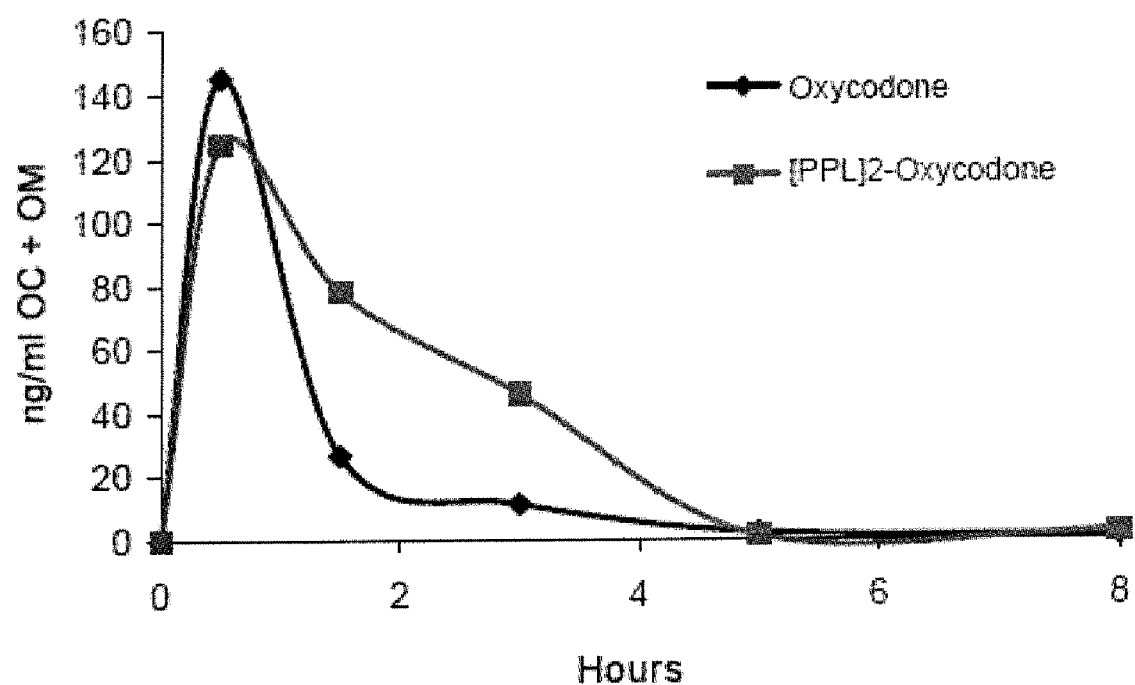
FIG. 43 Oral bioavailability in rats of oxycodone vs. $[PPL]_2$-Oxycodone at a dose (2.5 mg/kg) approximating a therapeutic human dose equivalent measured as free oxycodone.

FIG. 5 depicts niacin and biotin.

Vitamins can be used to cap or further functionalize the peptide chain. Niacin and biotin will be conjugated to four different dipeptides.

Conjugates to Prepare

1. [Gal-Gly$_2$-Ile]$_2$-OC
2. [Gal-Pro$_2$-Ile]$_2$-OC
3. [Gal-Gly$_2$-Leu]$_2$-OC
4. [Gal-Pro$_2$-Leu]$_2$-OC

FIGS. 6–42 demonstrate plasma levels of oxycodone measured by ELISA.

Male Sprague-Dawley rats were provided water ad libitum, fasted overnight and dosed by oral gavage with oxycodone conjugates or oxycodone HCl. All doses contained equivalent amounts of oxycodone base. Plasma oxycodone concentrations were measured by ELISA (Oxymorphone, 102919, Neogen, Corporation, Lexington, Ky.). The assay is specific for oxymorphone (the major oxycodone metabolite) and oxycodone. Plasma concentration-time curves are shown in FIGS. 6–24. These examples illustrate that doses of oxycodone conjugates decrease the peak level ($C_{max}$) of oxycodone plus oxymorphone as compared to that produced by equimolar (oxycodone base) doses of oxycodone HCl when given by the oral route of administration.

Example 31

Oral Bioavailability of a Peptide-Oxycodone Conjugates at a Dose (2.5 mg/kg) Approximating a Therapeutic Human Dose This example illustrates that when the peptide PPL (Table 1, FIG. 43) is conjugated (disubstituted at the 6 and 14 positions) to the active agent oxyocodone oral bioavailability is maintained as compared to an equimolar oxyocodone dose when the dose administered is 1 mg/kg. This dose is the equivalent of a human dose of 25 to 35 mg for an individual weighing 70 kg (148 lbs) according to Chou et al.

TABLE 1

Oral Pharmacokinetics of Oxycodone vs. [PPL]$_2$-OC (2.5 mg/kg dose).

| Drug | Hours | | | | | AUC (ng/ml h) 0–8 h | Percent OC | Cmax ng/ml | Percent OC |
| --- | --- | --- | --- | --- | --- | --- | --- | --- | --- |
| | 0.5 | 1.5 | 3 | 5 | 8 | | | | |
| Oxycodone Bitartrate | 145 | 27 | 11 | 2 | 1 | 168 | 100 | 145 | 100 |
| [PPL]$_2$-OC | 124 | 78 | 46 | 1 | 3 | 278 | 165 | 124 | 86 | oxycodone plus oxymorphone

Example 32

Bioavailability of [PPL]$_2$-Oxycodone by the Intranasal Route

Figure 44:
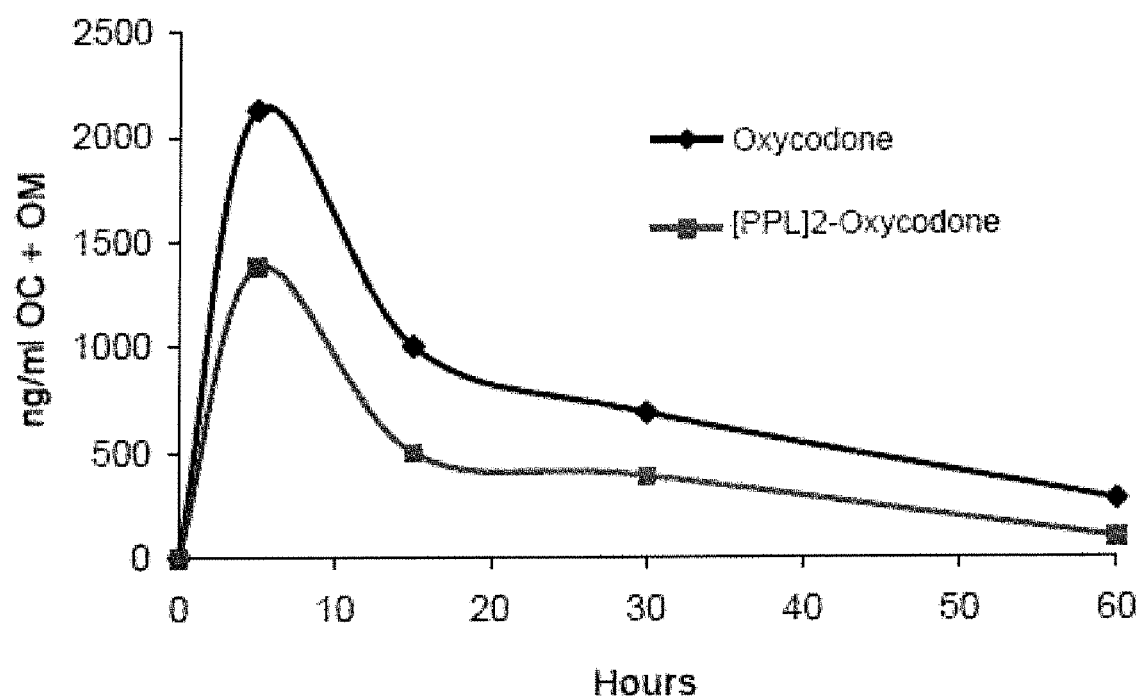
FIG. 44 Decrease in bioavailability of $[PPL]_2$-Oxycodone as compared to oxycodone by the intranasal route of administration- dose 2.5 mg/kg measured as free oxycodone.

This example illustrates that when [PPL]$_2$ is conjugated to the active agent oxycodone the bioavailability by the intranasal route is substantially decreased thereby diminishing the possibility of overdose (Table 2, FIG. 44).

TABLE 2

Intranasal Pharmacokinetics of Oxyocodone vs. [PPL]$_2$-OC (1 mg/kg dose).

| Drug | Minutes | | | | AUC (ng/ml h) 0–1 h | Percent OC | Cmax ng/ml | Percent OC |
| --- | --- | --- | --- | --- | --- | --- | --- | --- |
| | 5 | 15 | 30 | 60 | | | | |
| Oxycodone Bitartrate | 2128 | 1003 | 688 | 278 | 428 | 100 | 2128 | 100 |
| [PPL]$_2$-OC | 1380 | 499 | 390 | 98 | 261 | 61 | 1380 | 65 | oxycodone plus oxymorphone

Example 33

Bioavailability of [PPL]$_2$-Oxycodone by the Intravenous Route

Figure 45:
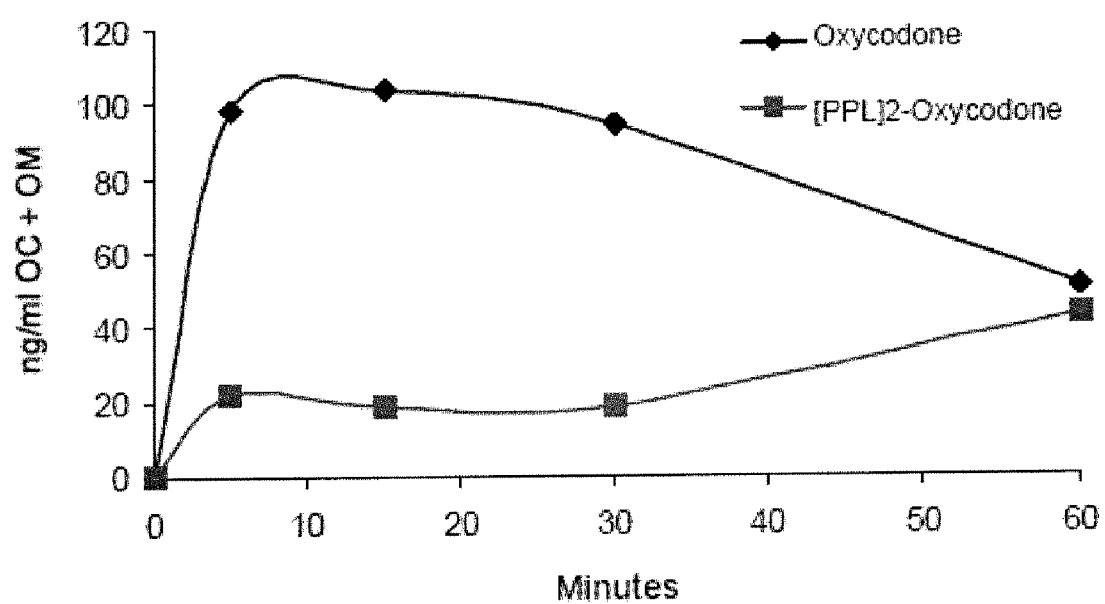
FIG. 45 Decrease in bioavailability of $[PPL]_2$-Oxycodone as compared to oxycodone by the intravenous route of administration- dose 0.5 mg/kg measured as free oxycodone.

This example illustrates that when [PPL]$_2$ is conjugated to the active agent oxycodone the bioavailability by the intravenous route is substantially decreased thereby diminishing the possibility of overdose (Table 3, FIG. 45).

TABLE 3

Intravenous Pharmacokinetics of Oxyocodone vs. [PPL]$_2$-OC (1 mg/kg dose).

| Drug | Minutes | | | | AUC (ng/ml h) | Percent | Cmax | Percent |
| --- | --- | --- | --- | --- | --- | --- | --- | --- |
| | 5 | 15 | 30 | 60 | 0–1 h | OC | ng/ml | OC |
| Oxycodone Bitartrate | 99 | 104 | 94 | 51 | 82 | 100 | 99 | 100 |
| [PPL]$_2$-OC | 22 | 19 | 19 | 43 | 24 | 29 | 43 | 43 | oxycodone plus oxymorphone

Summary of In Vivo Testing of Abuse Resistant Oxycodone Conjugates.

In vivo testing of oxycodone conjugates demonstrates for instance decreased oral $C_{max}$, decreased intranasal bioavailability (AUC and $C_{max}$), and decreased intravenous bioavailability (AUC and $C_{max}$) and is described in further detail below.

Example 34

Decreased Intranasal Bioavailability (AUC and $C_{max}$) of Oxycodone Conjugates Male Sprague-Dawley rats were provided water ad libitum and doses were administered by placing 0.02 ml of water containing oxycodone conjugates or oxycodone bitartrate into the nasal flares. All doses contained equivalent amounts of oxycodone base. Plasma oxycodone concentrations were measured by ELISA (Oxymorphone, 102919, Neogen, Corporation, Lexington, Ky.). The assay is specific for oxymorphone (the major oxycodone metabolite) and oxycodone. Plasma concentration-time curves of various oxycodone conjugates vs. oxycodone HCl are shown in FIGS. 25–42. These examples illustrate that oxycodone conjugates decrease the peak level ($C_{max}$) and total absorption (AUC) of oxycodone plus oxymorphone as compared to those produced by equimolar (oxycodone base) doses of oxycodone HCl when given by the intranasal route of administration.

Example 35

Decreased Intravenous Bioavailability (AUC and $C_{max}$) of Oxycodone Conjugates Male Sprague-Dawley rats were provided water ad libitum and doses were administered by intravenous tall vein injection of 0.1 ml of water containing oxycodone conjugates or oxycodone HCl. All doses contained equivalent amounts of oxycodone base. Plasma oxycodone concentrations were measured by ELISA (Oxymorphone, 102919, Neogen, Corporation, Lexington, Ky.). The assay is specific for oxymorphone (the major oxycodone metabolite) and oxycodone. Plasma concentration-time curves of an oxycodone conjugate vs. oxycodone HCl is shown in FIG. 45. This example illustrates that an oxycodone conjugate decreases the peak level ($C_{max}$) and total absorption (AUC) of oxycodone plus oxymorphone as compared to those produced by an equimolar (oxycodone base) dose of oxycodone HCl when given by the intravenous route of administration.

| | oral 2 mg/kg | | intranasal 2 mg/kg | |
| --- | --- | --- | --- | --- |
| | % AUC | % Cmax | % AUC | % Cmax |
| [Gly-Glu-Val]$_2$-OC | 93 | 61 | 29 | 48 |
| [Pro-Glu-Val]$_2$-OC | 90 | 82 | 34 | 46 |
| [Glu-Pro-Val]$_2$-OC | 142 | 134 | 56 | 65 |
| [Ser-Gly-Val]$_2$-OC | 90 | 92 | 64 | 73 |
| [Glu-Tyr-Val]$_2$-OC | 115 | 103 | 18 | 20 |
| [Gly-Tyr-Val]$_2$-OC | 92 | 99 | 56 | 54 |
| [Ile-Tyr-Val]$_2$-OC | 71 | 82 | 3 | 4 |
| [Leu-Tyr-Val]$_2$-OC | 131 | 120 | 4 | 5 |

OC = Oxycodone

Collectively, examples 1 through 35 illustrate the application of the invention for reducing the overdose potential of narcotic analgesics.

Collectively, these examples establish that an active agent can be covalently modified by attachment of a chemical moiety in a manner that maintains therapeutic value over a normal dosing range, while substantially decreasing if not eliminating the possibility of overdose by oral, intranasal, or intravenous routes of administration with the active agent.

The invention claimed is:

1. A method of making an ingredient for an oral dosage form of an oxycodone composition comprising:
covalently bonding at the 6' position and the 14' position of said oxycodone a single amino acid or an oligopeptide of 12 or fewer amino acids.

2. The method of claim 1 wherein the oligopeptide is a dipeptide.

3. The method of claim 1 wherein the oligopeptide is a tripeptide.

4. The method of claim 1 wherein the oligopeptide is a tetrapeptide.

5. The method of claim 1 wherein the oligopeptide is a pentapeptide.

6. The method of claim 1 wherein the oligopeptide is a hexapeptide.

7. The method of claim 1 wherein said oligopeptide consists essentially of naturally occurring amino acids.

8. The method of claim 1 wherein said oligopeptide consists of naturally occurring amino acids.

9. The method of claim 1, wherein each oligopeptide is Glu-Pro-Val.

10. The method of 1, wherein each oligopeptide is Glu-Tyr-Val.

11. The method of 1, wherein each oligopeptide is Ile-Tyr-Val.

12. The method of claims 1 wherein said oligopeptide is Phe-Phe-Lys-Phe-Phe [SEQ ID NO: 5]Tyr-Tyr-Lys-Tyr-Tyr [SEQ ID NO: 4], or Glu-Glu-Phe-Phe-Ile [SEQ ID NO: 1].

13. The method of claim 9, wherein said oral dosage form is a tablet, a capsule, an oral solution, or an oral suspension.

14. The method of claim 10, wherein said oral dosage form is a tablet, a capsule, an oral solution, or an oral suspension.

15. The method of claim 11, wherein said oral dosage form is a tablet, a capsule, an oral solution, or an oral suspension.

16. The method of claim 3, wherein the at least one tripeptide is Asp-Asp-Ile, Gly-Tyr-Ile, Phe-Phe-Val, Tyr-Tyr-Ile, Asp-Asp-Val, Gly-Tyr-Leu, Phe-Val-Val, Tyr-Tyr-Phe, Glu-Asp-Val, Gly-Tyr-Val, Pro-Glu-Val, Tyr-Tyr-Val, Glu-Glu-Val, Ile-Tyr-Val, Pro-Pro-Ile, Val-Glu-Gly, Glu-Leu-Val, Leu-Tyr-Val, Pro-Pro-Leu, Glu-Pro-Val, Lys-Lys-Leu, Pro-Pro-Vat, Glu-Tyr-Val, Lys-Lys-Val, Ser-Gly-Val, Gly-Glu-Val, Lys-Ser-Val, Ser-Thr-Val, Gly-Gly-Ile, Phe-Phe-Ile, Thr-Thr-Val, Gly-Leu-Val, Phe-Phe-Leu, or Tyr-Pro-Val.

17. The method of claim 3, wherein each tripeptide is one of Asp-Asp-Ile, Gly-Tyr-Ile, Phe-Phe-Val, Tyr-Tyr-Ile, Asp-Asp-Val, Gly-Tyr-Leu, Phe-Val-Val, Tyr-Tyr-Phe, Glu-Asp-Val, Gly-Tyr-Val, Pro-Glu-Val, Tyr-Tyr-Val, Glu-Glu-Val, Ile-Tyr-Val, Pro-Pro-Ile, Val-Glu-Gly, Glu-Leu-Val, Leu-Tyr-Val, Pro-Pro-Leu, Glu-Pro-Val, Lys-Lys-Leu, Pro-Pro-Val, Glu-Tyr-Val, Lys-Lys-Val, Ser-Gly-Val, Gly-Glu-Val, Lys-Ser-Val, Ser-Thr-Val, Gly-Gly-Ile, Phe-Phe-Ile, Thr-Thr-Val, Gly-Leu-Val, Phe-Phe-Leu, Tyr-Pro-Val.

18. The method of claim 1, wherein each oligopeptide is Glu-Asp-Val.

19. The method of claim 1, wherein each oligopeptide is Ser-Gly-Val.

20. The method of claim 16, wherein said oral dosage form is a tablet, a capsule, an oral solution, or an oral suspension.

21. The method of claim 17, wherein said oral dosage form is a tablet, a capsule, an oral solution, or an oral suspension.

22. The method of claim 18, wherein said oral dosage form is a tablet, a capsule, an oral solution, or an oral suspension.

23. The method of claim 19, wherein said oral dosage form is a tablet, a capsule, an oral solution, or an oral suspension.

24. The method of any of claims 1, 9, or 19, wherein the method prevents spiking or increased blood serum concentrations when delivered at doses exceeding those within the therapeutic range of said oxycodone.

25. The method of any of claims 1, 9, or 19, wherein the pharmacological activity of oxycodone is substantially decreased when the composition is used in a manner inconsistent with the manufacturer's instructions as compared to unbound oxycodone.

26. The method of any of claims 1, 9, or 19, wherein said oxycodone is released into a patient's bloodstream at levels that give rise to a reduced or delayed $C_{max}$ spike for oxycodone and provides a therapeutically effective bioavailability curve.

27. The method of any of claims 1, 9, or 19, wherein the bioavailability of the covalently modified oxycodone is diminished and delayed when delivered by routes other than oral administration as compared to unbound oxycodone.

28. The method of any of claims 1, 9, or 19, wherein the method provides a therapeutically effective bioavailability curve when delivered orally and in accordance with a manufacturer's instructions.

29. The method of any of claims 1, 9, or 19, wherein the method prevents spiking or increased blood serum concentrations when delivered at doses exceeding those within the therapeutic range of said oxycodone.

30. A method for altering short term bioavailability of oxycodone in an oral dosage form composition comprising:
covalently bonding at the 6' position and the 14' position of said oxycodone a single amino acid or an oligopeptide of 12 or fewer amino acids such that the short term bioavailability of oxycodone is altered.

31. The method of claim 30, wherein the oligopeptide is a dipeptide.

32. The method of claim 30, wherein the oligopeptide is a tripeptide.

33. The method of claim 30, wherein the oligopeptide is a tetrapeptide.

34. The method of claim 30, wherein the oligopeptide is a pentapeptide.

35. The method of claim 30, wherein the oligopeptide is a hexapeptide.

36. The method of claim 30, wherein said oligopeptide consists essentially of naturally occurring amino acids.

37. The method of claim 30, wherein said oligopeptide consists of naturally occurring amino acids.

38. The method of claim 30, wherein each oligopeptide is Glu-Pro-Val.

39. The method of claim 30, wherein each oligopeptide is Glu-Tyr-Val.

40. The method of claim 30, wherein each oligopeptide is Ile-Tyr-Val.

41. The method of claims 30, wherein said oligopeptide is Phe-Phe-Lys-Phe-Phe [SEQ D NO: 5] Tyr-Tyr-Lys-Tyr-Tyr [SEQ ID NO: 4], or Glu-Glu-Phe-Phe-Ile [SEQ ID NO: 1].

42. The method of claim 38, wherein said oral dosage form is a tablet, a capsule, an oral solution, or an oral suspension.

43. The method of claim 39, wherein said oral dosage form is a tablet, a capsule, an oral solution, or an oral suspension.

44. The method of claim 40, wherein said oral dosage form is a tablet, a capsule, an oral solution, or an oral suspension.

45. The method of claim 32, wherein the at least one tripeptide is Asp-Asp-Ile, Gly-Tyr-Ile, Phe-Phe-Val, Tyr-Tyr-Ile, Asp-Asp-Val, Gly-Tyr-Leu, Phe-Val-Val, Tyr-Tyr-Phe, Glu-Asp-Val, Gly-Tyr-Val, Pro-Glu-Val, Tyr-Tyr-Val, Glu-Glu-Val, Ile-Tyr-Val, Pro-Pro-Ile, Val-Glu-Gly, Glu-Leu-Val, Leu-Tyr-Val, Pro-Pro-Leu, Glu-Pro-Val, Lys-Lys-Leu, Pro-Pro-Val, Glu-Tyr-Val, Lys-Lys-Val, Ser-Gly-Val, Gly-Glu-Val, Lys-Ser-Val, Ser-Thr-Val, Gly-Gly-Ile, Phe-Phe-Ile, Thr-Thr-Val, Gly-Leu-Val, Phe-Phe-Leu, or Tyr-Pro-Val.

46. The method of claim 32, wherein each tripeptide is one of Asp-Asp-Ile, Gly-Tyr-Ile, Phe-Phe-Val, Tyr-Tyr-Ile, Asp-Asp-Val, Gly-Tyr-Leu, Phe-Val-Val, Tyr-Tyr-Phe, Glu-Asp-Val, Gly-Tyr-Val, Pro-Glu-Val, Tyr-Tyr-Val, Glu-Glu-Val, Ile-Tyr-Val, Pro-Pro-Ile, Val-Glu-Gly, Glu-Leu-Val, Leu-Tyr-Val, Pro-Pro-Leu, Glu-Pro-Val, Lys-Lys-Leu, Pro-Pro-Val, Glu-Tyr-Val, Lys-Lys-Val, Ser-Gly-Val, Gly-Glu-Val, Lys-Ser-Val, Ser-Thr-Val, Gly-Gly-Ile, Phe-Phe-Ile, Thr-Thr-Val, Gly-Leu-Val, Phe-Phe-Leu, Tyr-Pro-Val.

47. The method of claim 30, wherein each oligopeptide is Glu-Asp-Val.

48. The method of claim 30, wherein each oligopeptide is Ser-Gly-Val.

49. The method of claim 45, wherein said oral dosage form is a tablet, a capsule, an oral solution, or an oral suspension.

50. The method of claim 46, wherein said oral dosage form is a tablet, a capsule, an oral solution, or an oral suspension.

51. The method of claim 47, wherein said oral dosage form is a tablet, a capsule, an oral solution, or an oral suspension.

52. The method of claim 48, wherein said oral dosage form is a tablet, a capsule, an oral solution, or an oral suspension.

53. The method of any of claims 30, 38, or 48, wherein the method prevents spiking or increased blood serum concentrations when delivered at doses exceeding those within the therapeutic range of said oxycodone.

54. The method of any of claims 30, 38, or 48, wherein the pharmacological activity of oxycodone is substantially decreased when the composition is used in a manner inconsistent with the manufacturer's instructions as compared to unbound oxycodone.

55. The method of any of claims 30, 38, or 48, wherein said oxycodone is released into a patient's bloodstream at levels that give rise to a reduced or delayed $C_{max}$ spike for oxycodone and provides a therapeutically effective bioavailability curve.

56. The method of any of claims 30, 38, or 48, wherein the bioavailability of the covalently modified oxycodone is diminished and delayed when delivered by routes other than oral administration as compared to unbound oxycodone.

57. The method of any of claims 30, 38, or 48, wherein the method provides a therapeutically effective bioavailability curve when delivered orally and in accordance with a manufacturer's instructions.

58. The method of any of claims 30, 38, or 48, wherein the method prevents spiking or increased blood serum concentrations when delivered at doses exceeding those within the therapeutic range of said oxycodone.

59. A method for treating pain comprising delivering an oral dosage form of oxycodone, wherein said oxycodone is covalently bound to a single amino acid or an oligopeptide of 12 or fewer amino acids at the 6' position and the 14' position of said oxycodone.

60. The method of claim 59, wherein the oligopeptide is a dipeptide.

61. The method of claim 59, wherein the oligopeptide is a tripeptide.

62. The method of claim 59, wherein the oligopeptide is a tetrapeptide.

63. The method of claim 59, wherein the oligopeptide is a pentapeptide.

64. The method of claim 59, wherein the oligopeptide is a hexapeptide.

65. The method of claim 59, wherein said oligopeptide consists essentially of naturally occurring amino acids.

66. The method of claim 59, wherein said oligopeptide consists of naturally occurring amino acids.

67. The method of claim 59, wherein each oligopeptide is Glu-Pro-Val.

68. The method of claim 59, wherein each oligopeptide is Glu-Tyr-Val.

69. The method of claim 59, wherein each oligopeptide is Ile-Tyr-Val.

70. The method of claims 59, wherein said oligopeptide is Phe-Phe-Lys-Phe-Phe [SEQ ID NO: 5] Tyr-Tyr-Lys-Tyr-Tyr [SEQ ID NO: 4], or Glu-Glu-Phe-Phe-Ile [SEQ ID NO: 1].

71. The method of claim 67, wherein said oral dosage form is a tablet, a capsule, an oral solution, or an oral suspension.

72. The method of claim 68, wherein said oral dosage form is a tablet, a capsule, an oral solution, or an oral suspension.

73. The method of claim 69, wherein said oral dosage form is a tablet, a capsule, an oral solution, or an oral suspension.

74. The method of claim 59, wherein the at least one tripeptide is Asp-Asp-Ile, Gly-Tyr-Ile, Phe-Phe-Val, Tyr-Tyr-Ile, Asp-Asp-Val, Gly-Tyr-Leu, Phe-Val-Val, Tyr-Tyr-Phe, Glu-Asp-Val, Gly-Tyr-Val, Pro-Glu-Val, Tyr-Tyr-Val, Glu-Glu-Val, Ile-Tyr-Val, Pro-Pro-Ile, Val-Glu-Gly, Glu-Leu-Val, Leu-Tyr-Val, Pro-Pro-Leu, Glu-Pro-Val, Lys-Lys-Leu, Pro-Pro-Val, Glu-Tyr-Val, Lys-Lys-Val, Ser-Gly-Val, Gly-Glu-Val, Lys-Ser-Val, Ser-Thr-Val, Gly-Gly-Ile, Phe-Phe-Ile, Thr-Thr-Val, Gly-Leu-Val, Phe-Phe-Leu, or Tyr-Pro-Val.

75. The method of claim 59, wherein each tripeptide is one of Asp-Asp-Ile, Gly-Tyr-Ile, Phe-Phe-Val, Tyr-Tyr-Ile, Asp-Asp-Val, Gly-Tyr-Leu, Phe-Val-Val, Tyr-Tyr-Phe, Glu-Asp-Val, Gly-Tyr-Val, Pro-Glu-Val, Tyr-Tyr-Val, Gln-Gln-Val, Ile-Tyr-Val, Pro-Pro-Ile, Val-Glu-Gly, Glu-Leu-Val, Leu-Tyr-Val, Pro-Pro-Len, Gln-Pro-Val, Lys-Lys-Leu, Pro-Pro-Val, Glu-Tyr-Val, Lys-Lys-Val, Ser-Gly-Val, Gly-Glu-Val, Lys-Ser-Val, Ser-Thr-Val, Gly-Gly-Ile, Phe-Phe-Ile, Thr-Thr-Val, Gly-Len-Val, Phe-Phe-Len, Tyr-Pro-Val.

76. The method of claim 59, wherein each oligopeptide is Glu-Asp-Val.

77. The method of claim 59, wherein each oligopeptide is Ser-Gly-Val.

78. The method of claim 74, wherein said oral dosage form is a tablet, a capsule, an oral solution, or an oral suspension.

79. The method of claim 75, wherein said oral dosage form is a tablet, a capsule, an oral solution, or an oral suspension.

80. The method of claim 76, wherein said oral dosage form is a tablet, a capsule, an oral solution, or an oral suspension.

81. The method of claim 77, wherein said oral dosage form is a tablet, a capsule, an oral solution, or an oral suspension.

82. The method of any of claims 59, 67, or 77, wherein the method prevents spiking or increased blood serum concentrations when delivered at doses exceeding those within the therapeutic range of said oxycodone.

83. The method of any of claims 59, 67, or 77, wherein the pharmacological activity of oxycodone is substantially decreased when the composition is used in a manner inconsistent with the manufacturer's instructions as compared to unbound oxycodone.

84. The method of any of claims 59, 67, or 77, wherein said oxycodone is released into a patient's bloodstream at levels that give rise to a reduced or delayed $C_{max}$ spike for oxycodone and provides a therapeutically effective bioavailability curve.

85. The method of any of claims 59, 67, or 77, wherein the bioavailability of the covalently modified oxycodone is diminished and delayed when delivered by routes other than oral administration as compared to unbound oxycodone.

86. The method of any of claims 59, 67, or 77, wherein the method provides a therapeutically effective bioavailability curve when delivered orally and in accordance with a manufacturer's instructions.

87. The method of any of claims 59, 67, or 77, wherein the method prevents spiking or increased blood serum concentrations when delivered at doses exceeding those within the therapeutic range of said oxycodone.

* * * * *

SEQUENCE LISTING

```
<160> NUMBER OF SEQ ID NOS: 7

<210> SEQ ID NO 1
<211> LENGTH: 5
<212> TYPE: PRT
<213> ORGANISM: artificial sequence
<220> FEATURE:
<223> OTHER INFORMATION: synthetic carrier

<400> SEQUENCE: 1

Glu Glu Phe Phe Ile
```

```
1               5

<210> SEQ ID NO 2
<211> LENGTH: 5
<212> TYPE: PRT
<213> ORGANISM: artificial sequence
<220> FEATURE:
<223> OTHER INFORMATION: synthetic carrier

<400> SEQUENCE: 2

Glu Glu Phe Phe Phe
1               5

<210> SEQ ID NO 3
<211> LENGTH: 5
<212> TYPE: PRT
<213> ORGANISM: artificial sequence
<220> FEATURE:
<223> OTHER INFORMATION: synthetic carrier

<400> SEQUENCE: 3

Tyr Tyr Phe Phe Ile
1               5

<210> SEQ ID NO 4
<211> LENGTH: 5
<212> TYPE: PRT
<213> ORGANISM: artificial sequence
<220> FEATURE:
<223> OTHER INFORMATION: synthetic carrier

<400> SEQUENCE: 4

Tyr Tyr Lys Tyr Tyr
1               5

<210> SEQ ID NO 5
<211> LENGTH: 5
<212> TYPE: PRT
<213> ORGANISM: artificial sequence
<220> FEATURE:
<223> OTHER INFORMATION: synthetic carrier

<400> SEQUENCE: 5

Phe Phe Lys Phe Phe
1               5

<210> SEQ ID NO 6
<211> LENGTH: 4
<212> TYPE: PRT
<213> ORGANISM: artificial sequence
<220> FEATURE:
<223> OTHER INFORMATION: synthetic carrier

<400> SEQUENCE: 6

Lys Lys Gly Gly
1

<210> SEQ ID NO 7
<211> LENGTH: 5
<212> TYPE: PRT
<213> ORGANISM: artificial sequence
<220> FEATURE:
<223> OTHER INFORMATION: synthetic carrier
```

-continued

```
<400> SEQUENCE: 7

Gly Gly Lys Gly Gly
1               5
```